United States Patent
Brias et al.

(10) Patent No.: US 10,501,481 B2
(45) Date of Patent: *Dec. 10, 2019

(54) HETEROCYCLIC COMPOUNDS AND THEIR USE IN PREVENTING OR TREATING BACTERIAL INFECTIONS

(71) Applicant: MUTABILIS, Paris (FR)

(72) Inventors: Julie Brias, Paris (FR); Sophie Chasset, Nandy (FR); Francis Chevreuil, Chantilly (FR); Nicolas Lecointe, Paris (FR); Benôit Ledoussal, Pommerit Jaudy (FR); Frédéric Le Strat, Combs la Ville (FR); Sophie Vomscheid, Malakoff (FR); Sébastien Richard, Paris (FR); Fabien Faivre, Drancy (FR); Julien Barbion, Sannois (FR); Audrey Caravano, Enghien les Bains (FR); Géraldine Le Fralliec, Bondy (FR); Christophe Simon, Chevilly Larue (FR)

(73) Assignee: MUTABILIS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/563,889

(22) PCT Filed: Apr. 1, 2016

(86) PCT No.: PCT/EP2016/057274
§ 371 (c)(1),
(2) Date: Oct. 2, 2017

(87) PCT Pub. No.: WO2016/156597
PCT Pub. Date: Oct. 6, 2016

(65) Prior Publication Data
US 2018/0118765 A1 May 3, 2018

(30) Foreign Application Priority Data

Apr. 3, 2015 (EP) .................................... 15305508
Jan. 26, 2016 (EP) .................................... 16305069

(51) Int. Cl.
C07D 471/18 (2006.01)
C07D 513/18 (2006.01)
A61P 31/04 (2006.01)
A61K 31/439 (2006.01)
A61K 31/546 (2006.01)

(52) U.S. Cl.
CPC .......... *C07D 513/18* (2013.01); *A61K 31/439* (2013.01); *A61K 31/546* (2013.01); *A61P 31/04* (2018.01); *C07D 471/18* (2013.01)

(58) Field of Classification Search
CPC ........................... C07D 471/18; C07D 513/18
See application file for complete search history.

(56) References Cited

U.S. PATENT DOCUMENTS

| 5,854,239 A | 12/1998 | Howard et al. |
| 8,148,366 B2 * | 4/2012 | Ledoussal ............ C07D 487/18 514/221 |
| 2010/0087648 A1 | 4/2010 | Lampilas et al. |

FOREIGN PATENT DOCUMENTS

| CN | 102203094 A | 9/2011 |
| RU | 1107541 A1 | 10/1995 |
| RU | 2124014 C1 | 12/1998 |
| WO | 02/100860 A2 | 12/2002 |
| WO | 2013/150296 A1 | 10/2013 |
| WO | 2014/141132 A1 | 9/2014 |

OTHER PUBLICATIONS

"Optical isomers", doi:10.1351/goldbook.O04308, published 1996, accessed Mar. 14, 2019 (Year: 1996).*
"Syphilis—prevention", http://www.webmd.com/sexual-conditions/tc/syphilis-prevention?print=true, last updated Oct. 2, 2007, accessed Apr. 9, 2010 (Year: 2010).*
Penn, Journal of General Microbiology, 1985, 131, 2349-57 (Year: 1985).*
International Search Report and Written Opinion for PCT/EP2016/057274 dated May 12, 2016.
European Search Report for EP 15305508.2 dated Jul. 1, 2015.
Office action received in Russian Application No. 2017134055 dated Aug. 30, 2019.

* cited by examiner

*Primary Examiner* — Noble E Jarrell
(74) *Attorney, Agent, or Firm* — Thompson Coburn LLP; Steven M. Ritchey

(57) ABSTRACT

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

21 Claims, No Drawings

HETEROCYCLIC COMPOUNDS AND THEIR USE IN PREVENTING OR TREATING BACTERIAL INFECTIONS

CROSS-REFERENCE TO RELATED APPLICATIONS

This application is a U.S. National Phase application of PCT/EP2016/057274, filed on Apr. 1, 2016, claiming the benefit of European Application No. 15305508.2, filed on Apr. 3, 2015, and European Application No. 16305069.3, filed on Jan. 26, 2016, all of which are incorporated herein by reference in their entireties.

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

It has been described that there is a continuous evolution of antibacterial resistance which could lead to bacterial strains against which known antibacterial compounds are inefficient.

There is thus a need to provide effective compounds and composition that can overcome bacterial antibiotic resistance.

The objective of the present invention is to provide heterocyclic compounds that can be used as antibacterial agents and/or beta-lactamase inhibitors.

An objective of the present invention is also to provide heterocyclic compounds that can be used for the prevention or for the treatment of bacterial infections.

Another objective of the present invention is to provide heterocyclic compounds that can overcome bacterial antibiotic resistance.

An objective of the invention is also to provide pharmaceutical compositions comprising such heterocyclic compounds, optionally in combination with one or more other antibacterial agent, for the prevention or for the treatment of bacterial infections and which can overcome bacterial antibiotic resistance.

Other objectives will appear throughout the description of the invention.

The present invention thus provides a compound of formula (I)

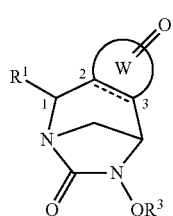

(I)

wherein
- W, unsubstituted or substituted by one or more T, represents a non-aromatic, unsaturated 5- or 6-membered heterocycle comprising at least one group N—$R^2$ and a group $(X)_n$;
- X, identical or different, independently represents C(O), O, N, N($R^2$), S, S(O) or $S(O)_2$;
- $R^1$ represents a carbon-linked, unsubstituted or substituted by one or more $T^1$, aromatic, saturated, totally or partially unsaturated 4-, 5- or 6-membered heterocycle comprising at least one nitrogen atom; a hydrogen atom; —CN; —C(O)$NHQ^1$; —C(O)$NHOQ^1$; —C(O)NH—$NHQ^1$; —C(O)O—$NHQ^1$; —C(O)$OQ^1$; —$(CH_2)_mOC(O)OQ^1$; —$(CH_2)_mOQ^1$; —$(CH_2)_mOC(O)Q^1$; —$(CH_2)_mOC(O)NQ^1Q^2$; —$(CH_2)_m$—NHC(O)$Q^1$; —$(CH_2)_mNHS(O)_2Q^1$; —$(CH_2)_mNHS(O)_2NQ^1Q^2$; —$(CH_2)_mNHC(O)OQ^1$; —$(CH_2)_mNHC(O)NQ^1Q^2$; —$(CH_2)_mNHQ^3$; —$(CH_2)_mNH$—C($NHQ^3$)=$NQ^4$; —$(CH_2)_mNH$—CH=$NQ^3$; —C($NHQ^3$)=$NQ^4$;
- $R^2$, identical or different, independently represents —$(CH_2)_qOQ^5$; —C(O)$(CH_2)_vOQ^5$; —(C(O))$_w$ $(CH_2)_v$—CN; —$(CH_2)_qOC(O)Q^5$; —C(O)—$(CH_2)_vOC(O)Q^5$; —(C(O))$_w(CH_2)_v$—C(O)$OQ^5$; —$(CH_2)_q$—OC(O)$OQ^5$; —C(O)$(CH_2)_v$—OC(O)$OQ^5$; —$(CH_2)_q$—OC(O)$NQ^5Q^6$; —C(O)$(CH_2)_v$—OC(O)$NQ^5Q^6$; —(C(O))$_w(CH_2)_v$—C(O)$NQ^5Q^6$; —(C(O))$_w$ $(CH_2)_v$—C(O)$ONQ^5$; —(C(O))$_w(CH_2)_v$—C(O)$NHOQ^5$; —(C(O))$_w(CH_2)_v$—C(O)NH—$NHQ^5$; —(C(O))$_w(CH_2)_v$—C(O)O—$NHQ^5$; —$(CH_2)_q$—NHC(O)$Q^5$; —C(O)$(CH_2)_v$—NHC(O)$Q^5$; —$(CH_2)_q$ $NHS(O)_2Q^5$; —C(O)$(CH_2)_v$$NHS(O)_2Q^5$; —$(CH_2)_qNHS(O)_2NQ^5Q^6$; —C(O)$(CH_2)_v$$NHS(O)_2$$NQ^5Q^6$; $(CH_2)_q$—NHC(O)$OQ^5$; —C(O)$(CH_2)_v$—NHC(O)$OQ^5$; —$(CH_2)_q$—NHC(O)$NQ^5Q^6$; —C(O) $(CH_2)_v$—NHC(O)$NQ^5Q^6$; —$(CH_2)_qNQ^5Q^6$; —C(O) $(CH_2)_vNQ^5Q^6$; —$(CH_2)_q$—NH—C($NHQ^3$)=$NQ^4$; —C(O)$(CH_2)_v$—NH—C($NHQ^3$)=$NQ^4$; —$(CH_2)_q$— NH—CH=$NQ^3$; —C(O)$(CH_2)_v$—NH—CH=$NQ^3$; —(C(O))$_w(CH_2)_v$—C($NHQ^3$)=$NQ^4$; —C(O)$NQ^5Q^6$; —C($NHQ^3$)=$NQ^4$; or
- $R^2$, identical or different, independently unsubstituted or substituted by one or more $T^2$, independently represents —(C(O))$_w$—$C_1$-$C_3$-alkyl; —(C(O))$_w$— $C_1$-$C_3$-fluoroalkyl; —(C(O))$_w(CH_2)_p$—$C_3$-$C_6$-cycloalkyl; —(C(O))$_w$—$(CH_2)_p$—$C_3$-$C_6$-cyclofluoroalkyl; —(C(O))$_w$—$(CH_2)_p$-(4-, 5- or 6-membered aromatic, saturated, totally or partially unsaturated heterocycle);
- $R^3$ represents $SO_3H$, $CFHCO_2H$ or $CF_2CO_2H$;
- $Q^1$ and $Q^2$, identical or different, independently represent a hydrogen atom; —$(CH_2)_qNHQ^3$; —$(CH_2)_q$—NH—C($NHQ^3$)=$NQ^4$; $(CH_2)_q$—NH—CH=$NQ^3$; $(CH_2)_v$—C($NHQ^3$)=$NQ^4$; —$(CH_2)_qOQ^3$; —$(CH_2)_vCONHQ^3$; or
- $Q^1$ and $Q^2$, identical or different, independently unsubstituted or substituted by one or more $T^2$, independently represent a $C_1$-$C_3$-alkyl; —$(CH_2)_p$-(4-, 5- or 6-membered heterocycle); or
- $Q^1$, $Q^2$ and the nitrogen atom to which they are bonded, form a saturated or partially unsaturated 4-, 5- or 6-membered heterocycle comprising 1, 2, 3 or 4 heteroatoms;
- $Q^3$ and $Q^4$, identical or different, independently represent a hydrogen atom or a $C_1$-$C_3$-alkyl;
- $Q^5$ and $Q^6$, identical or different, independently represent a hydrogen atom; —$(CH_2)_qNHQ^3$; —$(CH_2)_q$—NH— C($NHQ^3$)=$NQ^4$; $(CH_2)_q$—NH—CH=$NQ^3$; $(CH_2)_v$— C($NHQ^3$)=$NQ^4$; —$(CH_2)_qOQ^3$; —$(CH_2)_vCONHQ^3$; or
- $Q^5$ and $Q^6$, identical or different, independently unsubstituted or substituted by one or more $T^2$, independently represent a $C_1$-$C_4$-alkyl, preferably $C_1$-$C_3$-alkyl; —$(CH_2)_p$-(4-, 5- or 6-membered heterocycle); or $Q^5$, $Q^6$ and the nitrogen atom to which they are bonded, form a saturated or partially unsaturated 4-, 5- or 6-membered heterocycle comprising 1, 2, 3 or 4 heteroatoms;

$T^1$, identical or different, independently represents a fluorine atom; —$(CH_2)_pOQ^1$; —$(CH_2)_p$—CN; —$(CH_2)_pOC(O)Q^1$; —$(CH_2)_p$—C(O)O$Q^1$; —$(CH_2)_p$—OC(O)O$Q^1$; —$(CH_2)_p$—OC(O)NH$Q^1$; —$(CH_2)_p$—C(O)NH$Q^1$; —$(CH_2)_p$—C(O)NHO$Q^1$; —$(CH_2)_p$—C(O)NH—NH$Q^1$; —$(CH_2)_p$—C(O)O—NH$Q^1$; —$(CH_2)_p$—NHC(O)$Q^1$; —$(CH_2)_p$NHS(O)$_2Q^1$; —$(CH_2)_p$NHS(O)$_2$N$Q^1Q^2$; —$(CH_2)_p$—NHC(O)O$Q^1$; —$(CH_2)_p$—NHC(O)N$Q^1Q^2$; —$(CH_2)_p$NH$Q^1$; —$(CH_2)_p$—NH—C(NH$Q^3$)=N$Q^4$; —$(CH_2)_p$—NH—CH=N$Q^3$; $(CH_2)_p$—C(NH$Q^3$)=N$Q^4$; or $T^1$, unsubstituted or substituted by one or more $T^2$, identical or different, independently represents $C_1$-$C_3$-alkyl; $C_1$-$C_3$-fluoroalkyl; O—$C_1$-$C_3$-fluoroalkyl; —$(CH_2)_p$-(4-, 5- or 6-membered aromatic, saturated, totally or partially unsaturated heterocycle comprising at least one nitrogen atom);

$T^2$, identical or different, independently represents OH; NH$_2$ or CONH$_2$;

T, identical or different, independently represents a fluorine atom; $C_1$-$C_3$-alkyl; $C_1$-$C_3$-fluoroalkyl; O—$C_1$-$C_3$-fluoroalkyl; -(L)$_w$-(CH$_2$)$_p$—$C_3$-$C_6$-cycloalkyl; -(L)$_w$-(CH$_2$)$_p$—$C_3$-$C_6$-cyclofluoroalkyl; -(L)$_w$-(CH$_2$)$_p$-heterocycle; -(L)$_w$-(CH$_2$)$_p$—CN; -(L)$_w$-(CH$_2$)$_p$OC(O)$Q^5$; -(L)$_w$-(CH$_2$)$_p$—C(O)O$Q^5$; -(L)$_w$-(CH$_2$)$_p$—OC(O)O$Q^5$; -(L)$_w$-(CH$_2$)$_p$—OC(O)N$Q^5Q^6$; -(L)$_w$-(CH$_2$)$_p$—C(O)N$Q^5Q^6$; -(L)$_w$-(CH$_2$)$_p$—C(O)N$Q^5$O$Q^6$; -(L)$_w$-(CH$_2$)$_p$—C(O)N$Q^5$-N$Q^5Q^6$; -(L)$_w$-(CH$_2$)$_p$—N$Q^5$C(O)$Q^6$; -(L)$_w$-(CH$_2$)$_p$N$Q^5Q$(O)$_2Q^6$; -(L)$_w$-(CH$_2$)$_p$—N$Q^5$C(O)O$Q^6$; -(L)$_w$-(CH$_2$)$_p$—N$Q^5$C(O)N$Q^5Q^6$; -(L)$_w$-(CH$_2$)$_p$N$Q^5Q^6$; -(L)$_w$-(CH$_2$)$_p$—NH—C(NH$Q^3$)=N$Q^4$; -(L)$_w$-(CH$_2$)$_p$—NH—CH=N$Q^3$; -(L)$_w$(CH$_2$)$_p$—C(NH$Q^3$)=N$Q^4$;

L, identical or different, independently represents O, S, N(R$^2$), S(O) or S(O)$_2$;

m represents 1 or 2;

n represents 0, 1 or 2;

p, identical or different, independently represents 0, 1, 2 or 3;

q, identical or different, independently represents 2 or 3;

v, identical or different, independently represents 1, 2 or 3;

w, identical or different, independently represents 0 or 1;

wherein
any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a S(O)$_2$ group;

any nitrogen atom present within a heterocycle or present within group wherein it is trisubstituted thus forming a tertiary amino group, can be further quaternized by a methyl group;

and a pharmaceutically acceptable salt, a zwitterion, an optical isomer, a racemate, a diastereoisomer, an enantiomer, a geometric isomer or a tautomer thereof.

For the compounds according to the invention, W, unsubstituted or substituted by one or more T, represents a non-aromatic, unsaturated 5- or 6-membered heterocycle comprising at least one group N—R$^2$ and a group (X)$_n$.

According to the invention, heterocycle W comprises a double bond between the 2- and 3-position carbon atoms or two double bonds on these 2- and 3-position carbon atoms. The carbon atoms in the 2- and 3-position are thus different from sp$^3$ carbon atoms.

According to the invention, heterocycle W comprises at least one heteroatom that is a nitrogen atom. Heterocycle W can further comprise one or two further heteroatoms. These further heteroatoms can be selected from an oxygen atom, a nitrogen atom and a sulfur atom. The carbon atoms or the sulfur atoms possibly present in heterocycle W may be oxidized to form C(O) groups, S(O) or S(O)$_2$ groups.

According to the invention, heterocycle W is a monocycle.

Preferably, in the compounds of formula (I):

W, unsubstituted or substituted by one or more T, represents a non-aromatic, unsaturated 5- or 6-membered heterocycle comprising at least one group N—R$^2$ and a group (X)$_n$;

X, identical or different, independently represents C(O), O, N, N(R$^2$), S, S(O) or S(O)$_2$;

R$^1$ represents a carbon-linked, unsubstituted or substituted by one or more T$^1$, aromatic, saturated, totally or partially unsaturated 4-, 5- or 6-membered heterocycle comprising at least one nitrogen atom; a hydrogen atom; —CN; —C(O)NH$Q^1$; —C(O)NHO$Q^1$; —C(O)NH—NH$Q^1$; —C(O)O—NH$Q^1$; —C(O)O$Q^1$; —(CH$_2$)$_m$OC(O)O$Q^1$; —(CH$_2$)$_m$O$Q^1$; —(CH$_2$)$_m$OC(O)$Q^1$; —(CH$_2$)$_m$OC(O)N$Q^1Q^2$; —(CH$_2$)$_m$—NHC(O)$Q^1$; —(CH$_2$)$_m$NHS(O)$_2Q^1$; —(CH$_2$)$_m$NHS(O)$_2$N$Q^1Q^2$; —(CH$_2$)$_m$NHC(O)O$Q^1$; —(CH$_2$)$_m$NHC(O)N$Q^1Q^2$; —(CH$_2$)$_m$NH$Q^3$; —(CH$_2$)$_m$NH—C(NH$Q^3$)=N$Q^4$; —(CH$_2$)$_m$NH—CH=N$Q^3$; —C(NH$Q^3$)=N$Q^4$;

R$^2$, identical or different, independently represents —(CH$_2$)$_q$O$Q^5$; —(CH$_2$)$_v$—CN; —(CH$_2$)$_q$OC(O)$Q^5$; —(CH$_2$)$_v$—C(O)O$Q^5$; —(CH$_2$)$_q$—OC(O)O$Q^5$; —(CH$_2$)$_q$—OC(O)N$Q^5Q^6$; —(CH$_2$)$_v$—C(O)N$Q^5Q^6$; —(CH$_2$)$_v$—C(O)ON$Q^5$; —(CH$_2$)$_v$—C(O)NHO$Q^5$; —(CH$_2$)$_v$—C(O)NH—NH$Q^5$; —(CH$_2$)$_v$—C(O)O—NH$Q^5$; —(CH$_2$)$_q$—NHC(O)$Q^5$; —(CH$_2$)$_q$NHS(O)$_2Q^5$; —(CH$_2$)$_q$NHS(O)$_2$N$Q^5Q^6$—(CH$_2$)$_q$—NHC(O)O$Q^5$; —(CH$_2$)$_q$—NHC(O)N$Q^5Q^6$; —(CH$_2$)$_q$N$Q^5Q^6$; —(CH$_2$)$_q$—NH—C(NH$Q^3$)=N$Q^4$; —(CH$_2$)$_q$—NH—CH=N$Q^3$; (CH$_2$)$_v$—C(NH$Q^3$)=N$Q^4$; or R$^2$, identical or different, independently unsubstituted or substituted by one or more T$^2$, independently represents $C_1$-$C_3$-alkyl, $C_1$-$C_3$-fluoroalkyl; —(CH$_2$)$_p$—$C_3$-$C_6$-cycloalkyl; —(CH$_2$)$_p$—$C_3$-$C_6$-cyclofluoroalkyl; —(CH$_2$)$_p$-(4-, 5- or 6-membered aromatic, saturated, totally or partially unsaturated heterocycle);

R$^3$ represents SO$_3$H, CFHCO$_2$H or CF$_2$CO$_2$H;

$Q^1$ and $Q^2$, identical or different, independently represent a hydrogen atom; —(CH$_2$)$_q$NH$Q^3$; —(CH$_2$)$_q$—NH—C(NH$Q^3$)=N$Q^4$; (CH$_2$)$_q$—NH—CH=N$Q^3$; (CH$_2$)$_v$—C(NH$Q^3$)=N$Q^4$; —(CH$_2$)$_q$O$Q^3$; —(CH$_2$)$_v$CONH$Q^3$; or $Q^1$ and $Q^2$, identical or different, independently unsubstituted or substituted by one or more T$^2$, independently represent a $C_1$-$C_3$-alkyl; —(CH$_2$)$_p$-(4-, 5- or 6-membered heterocycle); or $Q^1$, $Q^2$ and the nitrogen atom to which they are bonded, form a saturated or partially unsaturated 4-, 5- or 6-membered heterocycle comprising 1, 2, 3 or 4 heteroatoms;

$Q^3$ and $Q^4$, identical or different, independently represent a hydrogen atom or a $C_1$-$C_3$-alkyl;

$Q^5$ and $Q^6$, identical or different, independently represent a hydrogen atom; —(CH$_2$)$_q$NH$Q^3$; —(CH$_2$)$_q$—NH—

C(NHQ³)=NQ⁴; (CH₂)_q—NH—CH=NQ³; (CH₂)_v—C(NHQ³)=NQ⁴; —(CH₂)_qOQ³; —(CH₂)_vCONHQ³; or

Q⁵ and Q⁶, identical or different, independently unsubstituted or substituted by one or more T², independently represent a C₁-C₃-alkyl; —(CH₂)_p-(4-, 5- or 6-membered heterocycle); or Q⁵ Q⁶ and the nitrogen atom to which they are bonded, form a saturated or partially unsaturated 4-, 5- or 6-membered heterocycle comprising 1, 2, 3 or 4 heteroatoms;

T¹, identical or different, independently represents a fluorine atom; —(CH₂)_pOQ¹; —(CH₂)_p—CN; —(CH₂)_pOC(O)Q¹; —(CH₂)_p—C(O)OQ¹; —(CH₂)_p—OC(O)OQ¹; —(CH₂)_p—OC(O)NHQ¹; —(CH₂)_p—C(O)NHQ¹; —(CH₂)_p—C(O)NHOQ¹; —(CH₂)_p—C(O)NH—NHQ¹; —(CH₂)_p—C(O)O—NHQ¹; —(CH₂)_p—NHC(O)Q¹; —(CH₂)_pNHS(O)₂Q¹; —(CH₂)_pNHS(O)₂NQ¹Q²; —(CH₂)_p—NHC(O)OQ¹; —(CH₂)_p—NHC(O)NQ¹Q²; —(CH₂)_pNHQ¹; —(CH₂)_p—NH—C(NHQ³)=NQ⁴; —(CH₂)_p—NH—CH=NQ³; (CH₂)_p—C(NHQ³)=NQ⁴; or T¹, unsubstituted or substituted by one or more T², identical or different, independently represents C₁-C₃-alkyl; C₁-C₃-fluoroalkyl; O—C₁-C₃-fluoroalkyl; —(CH₂)_p-(4-, 5- or 6-membered aromatic, saturated, totally or partially unsaturated heterocycle comprising at least one nitrogen atom);

T², identical or different, independently represents OH; NH₂ or CONH₂;

T, identical or different, independently represents a fluorine atom; C₁-C₃-alkyl; C₁-C₃-fluoroalkyl; O—C₁-C₃-fluoroalkyl; -(L)_w-(CH₂)_p—C₃-C₆-cycloalkyl; -(L)_w-(CH₂)_p—C₃-C₆-cyclofluoroalkyl; -(L)_w-(CH₂)_p-heterocycle; -(L)_w-(CH₂)_p—CN; -(L)_w-(CH₂)_pOC(O)Q⁵; -(L)_w-(CH₂)_p—C(O)OQ⁵; -(L)_w-(CH₂)_p—OC(O)OQ⁵; -(L)_w(CH₂)_p—OC(O)NQ⁵Q⁶; -(L)_w-(CH₂)_p—C(O)NQ⁵Q⁶; -(L)_w-(CH₂)_p—C(O)NQ⁵OQ⁶; -(L)_w-(CH₂)_p—C(O)NQ⁵-NQ⁵Q⁶; -(L)_w-(CH₂)_p—NQ⁵C(O)Q⁶; -(L)_w-(CH₂)_pNQ⁵Q(O)₂Q⁶; -(L)_w-(CH₂)_p—NQ⁵C(O)OQ⁶; -(L)_w-(CH₂)_p—NQ⁵C(O)NQ⁵Q⁶; -(L)_w-(CH₂)_pNQ⁵Q⁶; -(L)_w-(CH₂)_p—NH—C(NHQ³)=NQ⁴; -(L)_w-(CH₂)_p—NH—CH=NQ³; -(L)_w(CH₂)_p—C(NHQ³)=NQ⁴;

L, identical or different, independently represents O, S, N(R), S(O) or S(O)₂;

m represents 1 or 2;

n represents 0, 1 or 2;

p, identical or different, independently represents 0, 1, 2 or 3;

q, identical or different, independently represents 2 or 3;

v, identical or different, independently represents 1, 2 or 3;

w, identical or different, independently represents 0 or 1; wherein any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a S(O)₂ group;

any nitrogen atom present within a heterocycle or present within group wherein it is trisubstituted thus forming a tertiary amino group, can be further quaternized by a methyl group.

Preferably, the compound according to the invention is selected from the compounds of formulae (A) and (B)

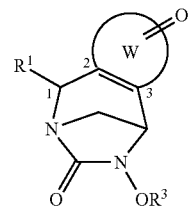
(A)

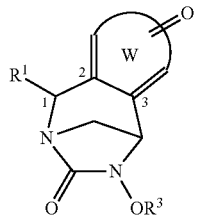
(B)

wherein W, unsubstituted or substituted by one or more T, X, n, R¹, R² and R³ are defined according to formula (I).

Also preferably, the compound according to the invention is selected from the compounds of formulae (A1) to (A68) and (B1) to (B8)

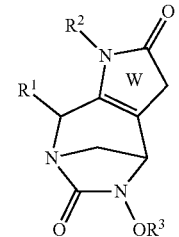
(A1)

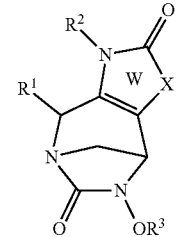
(A2)

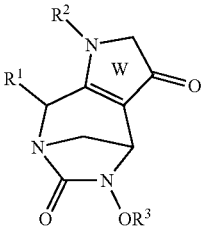
(A3)

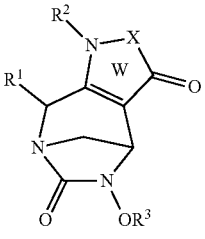
(A4)

(A5) 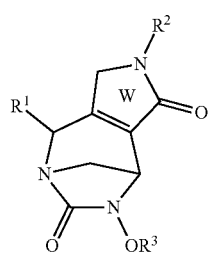
(A6) 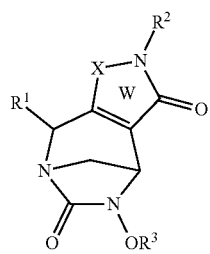
(A7) 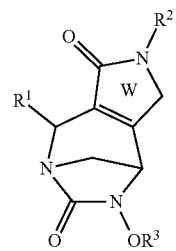
(A8) 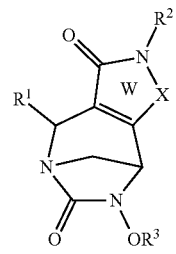
(A9) 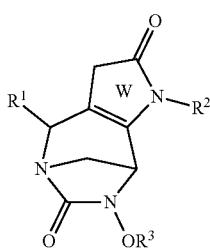
(A10) 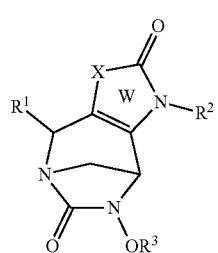
(A11) 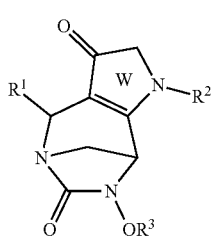
(A12) 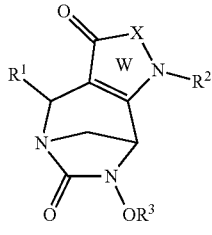
(A13) 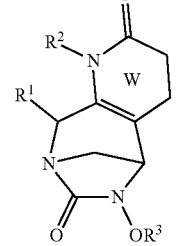
(A14) 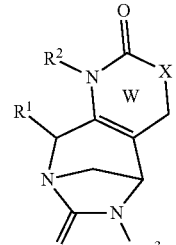
(A15) 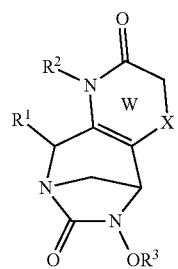
(A16)

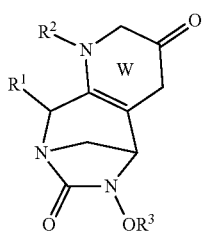
(A17)
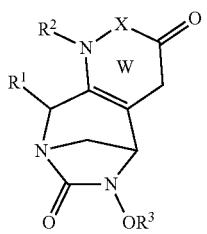
(A18)
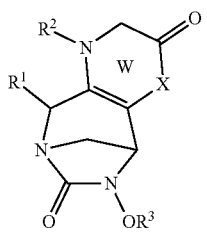
(A19)
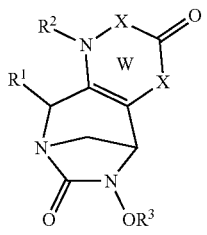
(A20)
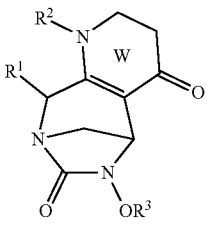
(A21)
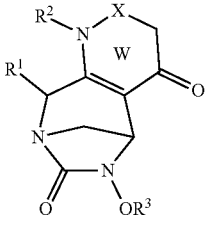
(A22)
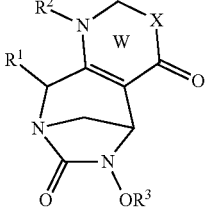
(A23)
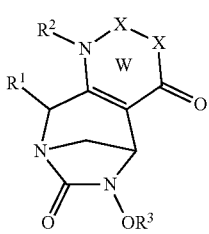
(A24)
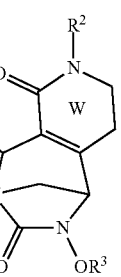
(A25)
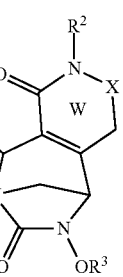
(A26)
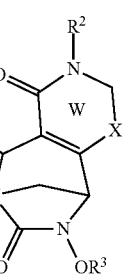
(A27)
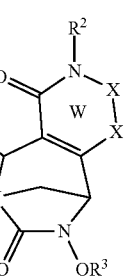
(A28)
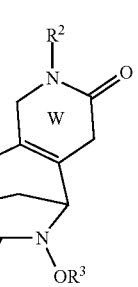
(A29)

-continued
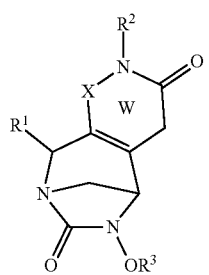
(A30)
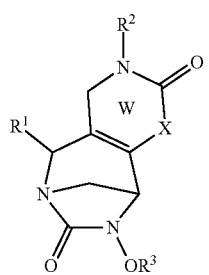
(A31)
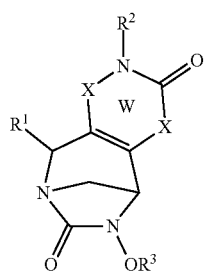
(A32)
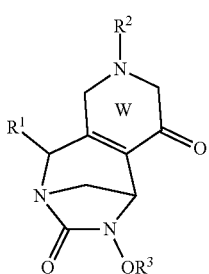
(A33)
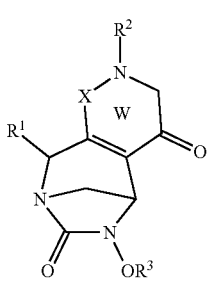
(A34)
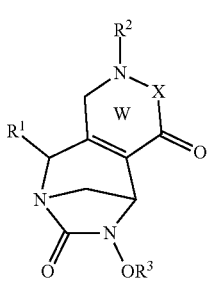
(A35)
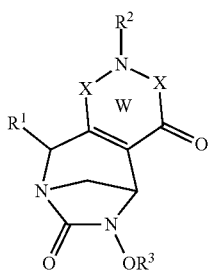
(A36)
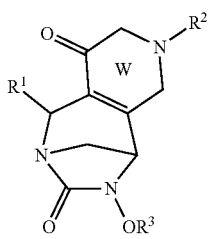
(A37)
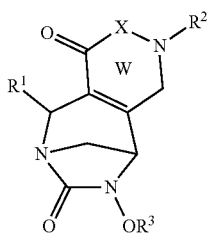
(A38)
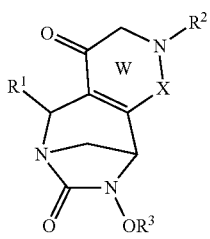
(A39)
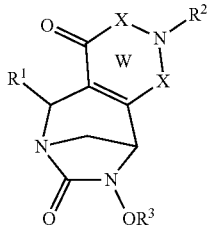
(A40)
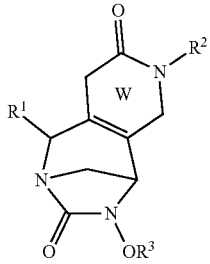
(A41)

(A42) 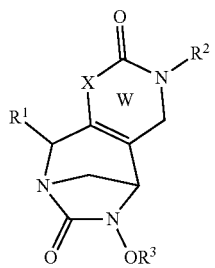
(A43) 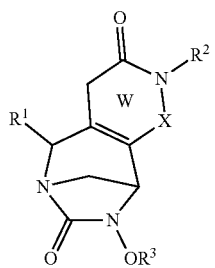
(A44) 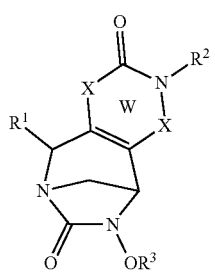
(A45) 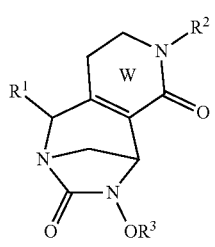
(A46) 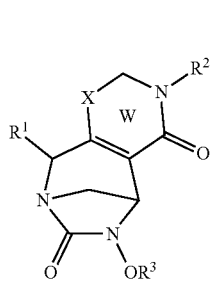
(A47) 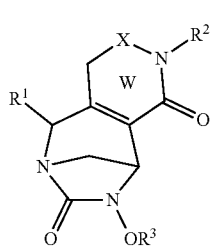
(A48) 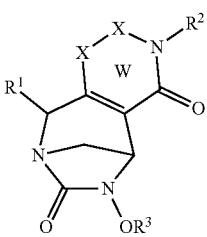
(A49) 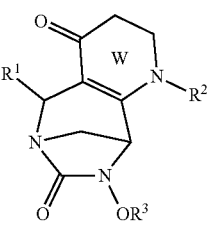
(A50) 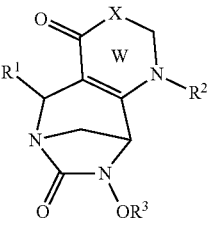
(A51) 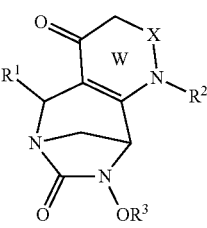
(A52) 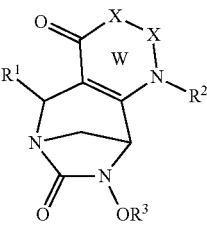
(A53) 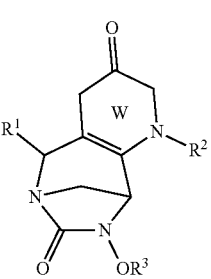

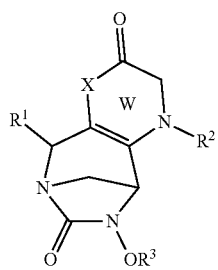 (A54)
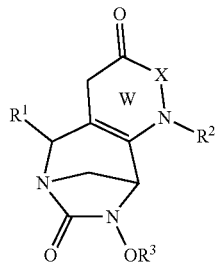 (A55)
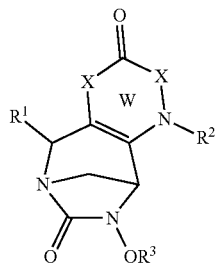 (A56)
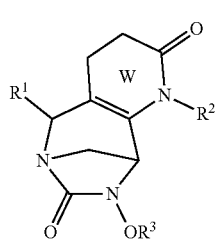 (A57)
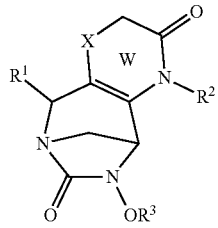 (A58)
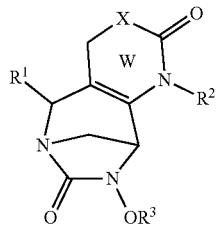 (A59)
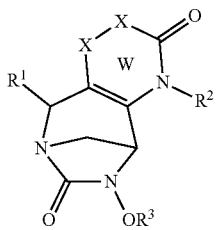 (A60)
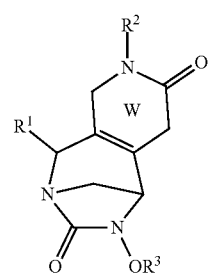 (A61)
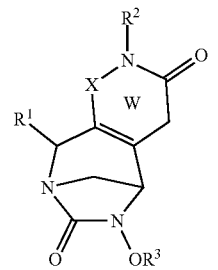 (A62)
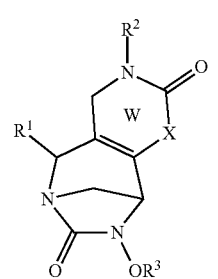 (A63)
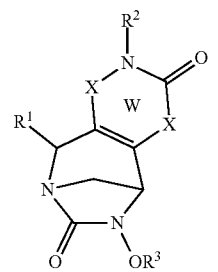 (A64)
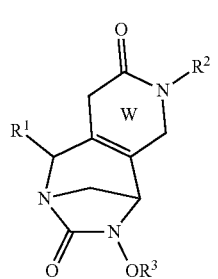 (A65)

-continued
(A66) 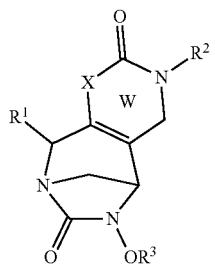
(A67) 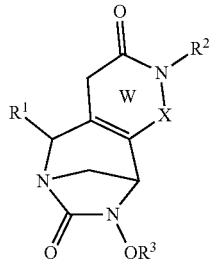
(A68) 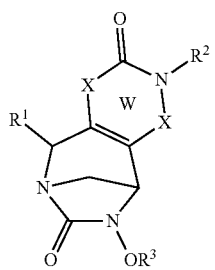
(B1) 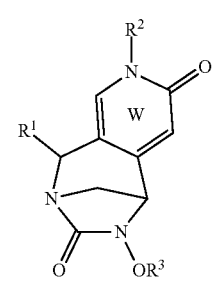
(B2) 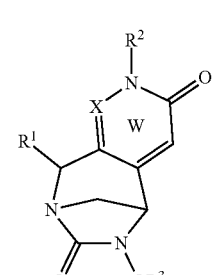
(B3) 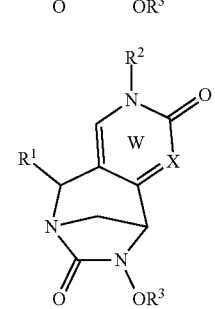
-continued
(B4) 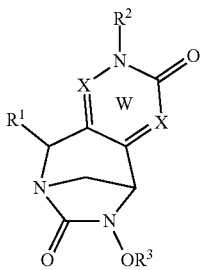
(B5) 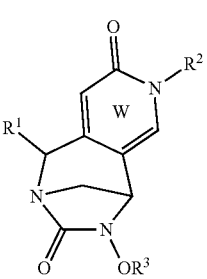
(B6) 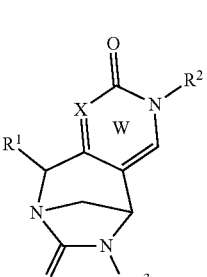
(B7) 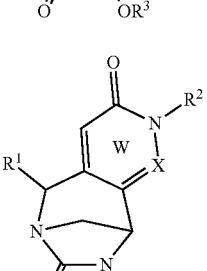
(B8) 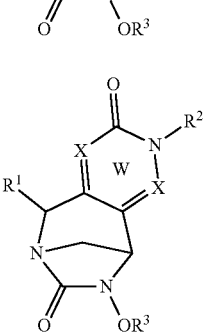
wherein W, unsubstituted or substituted by one or more T, X, $R^1$, $R^2$, $R^3$ and T are defined according to formula (I).
Preferably, the invention relates to compounds of formula (A1) to (A12) preferably to compounds of formula (A2), (A5), (A7) or (A10).
More preferably, the compound according to the invention is selected from the compounds of formulae (I*), (A*), (B*)

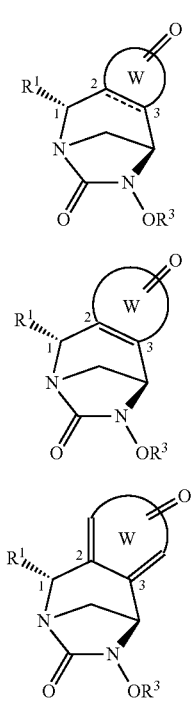

(I*)

(A*)

(B*)

wherein W, unsubstituted or substituted by one or more T, X, n, $R^1$, $R^2$, $R^3$ and T are defined according to formula (I).

The invention also provides compounds of formula (A1*) to (A68*) and (B1*) to (B8*) respectively corresponding to the stereoisomers of the compounds of formulae (A1) to (A68) and (B1) to (B8). Preferably, the invention relates to compounds of formula (A1*) to (A12*) preferably to compounds of formula (A2*), (A5*), (A7*) or (A10*).

Preferred compounds according to the invention are compounds selected from compounds of formulae (I), (A), (B), (A1) to (A68), (B1) to (B8), (I*), (A*), (B*), (A1*) to (A68*) and (B1*) to (B8*) wherein W, unsubstituted or substituted by one or more T, represents a non-aromatic, unsaturated 5-membered heterocycle comprising a group N—$R^2$ and a group $(X)_n$.

Other preferred compounds according to the invention are compounds selected from compounds of formulae (I), (A), (A1) to (A68), (I*), (A*) and (A1*) to (A68*) wherein W, unsubstituted or substituted by one or more T, represents a non-aromatic, unsaturated 5-membered heterocycle comprising a group N—$R^2$ and a group $(X)_n$ and wherein W, unsubstituted or substituted by one or more T, X, $R^1$, $R^2$, $R^3$ and T are defined according to formula (I).

Other preferred compounds according to the invention are compounds selected from compounds of formulae (I), (A), (B), (A1) to (A68), (B1) to (B8), (I*), (A*), (B*), (A1*) to (A68*) and (B1*) to (B8*) wherein W, unsubstituted or substituted by one or more T, represents a non-aromatic, unsaturated 6-membered heterocycle comprising a group N—$R^2$ and a group $(X)_n$ and wherein W, unsubstituted or substituted by one or more T, X, $R^1$, $R^2$, $R^3$ and T are defined according to formula (I).

For the compounds according to the invention, $R^1$ preferably represents a carbon-linked, unsubstituted or substituted by one or more $T^1$, aromatic, saturated, totally or partially unsaturated 4-, 5- or 6-membered heterocycle comprising at least one nitrogen atom; a hydrogen atom; —CN; —C(O)NHQ$^1$; —C(O)NHOQ$^1$; —C(O)NH—NHQ$^1$; —C(O)O—NHQ$^1$; —C(O)OQ$^1$; —(CH$_2$)OC(O)OQ$^1$; —(CH$_2$)$_2$OC(O)OQ$^1$; —(CH$_2$)OQ$^1$; —(CH$_2$)$_2$OQ$^1$; —(CH$_2$)OC(O)Q$^1$; —(CH$_2$)$_2$OC(O)Q$^1$; —(CH$_2$)—OC(O)NQ$^1$Q$^2$; —(CH$_2$)$_2$OC(O)NQ$^1$Q$^2$; —(CH$_2$)NHC(O)Q$^1$; —(CH$_2$)$_2$—NHC(O)Q$^1$; —(CH$_2$)NHS(O)$_2$Q$^1$; —(CH$_2$)$_2$NHS(O)$_2$Q$^1$; —(CH$_2$)NHS(O)$_2$NQ$^1$Q$^2$; —(CH$_2$)$_2$NHS(O)$_2$NQ$^1$Q$^2$; —(CH$_2$)NHC(O)OQ$^1$; —(CH$_2$)$_2$NHC(O)OQ$^1$; —(CH$_2$)NHC(O)NQ$^1$Q$^2$; —(CH$_2$)$_2$NHC(O)NQ$^1$Q$^2$. More preferably, $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —C(O)NHQ$^1$; —C(O)NHOQ$^1$; —C(O)NH—NHQ$^1$; —(CH$_2$)OQ$^1$; or —C(O)OQ$^1$, wherein $Q^1$ is as described in the invention and preferably represents H or methyl.

Preferably, in the compounds of the invention, $R^1$ preferably represents —CN, —C(O)OQ$^1$, —C(O)NHQ$^1$, —C(O)NHOQ$^1$, —C(O)NH—NHQ$^1$, —C(O)O—NHQ$^1$, preferably —CN; C(O)NHQ$^1$, —C(O)NHOQ$^1$, —C(O)NH—NHQ$^1$, wherein $Q^1$ is as defined in the invention.

Preferably, in the compounds of the invention, $R^1$ preferably represents —(CH$_2$)$_m$—OQ$^1$, —(CH$_2$)$_m$—OC(O)Q$^1$, —(CH$_2$)$_m$—OC(O)OQ$^1$, —(CH$_2$)$_m$—OC(O)NQ$^1$Q$^2$, —(CH$_2$)$_m$—NHS(O)$_2$NQ$^1$Q$^2$, —(CH$_2$)$_m$—NHC(O)Q$^1$, —(CH$_2$)$_m$—NHS(O)$_2$Q$^1$, —(CH$_2$)$_m$—NHC(O)OQ$^1$, —(CH$_2$)$_m$—NHC(O)NQ$^1$Q$^2$, preferably —(CH$_1$)$_m$—OQ$^1$, —(CH$_2$)$_m$—OC(O)Q$^1$, —(CH$_2$)$_m$—NHS(O)$_2$NQ$^1$Q$^2$, —(CH$_2$)$_m$—NHC(O)Q$^1$, —(CH$_2$)$_m$—NHC(O)OQ$^1$ or —(CH$_2$)$_m$—NHC(O)NQ$^1$Q$^2$, more preferably —(CH$_2$)$_m$—OQ$^1$, —(CH$_2$)$_m$—NHC(O)Q$^1$, —(CH$_2$)$_m$—NHC(O)OQ$^1$, —(CH$_2$)$_m$—NHC(O)NQ$^1$Q$^2$ wherein $Q^1$ and $Q^2$ are as defined in the invention.

Preferably, in the compounds of the invention, $R^1$ preferably represents a carbon-linked 4-, 5- or 6-membered heterocycle saturated, partially or totally unsaturated or aromatic comprising at least one nitrogen atom and optionally substituted by one or more $T^1$, it can comprise other heteroatoms, for example at least one further heteroatoms, for example 1, 2 or 3 further heteroatoms, the further heteroatom being preferably chosen among N, O, S, S(O) or S(O)$_2$. It is preferably a monocyclic heterocycle.

Preferably, for the compounds of the invention, $R^1$ represents hydrogen atom For the compounds according to the invention, $R^1$ represents equally preferably —(CH$_2$)NHQ$^3$; —(CH$_2$)$_2$NHQ$^3$; —(CH$_2$)NH—C(NHQ$^3$)═NQ$^4$; —(CH$_2$)$_2$NH—C(NHQ$^3$)═NQ$^4$; —(CH$_2$)NH—CH═NQ$^3$; —(CH$_2$)$_2$NH—CH═NQ$^3$; —C(NHQ$^3$)═NQ$^4$. More preferably, $R^1$ represents —(CH$_2$)NHQ$^3$; —(CH$_2$)NH—C(NHQ$^3$)═NQ$^4$, in particular $R^1$ represents —(CH$_2$)NH$_2$ or —(CH$_2$)NH—C(NH$_2$)═NH, wherein $Q^3$ and $Q^4$ are as defined in the invention, preferably H.

Preferably, for the compounds of the invention, $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —C(O)NHQ$^1$; —C(O)NHOQ$^1$; —C(O)NH—NHQ$^1$; —C(O)OQ$^1$; —(CH$_2$)OQ$^1$ or —(CH$_2$)NHQ$^3$; —(CH$_2$)$_2$NHQ$^3$; —(CH$_2$)NH—C(NHQ$^3$)═NQ$^4$; —(CH$_2$)$_2$NH—C(NHQ$^3$)═NQ$^4$; —(CH$_2$)NH—CH═NQ$^3$; —(CH$_2$)$_2$NH—CH═NQ$^3$; —C(NHQ$^3$)═NQ$^4$. More preferably, $R^1$ represents —(CH$_2$)NHQ$^3$; —(CH$_2$)NH—C(NHQ$^3$)═NQ$^4$ wherein $Q^1$ is as described in the invention and preferably represents H or methyl and $Q^3$ and $Q^4$ are as described in the invention, preferably H.

For the compounds according to the invention, $R^1$ may represent a hydrogen atom, or a carbon-linked, unsubstituted or substituted by one or more $T^1$, aromatic, saturated, totally or partially unsaturated 4-, 5- or 6-membered heterocycle that comprises at least one nitrogen atom. Such a 4-, 5- or 6-membered heterocycle may further comprise one or more heteroatoms, for example 1, 2 or 3 further heteroatoms, preferably selected from N, O, S, S(O) or $S(O)_2$, or $—(CH_2)NH_2$ or $—(CH_2)NH—C(NH_2)=NH$.

For the compounds according to the invention, $R^1$ may represent a carbon-linked, unsubstituted or substituted by one or more $T^1$, aromatic, saturated, totally or partially unsaturated 4-, 5- or 6-membered heterocycle that comprises at least one nitrogen atom. Such a 4-, 5- or 6-membered heterocycle may further comprise one or more heteroatoms, for example 1, 2 or 3 further heteroatoms, preferably selected from N, O, S, S(O) or $S(O)_2$.

Preferably, for the compounds of the invention $R^1$ represents a hydrogen atom.

Preferably for the compounds of the invention, $R^2$ is chosen among $—(CH_2)_q NQ^5Q^6$, $—C(O)(CH_2)_v NQ^5Q^6$, $—(CH_2)_q—NH—C(NHQ^3)=NQ^4$; $C(O)NQ^5Q^6$; $—(C(O))_w—(CH_2)_v—C(NHQ^3)=NQ^4$; $—C(NHQ^3)=NQ^4$; $—(C(O))_w—(CH_2)_v—C(O)NQ^5Q^6$; $—(C(O))_w—(CH_2)_p$-(4-, 5- or 6-membered aromatic, saturated, totally or partially unsaturated heterocycle); $—(CH_2)_q NHS(O)_2 NQ^5Q^6$; $—C(O)(CH_2)NHS(O)_2 NQ^5Q^6$; $—(CH_2)_q NHC(O)NQ^5Q^6$; $—C(O)(CH_2)_v NHC(O)NQ^5Q^6$; $—(C(O))_w—(CH_2)_v—C(O)OQ^5$; $(C(O))_w—C_1-C_3$-alkyl; $—(CH_2)_q—NHC(O)OQ^5$; $—C(O)(CH_2)_v—NHC(O)OQ^5$; $—(CH_2)_q OQ^5$, $—C(O)(CH_2)_v OQ^5$, wherein $Q^5$ and $Q^6$ are as defined in the invention, preferably chosen among H, $(CH_2)_q NHQ^3$ or $C_1-C_4$-alkyl, wherein $Q^3$ and $Q^4$ are as defined in the invention, preferably H and w, q, p, v are as defined above.

Preferably for the compounds of the invention, $R^2$ is chosen among $—(CH_2)_q NQ^5Q^6$, $—C(O)(CH_2)NQ^5Q^6$, $C(O)NQ^5Q^6$; $—(C(O))_w—(CH_2)_v—C(NHQ^3)=NQ^4$; $—C(NHQ^3)=NQ^4$; $—(C(O))_w—(CH_2)_v—C(O)NQ^5Q^6$; $—(C(O))_w—(CH_2)_p$-(4-, 5- or 6-membered aromatic, saturated, totally or partially unsaturated heterocycle); $—(CH_2)_q NHS(O)_2 NQ^5Q^6$; $—C(O)(CH_2)_v NHS(O)_2 NQ^5Q^6$; $—(CH_2)_q NHC(O)NQ^5Q^6$; $—C(O)(CH_2)_v NHC(O)NQ^5Q^6$; $—(C(O))_w—(CH_2)_v—C(O)OQ^5$; $(C(O))_w—C_1-C_3$-alkyl; $—(CH_2)_q—NHC(O)OQ^5$; $—C(O)(CH_2)_v—NHC(O)OQ^5$; $—(CH_2)_q OQ^5$, $—C(O)(CH_2)_v OQ^5$, wherein $Q^5$ and $Q^6$ are as defined in the invention, preferably chosen among H or $C_1-C_4$-alkyl, wherein $Q^3$ and $Q^4$ are as defined in the invention, preferably H and w, q, p, v are as defined above.

Preferably, for the compounds of the invention $R^2$ is chosen among $(C(O))_w—C_1-C_3$-alkyl, $(C(O))_w—(CH_2)_v—C(O)OQ^5$, $—(CH_2)_q—NH—C(NHQ^3)=NQ^4$; $—(C(O))_w (CH_2)_v—C(O)NQ^5Q^6$; $(C(O))_w—(CH_2)_q NQ^5Q^6$, $—C(O)(CH_2)_v NHC(O)NQ^5Q^6$; $(C(O))_w—(CH_2)_q OQ^5$, $(C(O))_w—(CH_2)_q—NHC(O)OQ^5$; $—(C(O))_w—(CH_2)_p$-(4-, 5- or 6-membered aromatic, saturated, totally or partially unsaturated heterocycle), wherein $Q^5$ and $Q^6$ are as defined in the invention, preferably chosen among H or $C_1-C_4$-alkyl, $(CH_2)_q NHQ^3$, preferably H or $C_1-C_4$-alkyl, q, p and v are as defined above and w is as defined above, preferably w is 0, wherein $Q^3$ and $Q^4$ are as defined in the invention, preferably H.

Preferably, for the compounds of the invention $R^2$ is chosen among $(C(O))_w—C_1-C_3$-alkyl, $(C(O))_w—(CH_2)_v—C(O)OQ^5$, $(C(O))_w—(CH_2)_q NQ^5Q^6$, $(C(O))_w—(CH_2)_q OQ^5$, $(C(O))_w—(CH_2)_q—NHC(O)OQ^5$, wherein $Q^5$ and $Q^6$ are as defined in the invention, preferably chosen among H or $C_1-C_4$-alkyl; q and v are as defined above and w is as defined above, preferably w is 0.

Preferably, for the compounds of the invention $R^2$ is chosen among $—(CH_2)_p$-(4-, 5- or 6-membered aromatic, saturated, totally or partially unsaturated heterocycle), $C_1-C_3$-alkyl, $—(CH_2)_v—C(O)OQ^5$; $—(CH_2)_q—NHC(O)OQ^5$; $—(CH_2)_q NQ^5Q^6$, $—(CH_2)_q OQ^5$, $—(CH_2)_v C(O)NH (CH_2)_q NHQ^3$ wherein $Q^5$ and $Q^6$ are as defined in the invention, preferably chosen among H or $C_1-C_4$-alkyl; q and v are as defined above wherein $Q^3$ is as defined in the invention, preferably H.

For the compounds according to the invention, $R^3$ preferably represents $SO_3H$ or $CF_2COOH$.

For the compounds according to the invention, $Q^1$ and $Q^2$ and the nitrogen atom to which they are bonded, may form together a saturated or partially unsaturated 4-, 5- or 6-membered heterocycle comprising 1, 2 or 3 heteroatoms. The resulting 4-, 5- or 6-membered heterocycle thus comprises the nitrogen atom bonded to $Q^1$ and $Q^2$ and one or two further optional heteroatoms.

For the compounds according to the invention, $Q^1$ and $Q^2$, identical or different, preferably represent H; methyl; $—CH_2—CH_2—NH_2$; $—CH_2—CH_2—NH—CNH_2=NH$; $—CH_2—CH_2—NH—CH=NH$; $—CH_2—C(NH_2)=NH$; $—CH_2—CH_2—OH$; $—CH_2—CONH_2$; a $—(CH_2)_p$-(saturated, partially or totally unsaturated or aromatic 4-, 5- or 6-membered heterocycle comprising at least one nitrogen atom) wherein the heterocycle can be substituted by one or more $T^2$, and p and $T^2$ are defined according to formula (I).

For the compounds according to the invention, $Q^1$ and $Q^2$, identical or different, more preferably represent H; methyl; $—CH_2—CH_2—NH_2$; $—CH_2—CH_2—NH—CNH_2=NH$; $—CH_2—CH_2—NH—CH=NH$; $—CH_2—C(NH_2)=NH$; $—CH_2—CH_2—OH$; $—CH_2—CONH_2$; a saturated, partially or totally unsaturated or aromatic 4-, 5- or 6-membered heterocycle comprising one nitrogen atom wherein the heterocycle can be substituted by one or more $T^2$ that is defined according to formula (I). Preferably, $Q^1$ and $Q^2$, identical or different, more preferably represent H or methyl.

For the compounds according to the invention, $Q^3$ and $Q^4$, identical or different, preferably represent H or methyl.

For the compounds according to the invention, $Q^5$ and $Q^6$ and the nitrogen atom to which they are bonded, may form together a saturated or partially unsaturated 4-, 5- or 6-membered heterocycle comprising 1, 2 or 3 heteroatoms. The resulting 4-, 5- or 6-membered heterocycle thus comprises the nitrogen atom bonded to $Q^5$ and $Q^6$ and one or two further optional heteroatoms.

Preferably, in the compounds of the invention $Q^5$ and $Q^6$, identical or different are H or $C_1-C_4$-alkyl, $(CH_2)_q$, $NHQ^3$, preferably H or $C_1-C_4$-alkyl, preferably H or $C_1-C_3$-alkyl, wherein $Q^3$ is as defined above preferably H.

Preferably, in the compounds of the invention
  $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; $—CN$; $—C(O)NHQ^1$; $—C(O)NHOQ^1$; $—C(O)NH—NHQ^1$; $—(CH_2)OQ^1$; or $—C(O)OQ^1$, wherein $Q^1$ is as described in the invention and preferably represents H or methyl; or
  $R^1$ represents $—(CH_2)NHQ^3$; $—(CH_2)_2 NHQ^3$; $—(CH_2)NH—C(NHQ^3)=NQ^4$; $—(CH_2)_2 NH—C(NHQ^3)=NQ^4$; $—(CH_2)NH—CH=NQ^3$; $—(CH_2)_2 NH—CH=NQ^3$; $—C(NHQ^3)=NQ^4$, more preferably, $R^1$ represents —$(CH_2)NHQ^3$; —$(CH_2)NH$—$C(NHQ^3)$=$NQ^4$, wherein $Q^3$ and $Q^4$ are as described in the invention, preferably H; or $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —$C(O)NHQ^1$; —$C(O)NHQ^1$; —$C(O)NH$—$NHQ^1$; —$C(O)OQ^1$; —$(CH_2)OQ^1$ or —$(CH_2)NHQ^3$; —$(CH_2)_2NHQ^3$; —$(CH_2)NH$—$C(NHQ^3)$=$NQ^4$; —$(CH_2)_2NH$—$C(NHQ^3)$=$NQ^4$; —$(CH_2)NH$—$CH$=$NQ^3$; —$(CH_2)_2NH$—$CH$=$NQ^3$; —$C(NHQ^3)$=$NQ^4$, wherein $Q^1$, $Q^3$ and $Q^4$ are as described in the invention, preferably $Q^1$ represents H or methyl and $Q^3$ and $Q^4$ represents H; and $R^3$ represents $SO_3H$ or $CF_2COOH$, preferably $SO_3H$;

W represents a non-aromatic, unsaturated 5-membered heterocycle comprising a group N—$R^2$ and a group X, wherein $R^2$ is chosen among —$(CH_2)_qNQ^5Q^6$, —$C(O)(CH_2)_vNQ^5Q^6$, —$(CH_2)_q$—NH—$C(NHQ^3)$=$NQ^4$; $C(O)NQ^5Q^6$; —$(C(O))_w(CH_2)_v$—$C(NHQ^3)$=$NQ^4$; —$C(NHQ^3)$=$NQ^4$; —$(C(O))_w(CH_2)_v$—$C(O)NQ^5Q^6$; —$(C(O))_w$—$(CH_2)_p$-(4-, 5- or 6-membered aromatic, saturated, totally or partially unsaturated heterocycle); —$(CH_2)_qNHS(O)_2NQ^5Q^6$; —$C(O)(CH_2)_vNHS(O)_2NQ^5Q^6$; —$(CH_2)_qNHC(O)NQ^5Q^6$; —$C(O)(CH_2)_vNHC(O)NQ^5Q^6$; —$(C(O))_w(CH_2)_v$—$C(O)OQ^5$; $(C(O))_w$—$C_1$-$C_3$-alkyl; —$(CH_2)_q$—$NHC(O)OQ^5$; —$C(O)(CH_2)_v$—$NHC(O)OQ^5$; —$(CH_2)_qOQ^5$, —$C(O)(CH_2)_vOQ^5$, wherein $Q^5$ and $Q^6$ are as defined in the invention, preferably chosen among H or $C_1$-$C_4$-alkyl, $(CH_2)_q$ $NHQ^3$, preferably H or $C_1$-$C_4$-alkyl, wherein $Q^3$ and $Q^4$ are as defined in the invention, preferably H and w, q, p, v are as defined above, and X is a heteroatom, preferably S, O or N, preferably S.

Preferably, in the compounds of the invention $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —$C(O)NHQ^1$; —$C(O)NHOQ^1$; —$C(O)NH$—$NHQ^1$; —$(CH_2)OQ^1$; or —$C(O)OQ^1$, wherein $Q^1$ is as described in the invention and preferably represents H or methyl; or $R^1$ represents —$(CH_2)NHQ^3$; —$(CH_2)_2NHQ^3$; —$(CH_2)NH$—$C(NHQ^3)$=$NQ^4$; —$(CH_2)_2NH$—$C(NHQ^3)$=$NQ^4$; —$(CH_2)NH$—$CH$=$NQ^3$; —$(CH_2)_2NH$—$CH$=$NQ^3$; —$C(NHQ^3)$=$NQ^4$, more preferably, $R^1$ represents —$(CH_2)NHQ^3$; —$(CH_2)NH$—$C(NHQ^3)$=$NQ^4$, wherein $Q^3$ and $Q^4$ are as described in the invention, preferably H; or $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —$C(O)NHQ^1$; —$C(O)NHOQ^1$; —$C(O)NH$—$NHQ^1$; —$C(O)OQ^1$; —$(CH_2)OQ^1$ or —$(CH_2)NHQ^3$; —$(CH_2)_2NHQ^3$; —$(CH_2)NH$—$C(NHQ^3)$=$NQ^4$; —$(CH_2)_2NH$—$C(NHQ^3)$=$NQ^4$; —$(CH_2)NH$—$CH$=$NQ^3$; —$(CH_2)_2NH$—$CH$=$NQ^3$; —$C(NHQ^3)$=$NQ^4$, wherein $Q^1$, $Q^3$ and $Q^4$ are as described in the invention, preferably $Q^1$ represents H or methyl and $Q^3$ and $Q^4$ represents H; and $R^3$ represents $SO_3H$ or $CF_2COOH$, preferably $SO_3H$;

W represents a non-aromatic, unsaturated 5-membered heterocycle comprising a group N—$R^2$ and a group X, wherein $R^2$ is chosen among $(C(O))_w$—$C_1$-$C_3$-alkyl; $(C(O))_w$—$(CH_2)_v$—$C(O)OQ^5$, —$(CH_2)_q$—NH—$C(NHQ^3)$=$NQ^4$; —$(C(O))_w(CH_2)_v$—$C(O)NQ^5Q^6$; $(C(O))_w$—$(CH_2)_qNQ^5Q^6$, —$C(O)(CH_2)_vNHC(O)NQ^5Q^6$; $(C(O))_w$—$(CH_2)_qOQ^5$, $(C(O))_w$—$(CH_2)_q$—$NHC(O)OQ^5$; —$(C(O))_w$—$(CH_2)_p$-(4-, 5- or 6-membered aromatic, saturated, totally or partially unsaturated heterocycle), wherein $Q^5$ and $Q^6$ are as defined in the invention, preferably chosen among H or $C_1$-$C_4$-alkyl, $(CH_2)_q$, $NHQ^3$, preferably H or $C_1$-$C_4$-alkyl; wherein $Q^3$ is as defined in the invention, preferably H, q and v are as defined above and w is as defined above, preferably w is 0, and X is a heteroatom, preferably S, O or N, preferably S.

Preferably, in the compounds of the invention:

$R^1$ represents H;

$R^3$ represents $SO_3H$ or $CF_2COOH$, preferably $SO_3H$;

W represents a non-aromatic, unsaturated 5-membered heterocycle comprising a group N—$R^2$ and a group X, wherein $R^2$ is chosen among —$(CH_2)_p$-(4-, 5- or 6-membered aromatic, saturated, totally or partially unsaturated heterocycle), $C_1$-$C_3$-alkyl, —$(CH_2)_v$—$C(O)OQ^5$; —$(CH_2)_q$—$NHC(O)OQ^5$; —$(CH_2)_qNQ^5Q^6$, —$(CH_2)_qOQ^5$, —$(CH_2)_qC(O)NQ^5Q^6$, wherein $Q^5$ and $Q^6$ are as defined in the invention, preferably chosen among H or $C_1$-$C_4$-alkyl, $(CH_2)_qNHQ^3$, preferably H or $C_1$-$C_4$-alkyl; wherein $Q^3$ is as defined in the invention, preferably H, q and v are as defined above; and X is a heteroatom, preferably S, O or N, preferably S.

Preferably the compounds of the invention are compounds of formula (A) or (A*) wherein:

$R^1$ represents H;

$R^3$ represents $SO_3H$ or $CF_2COOH$, preferably $SO_3H$;

W represents a non-aromatic, unsaturated 5-membered heterocycle comprising a group N—$R^2$ and a group X, wherein $R^2$ is chosen among —$(CH_2)_p$-(4-, 5- or 6-membered aromatic, saturated, totally or partially unsaturated heterocycle), $C_1$-$C_3$-alkyl, —$(CH_2)_v$—$C(O)OQ^5$; —$(CH_2)_q$—$NHC(O)OQ^5$; —$(CH_2)_qNQ^5Q^6$, —$(CH_2)_qOQ^5$, —$(CH_2)_qC(O)NQ^5Q^6$, wherein $Q^5$ and $Q^6$ are as defined in the invention, preferably chosen among H or $C_1$-$C_4$-alkyl, $(CH_2)_q$ $NHQ^3$, preferably H or $C_1$-$C_4$-alkyl; wherein $Q^3$ is as defined in the invention, preferably H, q and v are as defined above; and X is a heteroatom, preferably S, O or N, preferably S.

Preferably the compounds of the invention are compounds of formula (A2) or (A2*) wherein:

$R^1$ represents H;

$R^3$ represents $SO_3H$ or $CF_2COOH$, preferably $SO_3H$;

$R^2$ is chosen among —$(CH_2)_p$-(4-, 5- or 6-membered aromatic, saturated, totally or partially unsaturated heterocycle), $C_1$-$C_3$-alkyl, —$(CH_2)_v$—$C(O)OQ^5$; —$(CH_2)_q$—$NHC(O)OQ^5$; —$(CH_2)_qNQ^5Q^6$, —$(CH_2)_qOQ^5$, —$(CH_2)_qC(O)NQ^5Q^6$, wherein $Q^5$ and $Q^6$ are as defined in the invention, preferably chosen among H or $C_1$-$C_4$-alkyl, $(CH_2)_q$, $NHQ^3$, preferably H or $C_1$-$C_4$-alkyl; q and v are as defined above; and X is a heteroatom, preferably S, O or N, preferably S.

Preferably, in the compounds of the invention $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —$C(O)NHQ^1$; —$C(O)NHOQ^1$; —$C(O)NH$—$NHQ^1$; —$(CH_2)OQ^1$; or —$C(O)OQ^1$, wherein $Q^1$ is as described in the invention and preferably represents H or methyl; or $R^1$ represents —$(CH_2)NHQ^3$; —$(CH_2)_2NHQ^3$; —$(CH_2)NH$—$C(NHQ^3)$=$NQ^4$; —$(CH_2)_2NH$—$C(NHQ^3)$=$NQ^4$; —$(CH_2)NH$—$CH$=$NQ^3$; —$(CH_2)_2NH$—$CH$=$NQ^3$; —$C(NHQ^3)$=$NQ^4$, more preferably, $R^1$ represents —$(CH_2)NHQ^3$; —$(CH_2)NH$—$C(NHQ^3)$=$NQ^4$, wherein $Q^3$ and $Q^4$ are as described in the invention, preferably H; or $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —$C(O)NHQ^1$; —$C(O)NHOQ^1$; —$C(O)NH$—$NHQ^1$; —$C(O)OQ^1$; —$(CH_2)OQ^1$ or —$(CH_2)NHQ^3$; —$(CH_2)_2NHQ^3$; —$(CH_2)NH$—$C(NHQ^3)$=$NQ^4$; —$(CH_2)_2NH$—$C(NHQ^3)$=$NQ^4$; —$(CH_2)NH$—$CH$=$NQ^3$; —$(CH_2)_2NH$—$CH$=$NQ^3$; —$C(NHQ^3)$=$NQ^4$, wherein $Q^1$, $Q^3$ and $Q^4$ are as described in the invention, preferably $Q^1$ represents H or methyl and $Q^3$ and $Q^4$ represents H; and $R^3$ represents $SO_3H$ or $CF_2COOH$, preferably $SO_3H$;

W represents a non-aromatic, unsaturated 5-membered heterocycle comprising a group N—$R^2$ and a group X, wherein $R^2$ is chosen among —$(CH_2)_qNQ^5Q^6$, —$C(O)(CH_2)_vNQ^5Q^6$; $C(O)NQ^5Q^6$; —$(C(O))_w(CH_2)_v$—$C(NHQ^3)$=$NQ^4$; —$C(NHQ^3)$=$NQ^4$; —$(C(O))_w(CH_2)_v$—$C(O)NQ^5Q^6$; —$(C(O))_w$—$(CH_2)_p$-(4-, 5- or 6-membered aromatic, saturated, totally or partially unsaturated heterocycle); —$(CH_2)_qNHS(O)_2NQ^5Q^6$; —$C(O)(CH_2)_vNHS(O)_2NQ^5Q^6$; —$(CH_2)_qNHC(O)NQ^5Q^6$; —$C(O)(CH_2)_vNHC(O)NQ^5Q^6$; —$(C(O))_w(CH_2)_v$—$C(O)OQ^5$; $(C(O))_w$—$C_1$-$C_3$-alkyl; —$(CH_2)_q$—$NHC(O)OQ^5$; —$C(O)(CH_2)_v$—$NHC(O)OQ^5$; —$(CH_2)_qOQ^5$, —$C(O)(CH_2)_vOQ^5$, wherein $Q^5$ and $Q^6$ are as defined above, preferably chosen among H or $C_1$-$C_4$-alkyl, wherein $Q^3$ and $Q^4$ are as defined above preferably H and w, q, p, v are as defined above and X is a heteroatom, preferably S, O or N, preferably S.

Preferably, in the compounds of the invention $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —$C(O)NHQ^1$; —$C(O)NHOQ^1$; —$C(O)NH$—$NHQ^1$; —$(CH_2)OQ^1$; or —$C(O)OQ^1$, wherein $Q^1$ is as described in the invention and preferably represents H or methyl; or $R^1$ represents —$(CH_2)NHQ^3$; —$(CH_2)_2NHQ^3$; —$(CH_2)NH$—$C(NHQ^3)$=$NQ^4$; —$(CH_2)_2NH$—$C(NHQ^3)$=$NQ^4$; —$(CH_2)NH$—$CH$=$NQ^3$; —$(CH_2)_2NH$—$CH$=$NQ^3$; —$C(NHQ^3)$=$NQ^4$, more preferably, $R^1$ represents —$(CH_2)NHQ^3$; —$(CH_2)NH$—$C(NHQ^3)$=$NQ^4$, wherein $Q^3$ and $Q^4$ are as described in the invention, preferably H; or $R^1$ represents hydrogen atom; a carbon-linked, unsubstituted or substituted by one or more $T^1$, aromatic, saturated, totally or partially unsaturated 4-, 5- or 6-membered heterocycle comprising at least one nitrogen atom; —CN; —$C(O)NHQ^1$; —$C(O)NHOQ^1$; —$C(O)NH$—$NHQ^1$; —$C(O)OQ^1$; —$(CH_2)OQ^1$ or —$(CH_2)NHQ^3$; —$(CH_2)_2NHQ^3$; —$(CH_2)NH$—$C(NHQ^3)$=$NQ^4$; —$(CH_2)_2NH$—$C(NHQ^3)$=$NQ^4$; —$(CH_2)NH$—$CH$=$NQ^3$; —$(CH_2)_2NH$—$CH$=$NQ^3$; —$C(NHQ^3)$=$NQ^4$, wherein $Q^1$, $Q^3$ and $Q^4$ are as described in the invention, preferably $Q^1$ represents H or methyl and $Q^3$ and $Q^4$ represents H; and $R^3$ represents $SO_3H$ or $CF_2COOH$, preferably $SO_3H$;

W represents a non-aromatic, unsaturated 5-membered heterocycle comprising a group N—$R^2$ and a group X, wherein $R^2$ is chosen among $(C(O))_w$—$C_1$-$C_3$-alkyl, $(C(O))_w$—$(CH_2)_v$—$C(O)OQ^5$, $(C(O))_w$—$(CH_2)_qNQ^5Q^6$, $(C(O))_w$—$(CH_2)_qOQ^5$, $(C(O))_w$—$(CH_2)_q$—$NHC(O)OQ^5$, wherein $Q^5$ and $Q^6$ are as defined above, preferably chosen among H or $C_1$-$C_4$-alkyl; q and v are as defined above and w is as defined above, preferably w is 0; and X is a heteroatom, preferably S, O or N, preferably S.

Preferably, in the compounds of the invention:

$R^1$ represents H;

$R^3$ represents $SO_3H$ or $CF_2COOH$, preferably $SO_3H$;

W represents a non-aromatic, unsaturated 5-membered heterocycle comprising a group N-$R^2$ and a group X, wherein $R^2$ is chosen among $(C(O))_w$—$C_1$-$C_3$-alkyl, $(C(O))_w$—$(CH_2)_v$—$C(O)OQ^5$, $(C(O))_w$—$(CH_2)_qNQ^5Q^6$, $(C(O))_w$—$(CH_2)_qOQ^5$, $(C(O))_w$—$(CH_2)_q$—$NHC(O)OQ^5$, wherein $Q^5$ and $Q^6$ are as defined above, preferably chosen among H or $C_1$-$C_4$-alkyl; q and v are as defined above and w is as defined above, preferably w is 0; and X is a heteroatom, preferably S, O or N, preferably S.

Preferably the compounds of the invention are compounds of formula (A) or (A*) wherein:

$R^1$ represents H;

$R^3$ represents $SO_3H$ or $CF_2COOH$, preferably $SO_3H$;

W represents a non-aromatic, unsaturated 5-membered heterocycle comprising a group N—$R^2$ and a group X, wherein $R^2$ is chosen among $(C(O))_w$—$C_1$-$C_3$-alkyl, $(C(O))_w$—$(CH_2)_v$—$C(O)OQ^5$, $(C(O))_w$—$(CH_2)_qNQ^5Q^6$, $(C(O))_w$—$(CH_2)_qOQ^5$, $(C(O))_w$—$(CH_2)_q$—$NHC(O)OQ^5$, wherein $Q^5$ and $Q^6$ are as defined above, preferably chosen among H or $C_1$-$C_4$-alkyl; q and v are as defined above and w is as defined above, preferably w is 0; and X is a heteroatom, preferably S, O or N, preferably S.

Preferably the compounds of the invention are compounds of formula (A2) or (A2*) wherein:

$R^1$ represents H;

$R^3$ represents $SO_3H$ or $CF_2COOH$, preferably $SO_3H$;

$R^2$ is chosen among $(C(O))$—$C_1$-$C_3$-alkyl, $(C(O))_w$—$(CH_2)_w$—$C(O)OQ^5$, $(C(O))_w$—$(CH_2)_qNQ^5Q^6$, $(C(O))_w$—$(CH_2)_qOQ^5$, $(C(O))_w$—$(CH_2)_q$—$NHC(O)OQ^5$, wherein $Q^5$ and $Q^6$ are as defined above, preferably chosen among H or $C_1$-$C_4$-alkyl; q and v are as defined above and w is as defined above, preferably w is 0; and X is a heteroatom, preferably S, O or N, preferably S.

It should be understood that for the compounds of the invention any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a $S(O)_2$ group;

any nitrogen atom present within a heterocycle or present within group wherein it is trisubstituted thus forming a tertiary amino group, can be further quaternized by a methyl group.

The invention relates also to compounds of formula

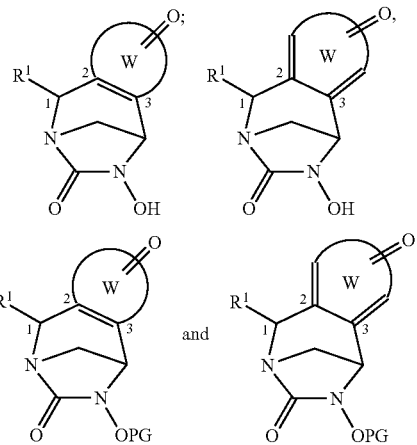

preferably of formula

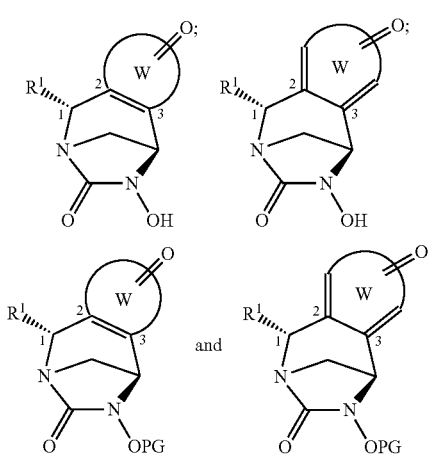

wherein $R^1$, W are as defined above and PG, is a protective group, for example chosen among allyl, benzyl, tertbutyldimethylsilyl (TBDMS), tert-butoxycarbonyl (Boc), etc. The compounds are especially intermediates compounds for the preparation of compounds of formula (I), (A), (B), (A1) to (A68), (B1) to (B8), (I*), (A*), (B*), (A1*) to (A68*), (B1*) to (B8*) according to the invention.

Preferably, the invention also relates to compounds of formula:

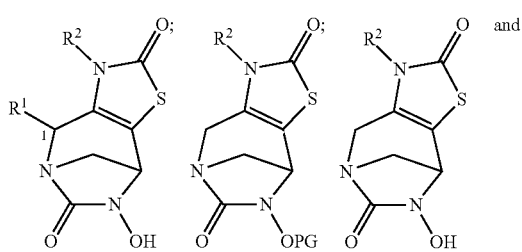

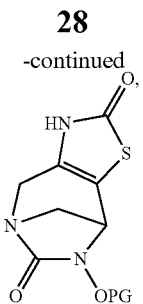

preferably

[structures]

wherein $R^1$ and $R^2$, are as defined above and PG, is a protective group, for example chosen among allyl, benzyl, tertbutyldimethylsilyl (TBDMS), tert-butoxycarbonyl (Boc), etc. The compounds are especially intermediates compounds for the preparation of compounds of formula (I), (A), (A2), (I*), (A*), (A2*) according to the invention.

The term "alkyl", as used herein, refers to an aliphatic-hydrocarbon group which may be straight or branched, having 1 to 3 carbon atoms in the chain unless specified otherwise. Preferred alkyl groups have 1 or 2 carbon atoms in the chain. Specific examples of alkyl groups include, but are not limited to, methyl, ethyl, n-propyl, iso propyl. Preferably, the alkyl group is methyl or ethyl.

The term "fluoroalkyl", as used herein, refers to an alkyl group substituted with at least one fluorine atom. The term "alkyl" is as defined above. Specific examples of fluoroalkyl groups include but are not limited to trifluoromethyl, difluoromethyl, fluoromethyl.

The term "cycloalkyl" refers to a saturated monocyclic or bicyclic non-aromatic hydrocarbon ring of 3 to 6 carbon atoms, preferably 3 to 4 carbon atoms, which can comprise one or more unsaturation. Specific examples of monocyclic cycloalkyl groups include cyclopropyl, cyclobutyl, cyclopentyl, cyclohexyl. Preferably, the cycloalkyl group is cyclopropyl or cyclobutyl.

The term "fluorocycloalkyl" refers to a cycloalkyl group substituted with at least one fluorine atom. The term "cycloalkyl" is as defined above. Specific examples of fluorocycloalkyl groups include fluorocyclopropyl, difluorocyclopropyl, fluorocyclobutyl, difluorocyclobutyl.

The term "heterocycle", as used herein and without contrary definition specifically mentioned, either alone or in combination with another radical, refers to a monocyclic saturated, partially or totally unsaturated or aromatic hydrocarbon radical, preferably to a 4- to 10-membered hydrocarbon radical, comprising at least one heteroatom, such as N, O, S, S(O) or S(O)$_2$. Preferably, the heterocycle is a monocyclic saturated, partially or totally unsaturated or aromatic hydrocarbon radical, preferably a 4- to 6-membered hydrocarbon radical, comprising at least one nitrogen atom and at least one further heteroatom, such as N, O, S, S(O) or S(O)$_2$. The carbon atoms of the heterocycle can also be oxidized to form a C(O) group. Suitable heterocycles are also disclosed in the Handbook of Chemistry and Physics, 76$^{th}$ Edition, CRC Press, Inc., 1995-1996, pages 2-25 to 2-26. Examplary heterocycle groups include, but are not limited to, azetidinyl, oxetanyl, oxazolyl, oxazolidinyl, oxadiazolyl, pyrrolyl, pyrrolidinyl, pyridyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, tetrahydropyranyl. Preferably, in the compounds according to the invention, the heterocycle is linked to the structure of the compounds by a carbon atom of the heterocycle (also said carbon-linked heteroatom).

Moreover some compounds according to this invention may contain a basic amino group and thus may form an inner zwitterionic salt (or zwitterion) with the acidic group (R$^3$)—OSO$_3$H, —OCFHCO$_2$H or —OCF$_2$CO$_2$H and such inner zwitterionic salts are also included in this invention.

The expression "optionally substituted" means "non-substituted or substituted by chemical groups that are further defined" or "unsubstituted or substituted chemical groups that are further defined".

The term "racemate" is employed herein to refer to an equal amount of two specific enantiomers.

The term "enantiomer" is employed herein to refer to one of the two specific stereoisomers which is a non-superimposable mirror image with one other but is related to one other by reflection.

The compounds according to the invention may include one or more asymmetric carbon atoms and may thus exist in the form of optical isomers as well as in the form of racemic or non-racemic mixtures thereof. The compounds according to the invention can be used as a single isomer or as a mixture of stereochemical isomeric forms. Diastereoisomers, i.e., non-superimposable stereochemical isomers can be separated by conventional means such as chromatography, distillation, crystallization or sublimation. The optical isomers (enantiomers) can be obtained by using optically active starting materials, by resolution of the racemic mixtures according to conventional processes, for example by formation of diastereoisomeric salts by treatment with an optically active acid or base or by using chiral chromatography column.

As used herein, the expression "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention can be synthesized from the parent compound which comprises a basic or an acidic moiety, by conventional chemical methods. Furthermore, the expression "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc, metal salts such as sodium, lithium, potassium, calcium, zinc or magnesium salts with organic bases such as dicyclohexylamine salts, N-methyl-D-glucamine. Lists of suitable salts may be found in Remington's Pharmaceutical Sciences, 17$^{th}$ ed., Mack Publishing Company, Easton, Pa., 1985, p. 1418, P. H. Stahl, C. G. Wermuth, Handbook of Pharmaceutical salts—Properties, Selection and Use, Wiley-VCH, 2002 and S. M. Berge et al. "Pharmaceutical Salts" J. Pharm. Sci, 66: p.1-19 (1977).

Compounds according to the invention also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described above and are not limited to $^2$H, $^3$H, $^{11}$C, $^{13}$C, $^{14}$C, $^{18}$F, $^{19}$F, $^{13}$N, $^{15}$N, $^{33}$S, $^{34}$S, $^{35}$S, $^{36}$S, $^{17}$O or $^{18}$O. Isotopically-labeled compounds are useful in drug and/or substrate tissue distribution studies. Substitution with heavier isotopes such as deuterium ($^2$H) affords greater metabolic stability (for example increased in vivo half-life or reduced dosage requirements). Isotopically-labeled compounds are prepared by any suitable method or by processes using an appropriate isotopically-labeled reagent in replacement of the non-labeled reagent otherwise employed.

The invention provides compounds having antibacterial properties and/or compounds acting as β-lactamase inhibitors.

The invention also provides a process for the preparation of a compound according to the invention. In particular the invention provides a process for the preparation of compound selected from compounds of formulae (I), (A), (B), (A1) to (A68), (B1) to (B8), (I*), (A*), (B*), (A1*) to (A68*) and (B1*) to (B8*) according to the invention.

A particular process according to the invention is represented in scheme 1, 2, 3, 4, 5 and 6.

Scheme 1

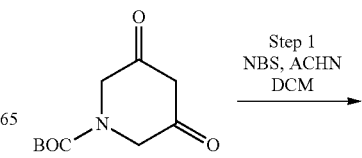

-continued

Step 2
1) H₂N-C(=S)-NH₂
2) TEA, MeOH

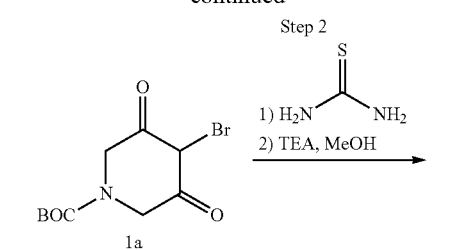
1a

Step 3
isoamyl nitrite
CuCl₂, ACN

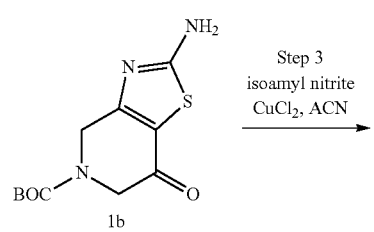
1b

Step 4
MeONa, MeOH

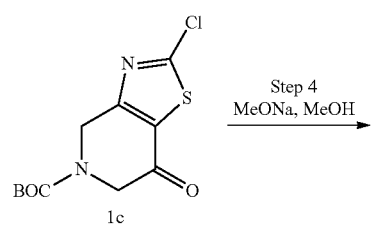
1c

Step 5
1) Pyridine, micro-waves
2) R²X

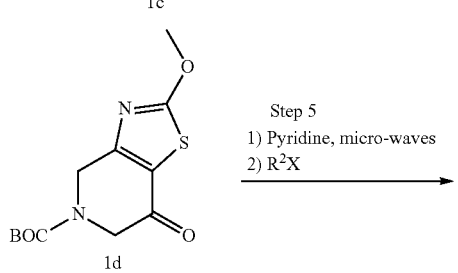
1d

Step 6
NaBH₄, MeOH

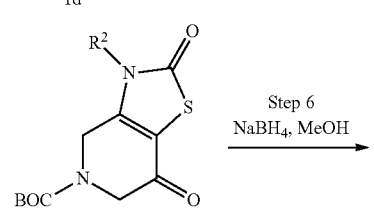

Step 7
DTA, PPh₃, Toluene

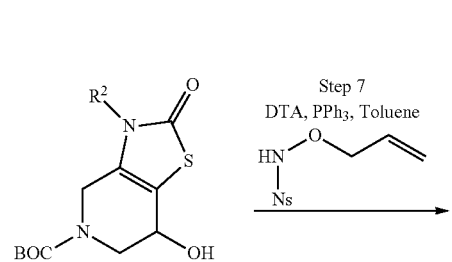

Step 8
Thiophenol, K₂CO₃
ACN

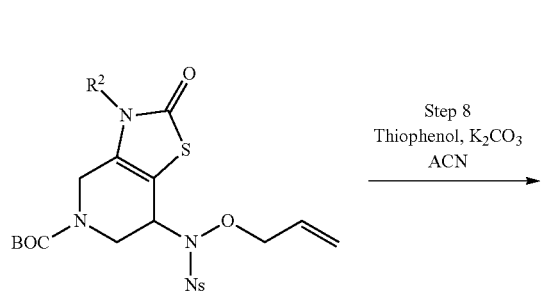

-continued

Step 9
TFA, DCM

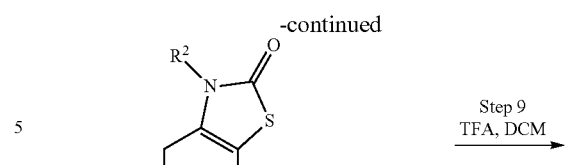

Step 10
TEA, ACN, diphosgene

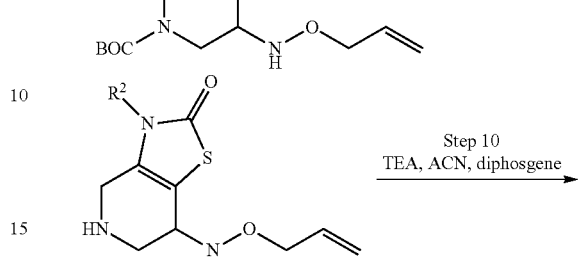

Step 11
Pd(PPh₃)₄, AcOH, DCM

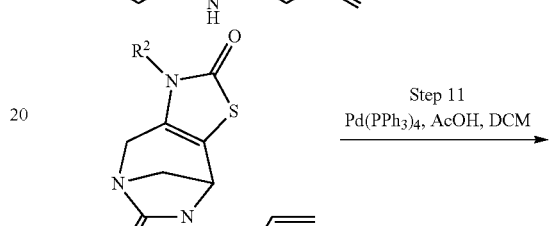

Step 12
1) Sulfur trioxide pyridine complex, pyridine
2) Ion exchange Dowex Na+

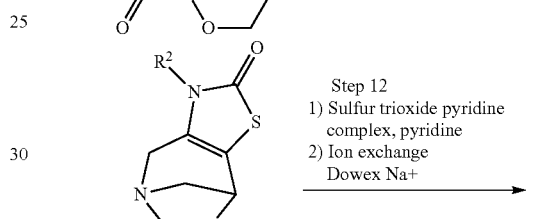

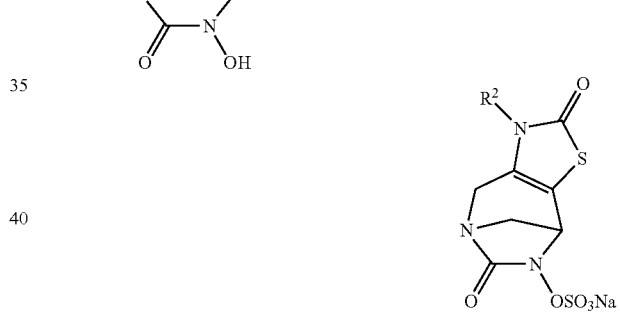

Scheme 2

Step 1
NaBH₄, MeOH

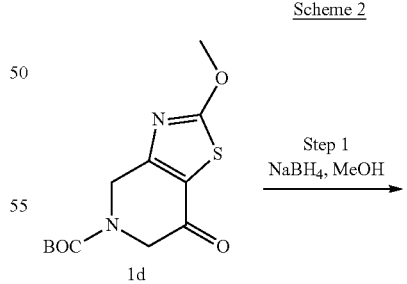
1d

Step 2
DTA, PPh₃, Toluene

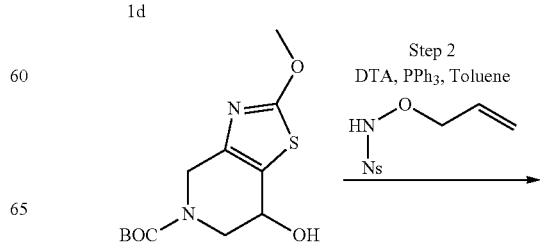

33
-continued
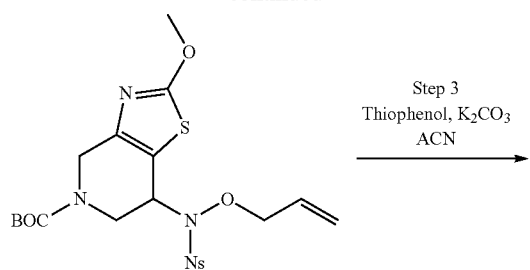
Step 3
Thiophenol, K$_2$CO$_3$
ACN
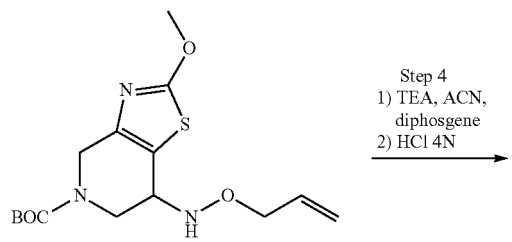
Step 4
1) TEA, ACN, diphosgene
2) HCl 4N
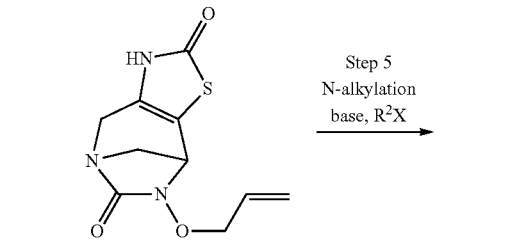
Step 5
N-alkylation
base, R$^2$X
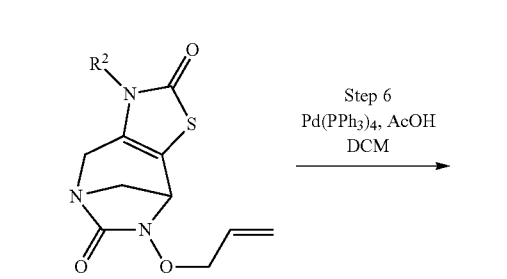
Step 6
Pd(PPh$_3$)$_4$, AcOH
DCM
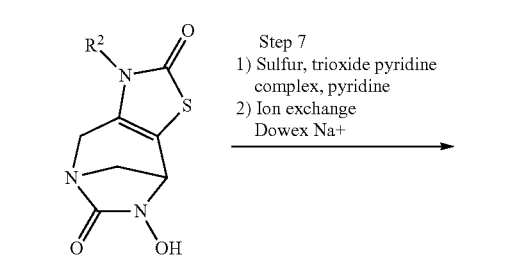
Step 7
1) Sulfur, trioxide pyridine complex, pyridine
2) Ion exchange Dowex Na+
34
Scheme 3
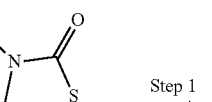
Step 1
protection
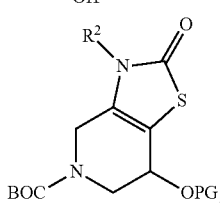
Step 2
deprotection
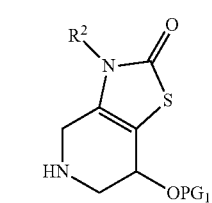
Step 3
1) NCS
2) base
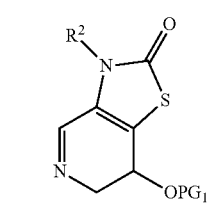
Step 4
TMSCN
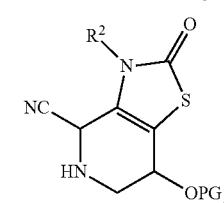
Step 5
protection
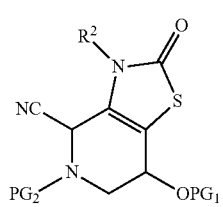
Step 6
deprotection
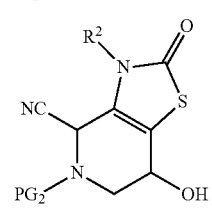
Step 7
1) MsO$_2$
2) NH$_2$OAll
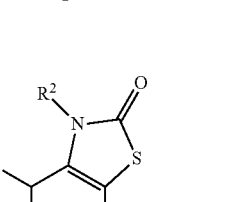
Step 8
1) TEA, ACN, diphosgene
2) acid 35 -continued

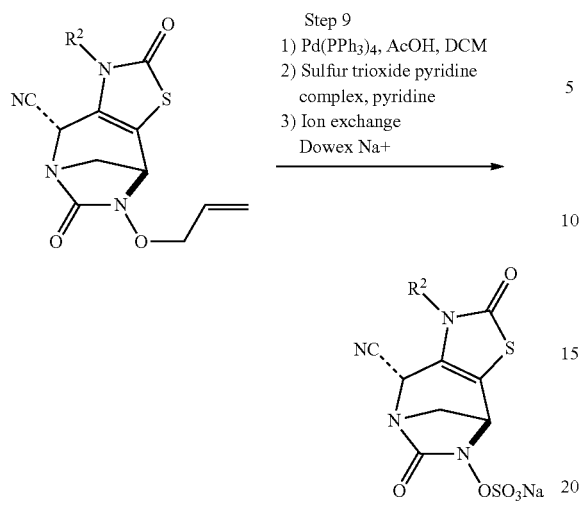

Step 9
1) Pd(PPh₃)₄, AcOH, DCM
2) Sulfur trioxide pyridine complex, pyridine
3) Ion exchange Dowex Na+

Scheme 4

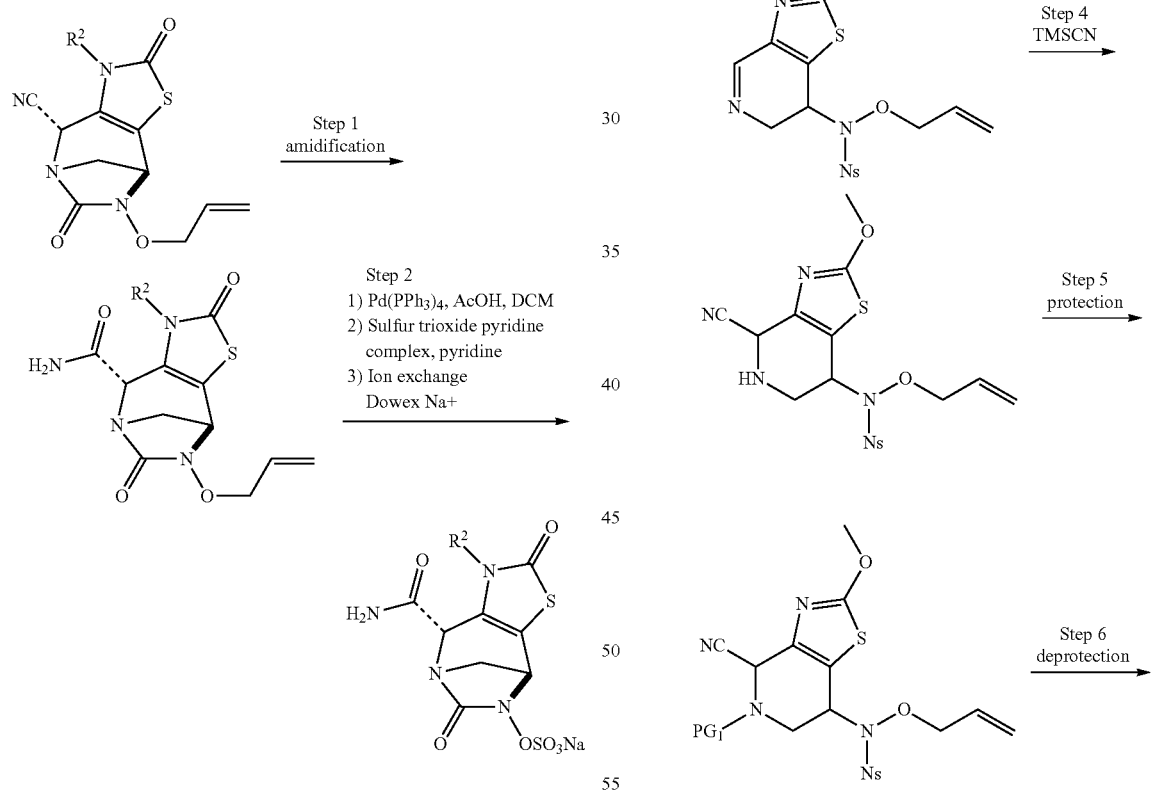

Step 1 amidification

Step 2
1) Pd(PPh₃)₄, AcOH, DCM
2) Sulfur trioxide pyridine complex, pyridine
3) Ion exchange Dowex Na+

Scheme 5

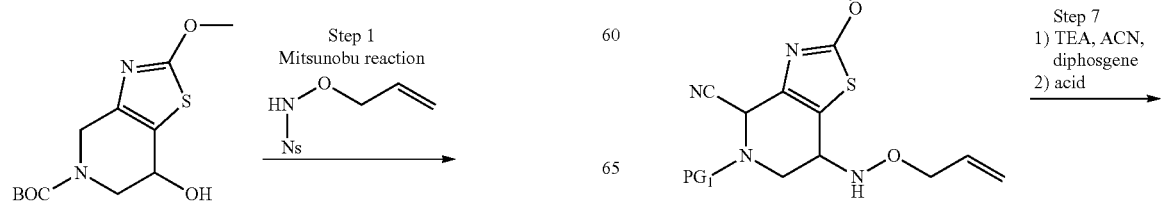

Step 1
Mitsunobu reaction

36 -continued

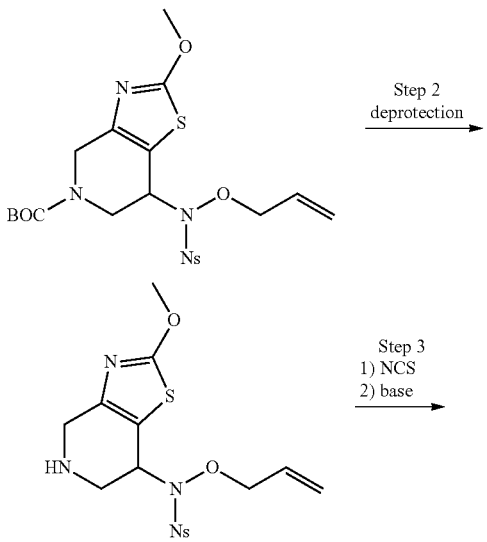

Step 2
deprotection

Step 3
1) NCS
2) base

Step 4
TMSCN

Step 5
protection

Step 6
deprotection

Step 7
1) TEA, ACN, diphosgene
2) acid

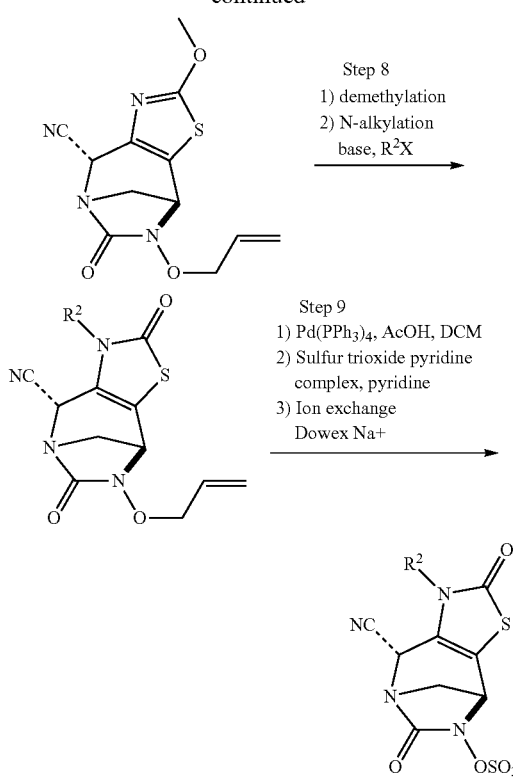
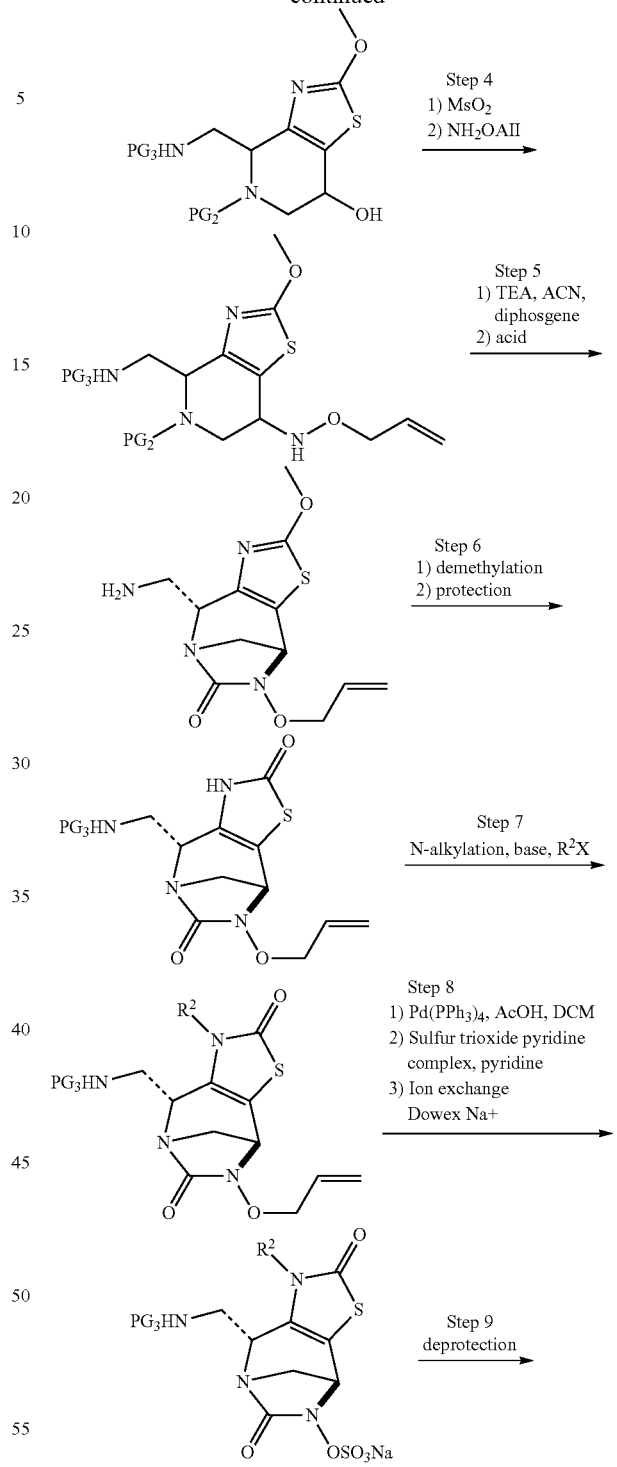
Scheme 6
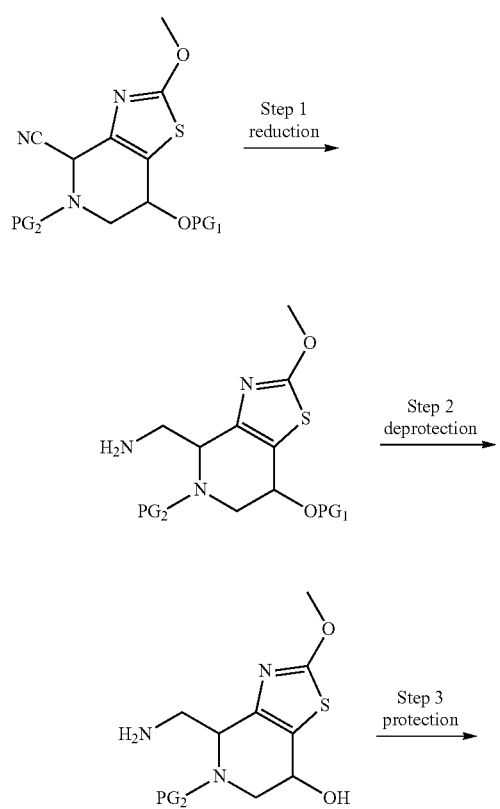
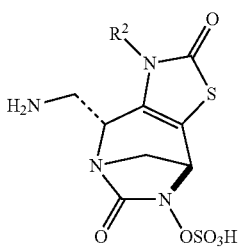

The processes of schemes 1-6 can be adapted for preparing further compounds according to the invention. Further processes for the preparation of compounds according to the invention can be derived from the process of scheme 1.

The invention also provides the use of the compounds according to the invention in the control of bacteria. The compound according to the invention is then usually used in combination with at least one pharmaceutically acceptable excipient.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also provides a composition, preferably a pharmaceutical composition, comprising at least one compound according to the invention in mixture with a pharmaceutically acceptable excipient. The composition according to the invention may thus comprise at least one compound selected from compounds of formulae (I), (A), (B), (A1) to (A68), (B1) to (B8), (I*), (A*), (B*), (A1*) to (A68*) and (B1*) to (B8*) in mixture with a pharmaceutically acceptable excipient.

The term "pharmaceutically acceptable carrier" or "pharmaceutically acceptable excipient" is employed for any excipient, solvent, dispersion medium, absorption retardant, diluent or adjuvant etc., such as preserving or antioxidant agents, fillers, binders, disintegrating agents, wetting agents, emulsifying agents, suspending agents, solvents, dispersion media, coatings, antibacterial agents, isotonic and absorption delaying agents and the like, that does not produce a secondary reaction, for example an allergic reaction, in humans or animals. Typical, non-limiting examples of excipients include mannitol, lactose, magnesium stearate, sodium saccharide, talcum, cellulose, sodium croscarmellose, glucose, gelatin, starch, lactose, dicalcium phosphate, sucrose, kaolin, magnesium carbonate, wetting agents, emulsifying agents, solubilizing agents, sterile water, saline, pH buffers, non-ionic surfactants, lubricants, stabilizing agents, binding agents and edible oils such as peanut oil, sesame oils and the like. In addition, various excipients commonly used in the art may be included. Pharmaceutically acceptable carriers or excipients are well known to a person skilled in the art, and include those described in Remington's Pharmaceutical Sciences (Mack Publishing Company, Easton, USA, 1985), Merck Index (Merck & Company, Rahway, N.J.), Gilman et al (Eds. The pharmacological basis of therapeutics, $8^{th}$ Ed., Pergamon press., 1990). Except insofar as any conventional media or adjuvant is incompatible with the active ingredient according to the invention, its use in the therapeutic compositions is contemplated.

The expression "antibacterial agent" as used herein, refers to any substance, compound or their combination capable of inhibiting, reducing or preventing growth of bacteria, inhibiting or reducing ability of bacteria to produce infection in a subject, or inhibiting or reducing ability of bacteria to multiply or remain infective in the environment, or decreasing infectivity or virulence of bacteria.

The antibacterial agent can be selected among the following families: aminoglycosides, beta-lactams, glycylcyclines, tetracyclines, quinolones, fluoroquinolones, glycopeptides, lipopeptides, macrolides, ketolides, lincosamides, streptogramins, oxazolidinones and polymyxins alone or in mixture. Preferably, the further antibacterial agent is selected among the beta-lactam families, and more preferably among penicillin, cephalosporins, penems, carbapenems and monobactam, alone or in mixture.

Among the penicillin the antibacterial agent is preferably selected in the group consisting of amoxicillin, ampicillin, azlocillin, mezocillin, apalcillin, hetacillin, bacampicillin, carbenicillin, sulbenicillin, temocillin, ticarcillin, piperacillin, mecillinam, pivmecillinam, methicillin, ciclacillin, talampacillin, aspoxicillin, oxacillin, cloxacillin, dicloxacillin, flucloxacillin, nafcillin, and pivampicillin, alone or in mixture.

Among the cephalosporin, the antibacterial agent is preferably selected in the group consisting of cefatriazine, cefazolin, cefoxitin, cephalexin, cephradine, ceftizoxime, cephacetrile, cefbuperazone, cefprozil, ceftobiprole, ceftobiprole medocaril, ceftaroline, ceftaroline fosaminyl, cefalonium, cefminox, ceforanide, cefotetan, ceftibuten, cefcapene pivoxil, cefditoren pivoxil, cefdaloxime cefroxadine, ceftolozane and S-649266, cephalothin, cephaloridine, cefaclor, cefadroxil, cefamandole, cefazolin, cephalexin, cephradine, ceftizoxime, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidine, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbef, and latamoxef, alone or in mixture. Among the carbapenem, the antibacterial agent is preferably selected in the group consisting of imipenem, doripenem, meropenem, biapenem, ertapenem and panipenem, alone or in mixture.

Among the monobactam, the antibacterial agent is preferably selected in the group consisting of aztreonam, tigemonam, carumonam, BAL30072 and nocardicin A, alone or in mixture.

The present invention also relates to a composition comprising at least a compound of formulae (I), (A), (B), (A1) to (A68), (B1) to (B8), (I*), (A*), (B*), (A1*) to (A68*), (B1*) to (B8*) according to the invention and ceftazidime.

The present invention also provides a kit comprising:
  a pharmaceutical composition according to the invention, and
  at least one other composition comprising one or more antibacterial agents, preferably at least one of these antibacterial agents is a beta-lactam.

The two compositions can each be prepared separately with one specific pharmaceutically acceptable carrier, and can then be mixed, especially extemporaneously.

The present invention also relates to a kit comprising:
  a pharmaceutical composition comprising at least a compound of formulae (I), (A), (B), (A1) to (A68), (B1) to (B8), (I*), (A*), (B*), (A1*) to (A68*), (B1*) to (B8*) according to the invention; and
  a pharmaceutical composition comprising ceftazidime.

The present invention also refers to a compound selected within the compounds of formulae (I), (A), (B), (A1) to (A68), (B1) to (B8), (I*), (A*), (B*), (A1*) to (A68*) and (B1*) to (B8*) according to the invention for its use as a medicine.

The present invention also refers to a compound selected within the compounds of formulae (I), (A), (B), (A1) to (A68), (B1) to (B8), (I*), (A*), (B*), (A1*) to (A68*) and (B1*) to (B8*) according to the invention for its use for the preparation of a medicine.

The present invention also refers to a compound selected within the compounds of formulae (I), (A), (B), (A1) to (A68), (B1) to (B8), (I*), (A*), (B*), (A1*) to (A68*) and (B1*) to (B8*) according to the invention for its use as an antibacterial agent.

The present invention also refers to the use of a compound selected within the compounds of formulae (I), (A), (B), (A1) to (A68), (B1) to (B8), (I*), (A*), (B*), (A1*) to (A68*) and (B1*) to (B8*) according to the invention or to the use of a pharmaceutical composition according to the invention for the preparation of an antibacterial agent comprising medicine.

The present invention also refers to the use of a compound selected within the compounds of formulae (I), (A), (B), (A1) to (A68), (B1) to (B8), (I*), (A*), (B*), (A1*) to (A68*) and (B1*) to (B8*) according to the invention or to the use of a pharmaceutical composition according to the invention for the preparation of a beta-lactamase inhibitor comprising medicine.

The present invention also refers to the use of a compound selected within the compounds of formulae (I), (A), (B), (A1) to (A68), (B1) to (B8), (I*), (A*), (B*), (A1*) to (A68*) and (B1*) to (B8*) according to the invention or to the use of a pharmaceutical composition according to the invention for the preparation of a medicine comprising an antibacterial agent and a beta-lactamase inhibitor.

The present invention also refers to the use of a compound selected within the compounds of formulae (I), (A), (B), (A1) to (A68), (B1) to (B8), (I*), (A*), (B*), (A1*) to (A68*) and (B1*) to (B8*) according to the invention or to the use of a pharmaceutical composition according to the invention or to the use of a kit according to the invention for the treatment or for the prevention of at least one bacterial infection.

The present invention also refers to the use of a compound selected within the compounds of formulae (I), (A), (B), (A1) to (A68), (B1) to (B8), (I*), (A*), (B*), (A1*) to (A68*) and (B1*) to (B8*) according to the invention or to the use of a pharmaceutical composition according to the invention or to the use of a kit according to the invention for the preparation of a medicine useful in the treatment or in the prevention of at least one bacterial infection.

The terms "prevention", "prevent" and "preventing" as used herein are intended to mean the administration of a compound or composition according to the invention in order to prevent infection by bacteria or to prevent occurrence of related infection and/or diseases. The terms "prevention", "prevent" and "preventing" also encompass the administration of a compound or composition according to the present invention in order preventing at least one bacterial infection, by administration to a patient susceptible to be infected, or otherwise at a risk of being infected by this bacteria.

The terms "treatment", "treat" and "treating" as used herein are intended to mean in particular the administration of a treatment comprising a compound or composition according to the invention to a patient suffering from an infection. The terms "treatment", "treat" and "treating" as used herein, also refer to administering a compound or composition according to the invention, optionally in combination with one or more further antibacterial agent, in order:

to reduce or to eliminate either bacterial infection or one or more symptoms associated with a bacterial infection, or to retard the progression of a bacterial infection or of one or more symptoms associated with a bacterial infection, or to reduce the severity of a bacterial infection or of one or more symptoms associated with a bacterial infection, or to suppress the clinical manifestation of a bacterial infection, or to suppress the manifestation of adverse symptoms caused by a bacterial infection.

The expression "infection" or "bacterial infection" as used herein, include the presence of bacteria, in or on a subject, which, if its growth were inhibited, would result in a benefit to the subject. As such, the term "infection" or "bacterial infection" in addition to referring to the presence of bacteria also refer to normal flora, which is not desirable. The term "infection" includes infection caused by bacteria. Examples of such bacterial infections are urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, chlamydia, skin infections, bacteremia.

The term "growth" as used herein, refers to the growth of one or more microorganisms and includes reproduction or population expansion of a microorganism, such as bacteria. The term also includes maintenance of on-going metabolic processes of a microorganism, including processes that keep the microorganism alive.

According to the invention, bacteria are chosen amongst gram-positive bacteria or gram-negative bacteria, preferably gram-negative bacteria. According to the invention, bacteria can be also chosen among bacteria producing "beta-lactamase" or "β-lactamase". These bacteria are well known by the person skilled in the art. The term "beta-lactamase" or "β-lactamase" as used herein, refers to any enzyme or protein or any other substance that is able to break down a beta-lactam ring. The term "beta-lactamase" or "β-lactamase" includes enzymes that are produced by bacteria and that have the ability to hydrolyze, either partially or completely, the beta-lactam ring present in a compound such as an antibacterial agent.

Among the gram-positive bacteria, the bacteria according to the invention is preferably chosen among *Staphylococcus*, *Streptococcus*, *Staphylococcus* species (including *Staphylococcus aureus*, *Staphylococcus epidermidis*), *Streptococcus* species (including *Streptococcus pneumonia*, *Streptococcus agalactiae*), *Enterococcus* species (including *Enterococcus faecalis* and *Enterococcus faecium*).

Among the gram-negative bacteria, the bacteria according to the invention is preferably chosen among *Acinetobacter* species (including *Acinetobacter baumannii*), *Citrobacter* species, *Escherichia* species (including *Escherichia coli*), *Haemophilus influenza*, *Morganella morganii*, *Klebsiella* species (including *Klebsiella pneumonia*), *Enterobacter* species (including *Enterobacter cloacae*), *Neisseria gonorrhoeae*, *Burkholderia* species (including *Burkholderia cepacia*), (*Proteus* species (including *Proteus mirabilis*), *Serratia* species (including *Serratia marcescens*), *Pseudomonas aeruginosa*.

The invention thus preferably refers to a compound selected within the compounds of formulae (I), (A), (B), (A1) to (A68), (B1) to (B8), (I*), (A*), (B*), (A1*) to (A68*) and (B1*) to (B8*) according to the invention or to a pharmaceutical composition according to the invention or to a kit according to the invention for its use for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to the use of a compound selected within the compounds of formulae (I), (A), (B), (A1) to (A68), (B1) to (B8), (I*), (A*), (B*), (A1*) to (A68*) and (B1*) to (B8*) according to the invention or to a pharmaceutical composition according to the invention for the preparation of a medicine for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to a kit according to the invention, for its simultaneous, separated or sequential administration to a patient in need thereof in the treatment or in the prevention of bacterial infections, preferably caused by bacteria producing one or more beta-lactamases. Preferably, the bacteria are chosen amongst gram-positive bacteria or gram-negative bacteria, more preferably gram-negative bacteria.

The present invention also refers to a compound selected within the compounds of formulae (I), (A), (B), (A1) to (A68), (B1) to (B8), (I*), (A*), (B*), (A1*) to (A68*) and (B1*) to (B8*) according to the invention for its use in combination with one or more further antibacterial agents, preferably at least one of the further antibacterial agents being a beta lactam compound, for the treatment or for the prevention of bacterial infections, preferably caused by bacteria producing one or more beta-lactamases. Preferably, the bacteria are chosen amongst gram-positive bacteria or gram-negative bacteria, more preferably gram-negative bacteria, and wherein a compound selected within the compounds of formulae (I), (A), (B), (A1) to (A68), (B1) to (B8), (I*), (A*), (B*), (A1*) to (A68*) and (B1*) to (B8*) according to the invention and the further antibacterial agent are administered simultaneously, separately or sequentially.

The present invention also refers to the use of a compound selected within the compounds of formulae (I), (A), (B), (A1) to (A68), (B1) to (B8), (I*), (A*), (B*), (A1*) to (A68*) and (B1*) to (B8*) according to the invention or of a pharmaceutical composition according to the invention or of a kit according to the invention for the prevention or for the treatment of bacterial infections, preferably of a bacterial infection, preferably caused by bacteria producing one or more beta-lactamases. Preferably, the bacteria are chosen amongst gram-positive bacteria or gram-negative bacteria, more preferably gram-negative bacteria.

The present invention also relates to a method for the treatment or prevention of bacterial infections, preferably caused by bacteria producing one or more beta-lactamases comprising the administration of a therapeutically effective amount of a compound selected within the compounds of formulae (I), (A), (B), (A1) to (A68), (B1) to (B8), (I*), (A*), (B*), (A1*) to (A68*) and (B1*) to (B8*) according to the invention, or of a pharmaceutical composition according to the invention or of a kit according to the invention to a patient in need thereof. Preferably, the bacteria are chosen amongst gram-positive bacteria or gram-negative bacteria, more preferably gram-negative bacteria.

The term "patient" means a person or an animal at risk of being infected by bacteria or, a person or an animal being infected by bacteria, preferably by gram-positive and by gram-negative bacteria, more preferably by gram-negative bacteria. As used herein, the term "patient" refers to a warm-blooded person or animal such as a mammal, preferably a human or a human child, who is afflicted with, or has the potential to be afflicted with one or more infections and conditions described herein. The identification of those subjects who are in need of treatment of herein-described diseases and conditions is well within the ability and knowledge of one skilled in the art. A veterinarian or a physician skilled in the art can readily identify, by the use of clinical tests, physical examination, medical or family history or biological and diagnostic tests, those subjects who are in need of such a treatment.

The expression "therapeutically effective amount" or "pharmaceutically effective amount" as used herein, refer to an amount of a compound according to the invention, which when administered to a patient in need thereof, is sufficient to effect treatment for disease-states, conditions, or disorders for which the compound has utility. Such an amount would be sufficient to elicit the biological or medical response of a tissue system, or patient that is sought by a researcher or a clinician. The amount of a compound according to the invention which constitutes a "therapeutically effective amount" will vary, notably depending on the compound itself and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a "therapeutically effective amount" can be determined by one of ordinary skilled in the art having regard to its own knowledge, and this disclosure. Preferably, the compound according to the invention is administered in an amount comprised between 0.1 to 30 g per day.

The compound according to the invention may be provided in an aqueous physiological buffer solution for parenteral administration. The compound of the present invention is also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described herein. The compound provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The pharmaceutical composition may be conveniently administered in unit dosage form and may be prepared by any method well-known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Preferred formulations include pharmaceutical compositions wherein a compound according to the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth;

a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate or talc in any combination.

Liquid preparations for parenteral administration include sterile aqueous or non-aqueous solutions, suspensions and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compound. Intravenous vehicles can include fluid and nutrient replenishers, electrolyte replenishers, such as those based on Ringer's dextrose, and the like. Other potentially useful parenteral delivery systems for the active compound include ethylene-vinyl acetate copolymer particles, osmotic pumps, implantable infusion systems and liposomes.

Alternative modes of administration include formulations for inhalation, which include such means as dry powder, aerosol, or drops. They may be aqueous solutions comprising, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations.

Formulations suitable for transdermal administration can be presented as discrete patches and can be lipophilic emulsions or buffered, aqueous solutions, dissolved and/or dispersed in a polymer or an adhesive.

The invention is further illustrated but not restricted by the description of the following examples.

EXAMPLES

The following examples are provided for the purpose of illustrating the present invention and by no means should be interpreted to limit the scope of the present invention.

The first part represents the preparation of the compounds according to the invention (intermediates and final compounds) whereas the second part describes the evaluation of antibacterial activity of compounds according to the invention.

Preparation of the Compounds and Biological Activity:
Abbreviations or symbols used herein include:
ACHN: 1,1'-azobis(cyclohexanecarbonitrile)
ACN: acetonitrile
AcOH: acetic acid
Bn: benzyl
Boc: tert-butoxycarbonyl
$Boc_2O$: tert-butoxycarbonyl anhydride
BocON: [2-(tert-butoxycarbonyloxyimino)-2-phenylacetonitrile]
bs: broad singlet
Burgess reagent: methyl N-(triethylammoniosulfonyl)carbamate
CFU: colony-forming units
CLSI: clinical laboratory standards institute
d: doublet
DBU: 1,8-diazabicyclo[5.4.0]undec-7-ene
DCM: dichloromethane
dd: doublet of doublet
ddd: doublet of doublet of doublet
ddt: doublet of doublet of triplet
dq: doublet of quartet
dt: doublet of triplet
DTA: di-tert-butylazodicarboxylate
DEAD: diethyl azodicarboxylate
Dess-Martin periodinane: 1,1,1-tris(acetyloxy)-1,1-dihydro-1,2-benziodoxol-3-(1H)-one
DIAD: diisopropyl azodicarboxylate
DIPEA: N,N-diisopropylethylamine
DMAP: 4-dimethylaminopyridine
DMF: N,N-dimethylformamide
DMSO: dimethylsulfoxide
EtOAc: ethyl acetate
$Et_2O$: diethyl ether
h: hours
HATU: 1-[Bis(dimethylamino)methylene]-1H-1,2,3-triazolo[4,5-b]pyridinium-3-oxid hexafluorophosphate
m: multiplet
min: minutes
MeOH: methanol
MeONa: sodium methoxide
MIC: minimum inhibitory concentration
MS: mass spectrometry
MsCl: methanesulfonyl chloride
NBS: N-bromosuccinimide
NMR: nuclear magnetic resonance spectroscopy
Ns: nosyl, nitrobenzenesulfonyl
$Pd(Ph_3)_4$: tetrakis(triphenylphosphine)palladium(0)
PG: protective group
PhSH: thiophenol
$PMe_3$: trimethylphosphine
$PPh_3$: triphenylphosphine
Ppm: parts per million
q: quartet
rt: room temperature
s: singlet
SEM: [2-(trimethylsilyl)ethoxy]methyl
t: triplet
td: triplet of doublet
TBAF: tetra-n-butylammonium fluoride
TBDMSOTf: trifluoromethanesulfonic acid tert-butyldimethylsilyl ester TBSOTf: trimethylsilyl trifluoromethanesulfonate
tBuOK: potassium tert-butoxide
TEA: trimethylamine
TFA: trifluoroacetic acid
THF: tetrahydrofuran
THP: tetrahydropyranyl
TLC: thin layer chromatography
TMSI: Iodotrimethylsilane
Tr: trityl (triphenylmethyl)
Example 1
Synthesis of Sodium (5-methyl-4,9-dioxo-3-thia-5,8,10-triaza tricyclo[6.2.1.0$^{2,6}$]undec-2(6)-en-10-yl) sulfate
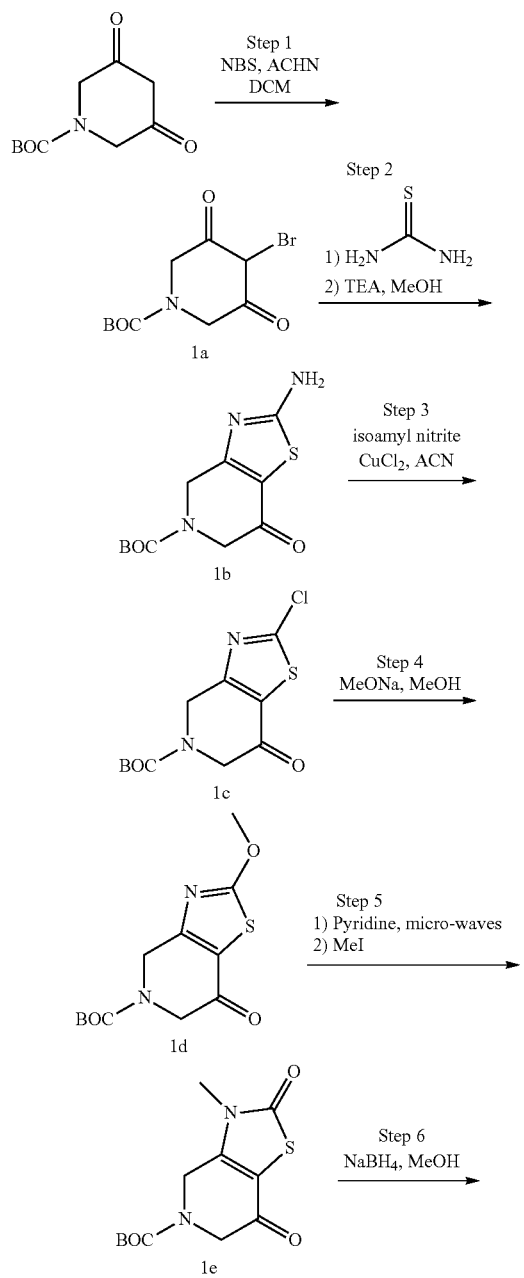
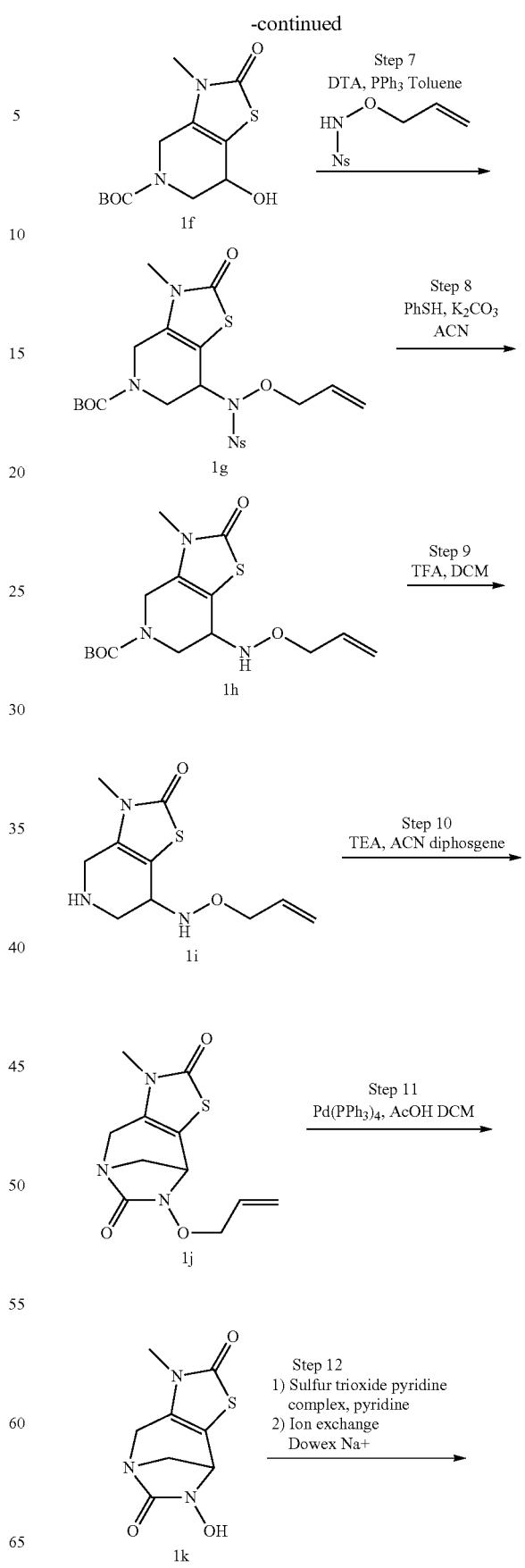

-continued

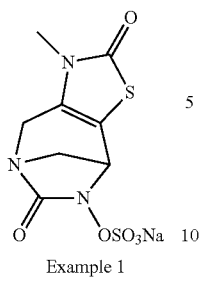

Example 1

Step 1: Preparation of Intermediate tert-butyl 4-bromo-3,5-dioxo-piperidine-1-carboxylate (1a)

To a solution of tert-butyl 3,5-dioxopiperidine-1-carboxylate (3 g, 14.07 mmol) in anhydrous DCM (60 mL) under inert atmosphere at 0° C. was successively added NBS (2.5 g, 14.07 mmol) and ACHN (0.223 g, 0.91 mmol). The reaction mixture was stirred 2 h at 0° C. The solution was washed with water, then with NaCl aqueous solution. The organic layer was dried over $Na_2SO_4$ and evaporated in vacuo to give tert-butyl 4-bromo-3,5-dioxo-piperidine-1-carboxylate (1a) (4.11 g, 14.07 mmol, quantitative yield) as an off-white solid.

MS m/z ([M+H-tertbutyl]$^+$) 236/238.
MS m/z ([M−H]$^−$) 290/292.
$^1$H NMR (400 MHz, $CDCl_3$): δ(ppm) 1.48 (s, 9H), 4.35 (bs, 4H).

Step 2: Preparation of Intermediate tert-butyl 2-amino-7-oxo-6,7-dihydro-4H-thiazolo[4,5-c]pyridine-5-carboxylate (1b)

To a solution of tert-butyl 4-bromo-3,5-dioxo-piperidine-1-carboxylate (1a) (0.500 g, 1.71 mmol) in anhydrous MeOH (8 mL) under inert atmosphere was added thiourea (0.226 g, 3.42 mmol). After stirring 30 min at rt, TEA (0.477 mL, 3.42 mmol) was added and the mixture was refluxed 5 h. MeOH was evaporated and the residue was solubilized with EtOAc. The solution was washed with water, 10% of $Na_2CO_3$ aqueous solution and NaCl aqueous solution. The organic phase was dried over $Na_2SO_4$, filtered and evaporated. The solid was triturated with cyclohexane and filtered to give tert-butyl 2-amino-7-oxo-6,7-dihydro-4H-thiazolo[4,5-c]pyridine-5-carboxylate (1b) (0.350 g, 1.30 mmol, 76%) as an off white solid.

MS m/z ([M+H]$^+$) 270.
MS m/z ([M−H]$^{31}$) 268.
$^1$H NMR (400 MHz, $CDCl_3$): δ(ppm) 1.48 (s, 9H), 4.23 (s, 2H), 4.66 (s, 2H), 5.77 (bs, 2H).

Step 3: Preparation of Intermediate tert-butyl 2-chloro-7-oxo-4,6-dihydrothiazolo[4,5-c]pyridine-5-carboxylate (1c)

To a solution of tert-butyl 2-amino-7-oxo-6,7-dihydro-4H-thiazolo[4,5-c]pyridine-5-carboxylate (1b) (0.473 g, 1.76 mmol) in anhydrous ACN (33 mL) under inert atmosphere at −20° C. was added isoamyl nitrite (0.710 mL, 5.27 mmol). After 10 min at −20° C., Copper(11) chloride (0.473 g, 3.52 mmol) was added. The mixture was stirred for 1 h at −20° C., then 4 h at rt. The solution was extracted with DCM, washed with 10% of $Na_2CO_3$ aqueous solution and the organic phase was dried over $Na_2SO_4$, filtered and evaporated. The product was purified by flash chromatography on silica gel (DCM/EtOAc 98/2) to give tert-butyl 2-chloro-7-oxo-4,6-dihydrothiazolo[4,5-c]pyridine-5-carboxylate (1c) (0.458 g, 1.59 mmol, 90%) as an off-white solid.

MS m/z ([M+H-tertbutyl]$^+$) 233/235.
MS m/z ([M−H]$^−$) 287/289.
$^1$H NMR (400 MHz, $CDCl_3$): δ(ppm) 1.48 (s, 9H), 4.31 (s, 2H), 4.83 (s, 2H).

Step 4: Preparation of Intermediate tert-butyl 2-methoxy-7-oxo-6,7-dihydro-4H-thiazolo[4,5-c]pyridine-5-carboxylate (1d)

To a solution of tert-butyl 2-chloro-7-oxo-4,6-dihydrothiazolo[4,5-c]pyridine-5-carboxylate (1c) (3.75 g, 12.98 mmol) in anhydrous MeOH (97 mL) under inert atmosphere at −78° C. was added dropwise a MeONa solution 0.5M (28.6 mL, 14.30 mmol). The reaction mixture was stirred for 15 min at −78° C., then for 30 min at rt. MeOH was removed under vacuum and the resulting residue was diluted with DCM and filtered on a mixture of silica gel and celite. The product was eluted with DCM/EtOAc 8/2, concentrated in vacuo and purified by flash chromatography on silica gel (cyclohexane/EtOAc 90/10 to 80/20) to provide tert-butyl 2-methoxy-7-oxo-6,7-dihydro-4H-thiazolo[4,5-c]pyridine-5-carboxylate (1d) (2.23 g, 7.84 mmol, 60%) as a yellow solid.

MS m/z ([M+H]$^+$) 285.
$^1$H NMR (400 MHz, $CDCl_3$): δ(ppm) 1.49 (s, 9H), 4.17 (s, 3H), 4.26 (s, 2H), 4.70 (s, 2H).

Step 5: Preparation of Intermediate tert-butyl 3-methyl-2,7-dioxo-2,3,6,7-tetrahydro-4H-thiazolo[4,5-c]pyridine-5-carboxylate (1e)

Tert-butyl 2-methoxy-7-oxo-6,7-dihydro-4H-thiazolo[4,5-c]pyridine-5-carboxylate (1d) (1.92 g, 6.74 mmol) was solubilized in pyridine (1.1 mL, 13.49 mmol) and warmed 30 min at 90° C. under microwave irradiation. The mixture was evaporated and the residue was diluted with DCM (57 mL) at 0° C. A solution of MeI (0.840 mL, 13.49 mmol) in DCM (15 mL) was added dropwise to the reaction mixture. After stirring 1 h at 0° C. and 2 h at rt, the precipitate was filtered. The filtrate was evaporated, solubilized in EtOAc and filtrated on silica gel cake to provide tert-butyl 3-methyl-2,7-dioxo-2,3,6,7-tetrahydro-4H-thiazolo[4,5-c]pyridine-5-carboxylate (1e) (1.63 g, 5.72 mmol, 85%).

MS m/z ([M+H]$^+$) 285.
MS m/z ([M−H]$^−$) 283.
$^1$H NMR (400 MHz, $CDCl_3$): δ(ppm) 1.49 (s, 9H), 3.36 (s, 3H), 4.26 (s, 2H), 4.61 (s, 2H).

Step 6: Preparation of Intermediate tert-butyl 7-hydroxy-3-methyl-2-oxo-2,3,6,7-tetrahydro-4H-thiazolo[4,5-c]pyridine-5-carboxylate (1f)

To a solution of tert-butyl 3-methyl-2,7-dioxo-2,3,6,7-tetrahydro-4H-thiazolo[4,5-c]pyridine-5-carboxylate (1e) (1.78 g, 6.25 mmol) in anhydrous MeOH (62 mL) at 0° C. under inert atmosphere was added sodium borohydride (0.236 g, 6.25 mmol) by portions. The reaction mixture was stirred for 1 h and then concentrated under vacuum. The residue was diluted with EtOAc and filtered on silica gel cake to provide tert-butyl 7-hydroxy-3-methyl-2-oxo-2,3,6, 7-tetrahydro-4H-thiazolo[4,5-c]pyridine-5-carboxylate (1f) (1.56 g, 5.45 mmol, 87%) as a yellow solid.

MS m/z ([M+H]$^+$) 287.

¹H NMR (400 MHz, CDCl₃): δ(ppm) 1.50 (s, 9H), 3.22 (s, 3H), 3.55 (dd, J=3.0/13.6 Hz, 1H), 3.97-4.01 (m, 1H), 4.04 (bs, 1H), 4.52 (bs, 2H).

Step 7: Preparation of Intermediate tert-butyl 7-[allyloxy-(2-nitro-benzenesulfonyl)-amino]-3-methyl-2-oxo-2,3,6,7-tetrahydro-4H-thiazolo[4,5-c]pyridine-5-carboxylate (1g)

To a solution of tert-butyl 7-hydroxy-3-methyl-2-oxo-2,3,6,7-tetrahydro-4H-thiazolo[4,5-c]pyridine-5-carboxylate (1f) (1.56 g, 5.45 mmol) in anhydrous toluene (60 mL) under inert atmosphere was added N-allyloxy-2-nitro-benzenesulfonamide (1.41 g, 5.45 mmol) and Ph₃P (1.43 g, 5.45 mmol). DTA (1.42 g, 6.16 mmol) was added by portion and the mixture was stirred for 4 h at rt. The solution was filtered and concentrated under vacuum. The residue was purified by flash chromatography on silica gel (DCM/cyclohexane 70/30 to DCM/MeOH 99/1) to give tert-butyl 7-[allyloxy-(2-nitro-benzenesulfonyl)-amino]-3-methyl-2-oxo-2,3,6,7-tetrahydro-4H-thiazolo[4,5-c]pyridine-5-carboxylate (1g) (2.39 g, 4.53 mmol, 83%) as a yellow solid.

MS m/z ([M+H]⁺) 527.

Step 8: Preparation of Intermediate tert-butyl 7-allyloxyamino-3-methyl-2-oxo-2,3,6,7-tetrahydro-4H-thiazolo[4,5-c]pyridine-5-carboxylate (1h)

To a solution of tert-butyl 7-[allyloxy-(2-nitro-benzenesulfonyl)-amino]-3-methyl-2-oxo-2,3,6,7-tetrahydro-4H-thiazolo[4,5-c]pyridine-5-carboxylate (1g) (0.500 g, 0.95 mmol) in anhydrous ACN (6 mL) under inert atmosphere was added successively PhSH (0.487 mL, 4.75 mmol) and K₂CO₃ (0.985 g, 7.12 mmol). The reaction mixture was stirred for 16 h at rt. The reaction mixture was concentrated under vacuum, diluted with DCM and filtered to eliminate salts. The residue was purified by flash chromatography on silica gel (DCM/MeOH 100/0 to 95/5) then purified by preparative TLC (DCM/MeOH 95/5) to provide tert-butyl 7-allyloxyamino-3-methyl-2-oxo-2,3,6,7-tetrahydro-4H-thiazolo[4,5-c]pyridine-5-carboxylate (1h) (0.289 g, 0.84 mmol, 89%).

MS m/z ([M+H]⁺) 342.

¹H NMR (400 MHz, CDCl₃): δ(ppm) 1.47 (s, 9H), 3.21 (s, 3H), 3.30-3.40 (m, 1H), 3.81-4.06 (m, 2H), 4.17-4.26 (m, 2H), 4.35-4.69 (m, 1H), 5.16-5.32 (m, 2H), 5.38-5.43 (m, 1H), 5.87-5.97 (m, 1H), 6.21 (bs, 1H).

Step 9: Preparation of Intermediate 7-allyloxyamino-3-methyl-4,5,6,7-tetrahydro-3H-thiazolo[4,5-c]pyridin-2-one (1i)

To a solution of 7-allyloxyamino-3-methyl-2-oxo-2,3,6,7-tetrahydro-4H-thiazolo[4,5-c]pyridine-5-carboxylic acid tert-butyl ester (1h) (0.289 g, 0.85 mmol) in anhydrous DCM (5 mL) under inert atmosphere was added TFA (1 mL, 12.7 mmol). After stirring for 2 h at rt, the solution was cooled at 0° C. and neutralized to pH 8 with NH₄OH solution 28%. The solution was diluted with water, the organic layer was separated from the aqueous, dried over Na₂SO₄, filtered and concentrated in vacuo to 7-allyloxyamino-3-methyl-4,5,6,7-tetrahydro-3H-thiazolo[4,5-c]pyridin-2-one (1i) (0.140 g, 0.58 mmol, 68%) as a yellow oil.

¹H NMR (400 MHz, CDCl₃): δ(ppm) 2.97 (dd, J=3.6/13.6 Hz, 1H), 3.17 (s, 3H), 3.30 (dd, J=2.8/13.6 Hz, 1H), 3.59 (d, J=1.5/16.5 Hz, 1H), 3.69 (d, J=1.0/16.3 Hz, 1H), 3.75 (bs, 1H), 4.20 (dt, J=1.2/6.0 Hz, 2H), 5.20-5.25 (m, 2H), 5.61 (bs, 1H), 5.88-5.97 (m, 1H).

Step 10: Preparation of Intermediate 10-allyloxy-5-methyl-3-thia-5,8,10-triaza-tricyclo[6.2.1.0²·⁶]undec-2(6)-ene-4,9-dione (1j)

To a solution of 7-allyloxyamino-3-methyl-4,5,6,7-tetrahydro-3H-thiazolo[4,5-c]pyridin-2-one (1i) (0.140 g, 0.58 mmol) in anhydrous ACN (90 mL) at −10° C. under inert atmosphere was added TEA (0.323 mL, 2.32 mmol). A solution of diphosgene (0.035 mL, 0.29 mmol) in ACN (11 mL) was added dropwise at −10° C. After 2 h at −10° C. then 18 h at rt, the mixture reaction was bubbled 30 min under nitrogen and concentrated under vacuum. The residue was diluted with DCM, washed with water and NaCl aqueous solution. The organic layer was dried over Na₂SO₄, filtered and concentrated in vacuo. The product was purified by preparative TLC (DCM/MeOH 96/4) to provide 10-allyloxy-5-methyl-3-thia-5,8,10-triaza-tricyclo[6.2.1.0²·⁶]undec-2(6)-ene-4,9-dione (1j) (0.045 g, 0.17 mmol, 29%) as an colourless oil.

MS m/z ([M+H]⁺) 268.

¹H NMR (400 MHz, CDCl₃): δ(ppm) 3.16 (s, 3H), 3.28 (dd, J=0.4/11 Hz, 1H), 3.70 (dd, J=3.2/11 Hz, 1H), 4.06 (d, J=16.0 Hz, 1H), 4.20-4.24 (m, 2H), 4.39-4.51 (m, 2H), 5.32-5.38 (m, 2H), 5.97-6.07 (m, 1H).

Step 11: Preparation of Intermediate 10-hydroxy-5-methyl-3-thia-5,8,10-triaza-tricyclo[6.2.1.0²·⁶]undec-2(6)-ene-4,9-dione (1k)

To a solution of 10-allyloxy-5-methyl-3-thia-5,8,10-triaza-tricyclo[6.2.1.0²·⁶]undec-2(6)-ene-4,9-dione (1j) (0.050 g, 0.19 mmol) and glacial AcOH (0.011 mL, 0.19 mmol) in anhydrous DCM (3.2 mL) was added in one portion Pd(PPh₃)₄ (0.108 g, 0.09 mmol). After stirring for 3 h at rt, the mixture was concentrated and purified by flash chromatography (DCM/acetone 100/0 to 80/20) to provide 10-hydroxy-5-methyl-3-thia-5,8,10-triaza-tricyclo[6.2.1.0²·⁶]undec-2(6)-ene-4,9-dione (1k) (0.022 g, 0.10 mmol, 51%).

MS m/z ([M+H]⁺) 228.

¹H NMR (300 MHz, CDCl₃): δ(ppm) 3.13 (s, 3H), 3.24 (d, J=10.8 Hz, 1H), 3.66 (dd, J=2.9/10.9 Hz, 1H), 4.01 (d, J=16.7 Hz, 1H), 4.15 (s, 1H), 4.18 (d, J=16.8 Hz, 1H).

Step 12: Preparation of Sodium (5-methyl-4,9-dioxo-3-thia-5,8,10-triaza-tricyclo[6.2.1.0²·⁶]undec-2(6)-en-10-yl) sulfate (Example 1)

To a solution of 10-hydroxy-5-methyl-3-thia-5,8,10-triaza-tricyclo[6.2.1.0²·⁶]undec-2(6)-ene-4,9-dione (1k) (0.022 g, 0.10 mmol) in anhydrous DCM (1.5 mL) was added a suspension of sulfur trioxide pyridine complex (0.092 mg, 0.58 mmol) in dry pyridine (1 mL) and the resulting solution was protected from light and stirred overnight at rt until the sulfatation was completed. The reaction mixture was concentrated under vacuum, diluted with DCM and filtered. The filtrate was co-evaporated with toluene and dried under vacuum. The residue was solubilized in a minimal volume of water and applied on a Dowex sodium form column (Dowex® 50WX8 hydrogen form stored with an aqueous solution of 2N NaOH and washed until neutral pH with water). The fractions containing the desired compound were combined, frozen and lyophilized to afford sodium (5-methyl-4,9-dioxo-3-thia-5,8,10-triaza-tricyclo[6.2.1.0²·⁶]

undec-2(6)-en-10-yl) sulfate (Example 1) (0.032 g, 0.10 mmol, quantitative yield) as a white solid.

MS m/z ([M−H]⁻) 306.

¹H NMR (300 MHz, D₂O): δ(ppm) 3.20 (s, 3H), 3.58 (d, J=11.5 Hz, 1H), 3.84 (dd, J=3.0/11.5 Hz, 1H), 4.29 (d, J=16.9 Hz, 1H), 4.40 (d, J=16.9 Hz, 1H), 4.80 (bs, in D₂O peak, 1H).

Example 2

Synthesis of Sodium [5-(2-methoxy-2-oxo-ethyl)-4,9-dioxo-3-thia-5,8,10-triaza-tricyclo[6.2.1.0²·⁶]undec-2(6)-en-10-yl] sulfate

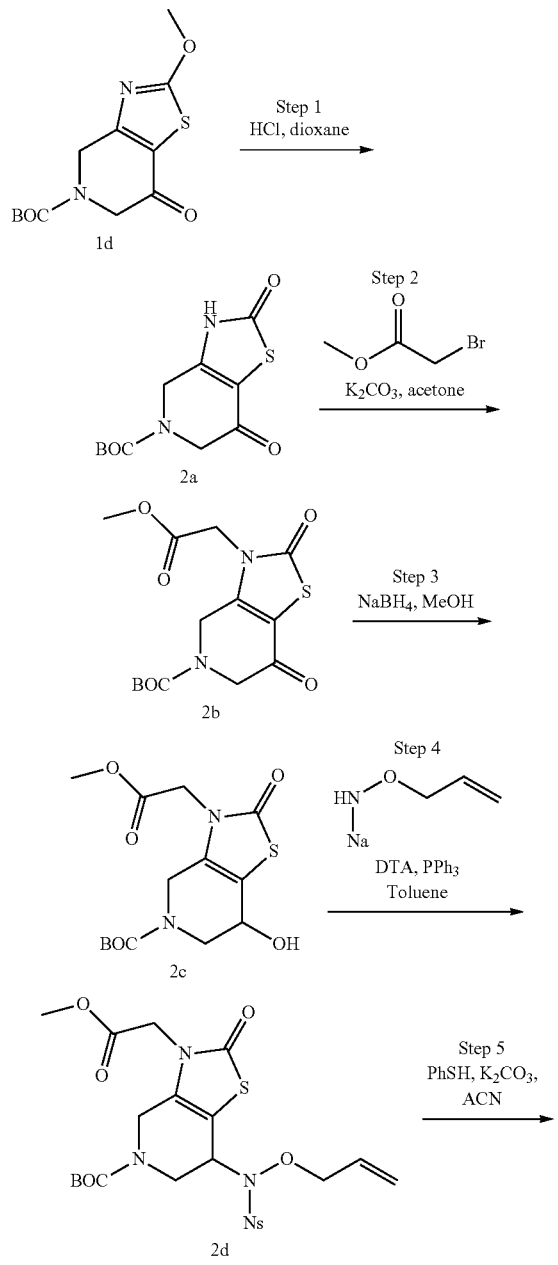

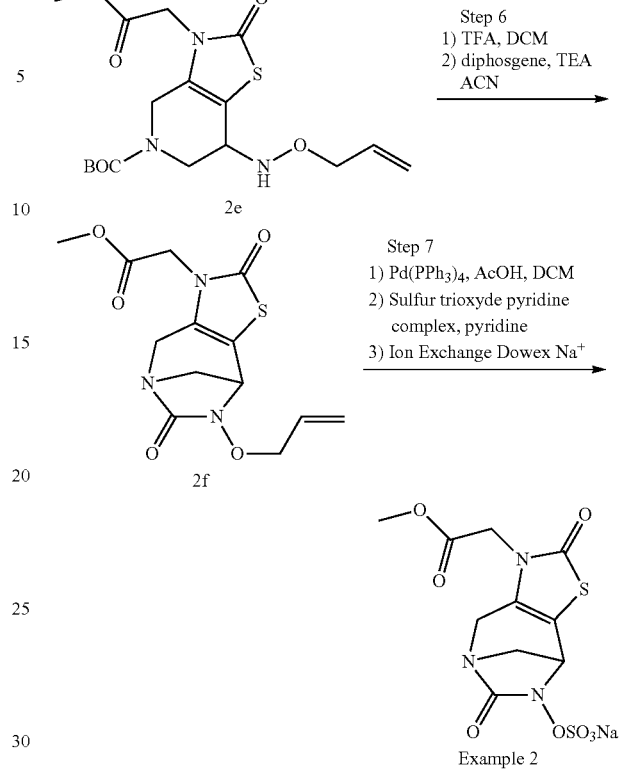

Step 1: Preparation of Intermediate tert-butyl 2,7-dioxo-4,6-dihydro-3H-thiazolo[4,5-c]pyridine-5-carboxylate (2a)

To a solution of tert-butyl 2-methoxy-7-oxo-6,7-dihydro-4H-thiazolo[4,5-c]pyridine-5-carboxylate (1d) (7.19 g, 25.31 mmol) in anhydrous dioxane (193 mL) was added drop by drop HCl 12 N (2.50 mL). The reaction mixture was stirred for 4 h at 70° C. then concentrated under vacuum. The residue was diluted with EtOAc and washed with water. The organic layer was dried over Na₂SO₄, filtered and concentrated in vacuo to provide tert-butyl 2,7-dioxo-4,6-dihydro-3H-thiazolo[4,5-c]pyridine-5-carboxylate (2a) (3.43 g, 12.70 mmol, 50%) as an orange solid.

MS m/z ([M−tBu+H]⁺) 215.
MS m/z ([M−H]⁻) 269.

Step 2: Preparation of Intermediate tert-butyl 3-(2-methoxy-2-oxo-ethyl)-2,7-dioxo-4,6-dihydrothiazolo[4,5-c]pyridine-5-carboxylate (2b)

To a solution of tert-butyl 2,7-dioxo-4,6-dihydro-3H-thiazolo[4,5-c]pyridine-5-carboxylate (2a) (418 mg, 1.55 mmol) in anhydrous acetone (15 mL) under inert atmosphere were added K₂CO₃ (214 mg, 1.55 mmol) and methyl-2-bromoacetate (146 μL, 1.55 mmol) and the mixture was stirred for 2 h at 55° C. and concentrated in vacuo. The residue was diluted with EtOAc, washed with NaCl aqueous solution, dried over Na₂SO₄, filtered and concentrated. The crude was purified by flash chromatography on silica gel (DCM/MeOH 98/2) to provide tert-butyl 3-(2-methoxy-2-oxo-ethyl)-2,7-dioxo-4,6-dihydrothiazolo[4,5-c]pyridine-5-carboxylate (2b) (493 mg, 1.44 mmol, 93%) as a yellow oil.

MS m/z ([M−tBu+H]⁺) 287.

MS m/z ([M–H]⁻) 341.

¹H NMR (400 MHz, CDCl₃): δ(ppm) 1.48 (s, 9H), 3.82 (s, 3H), 4.28 (s, 2H), 4.54 (s, 2H), 5.55 (s, 2H).

Step 3: Preparation of Intermediate tert-butyl 7-hydroxy-3-(2-methoxy-2-oxo-ethyl)-2-oxo-6,7-dihydro-4H-thiazolo[4,5-c]pyridine-5-carboxylate (2c)

Using the procedure described in example 1 (step 6), tert-butyl 3-(2-methoxy-2-oxo-ethyl)-2,7-dioxo-4,6-dihydrothiazolo[4,5-c]pyridine-5-carboxylate (2b) (570 mg, 1.66 mmol) was converted to tert-butyl 7-hydroxy-3-(2-methoxy-2-oxo-ethyl)-2-oxo-6,7-dihydro-4H-thiazolo[4,5-c]pyridine-5-carboxylate (2c) (424 mg, 1.23 mmol, 74%) as a yellow oil.

MS m/z ([M+Na]⁺) 367.

MS m/z ([M–H]⁻) 343.

¹H NMR (400 MHz, CDCl₃): δ(ppm) 1.49 (s, 9H), 3.57 (dd, J=3.4/13.8 Hz, 1H), 3.79 (s, 3H), 3.91-3.98 (m, 1H), 4.01 (dd, J=3.9/13.8 Hz, 1H), 4.29-4.59 (m, 4H).

Step 4: Preparation of Intermediate tert-butyl 7-[allyloxy-(2-nitrophenyl)sulfonyl-amino]-3-(2-methoxy-2-oxo-ethyl)-2-oxo-6,7-dihydro-4H-thiazolo[4,5-c]pyridine-5-carboxylate (2d)

Using the procedure described in example 1 (step 7), tert-butyl 7-hydroxy-3-(2-methoxy-2-oxo-ethyl)-2-oxo-6,7-dihydro-4H-thiazolo[4,5-c]pyridine-5-carboxylate (2c) (424 mg, 1.2 mmol) was converted to tert-butyl 7-[allyloxy-(2-nitrophenyl)sulfonyl-amino]-3-(2-methoxy-2-oxo-ethyl)-2-oxo-6,7-dihydro-4H-thiazolo[4,5-c]pyridine-5-carboxylate (2d) (257 mg, 0.44 mmol, 35%) as a yellow oil after a purification by flash chromatography on silica gel (cyclohexane/EtOAc 6/4).

Step 5: Preparation of Intermediate tert-butyl 7-(allyloxyamino)-3-(2-methoxy-2-oxo-ethyl)-2-oxo-6,7-dihydro-4H-thiazolo[4,5-c]pyridine-5-carboxylate (2e)

Using the procedure described in example 1 (step 8), tert-butyl 7-[allyloxy-(2-nitrophenyl)sulfonyl-amino]-3-(2-methoxy-2-oxo-ethyl)-2-oxo-6,7-dihydro-4H-thiazolo[4,5-c]pyridine-5-carboxylate (2d) (256 mg, 0.40 mmol) is converted to tert-butyl 7-(allyloxyamino)-3-(2-methoxy-2-oxo-ethyl)-2-oxo-6,7-dihydro-4H-thiazolo[4,5-c]pyridine-5-carboxylate (2e) (118 mg, 0.30 mmol, 69%) after a purification by preparative TLC (DCM/MeOH 95/5).

MS m/z ([M+H]⁺) 400.

¹H NMR (400 MHz, CDCl₃): δ(ppm) 1.44 (s, 9H), 3.31-3.42 (m, 1H), 3.73 (s, 3H), 3.84-3.96 (m, 2H), 4.19 (d, J=5.8 Hz, 2H), 4.25-4.29 (m, 1H), 4.34-4.52 (m, 2H), 5.14-5.17 (m, 1H), 5.22-5.29 (m, 2H), 5.83-5.93 (m, 1H).

Step 6: Preparation of Intermediate 10-allyloxy-5-(2-methoxy-2-oxo-ethyl)-3-thia-5,8,10-triaza-tricyclo[6.2.1.0²·⁶]undec-2(6)-ene-4,9-dione (2f)

To a solution of tert-butyl 7-(allyloxyamino)-3-(2-methoxy-2-oxo-ethyl)-2-oxo-6,7-dihydro-4H-thiazolo[4,5-c]pyridine-5-carboxylate (2e) (1.5 g, 3.77 mmol) in anhydrous DCM (38 mL) was added drop by drop TFA (4.4 mL, 56.48 mmol). The mixture was stirred for 3 h at 0° C., then neutralized with an ammonium hydroxide 28% solution (pH 7-8) and extracted twice with DCM. The combined organic layers were dried over Na₂SO₄, filtered and concentrated.

The crude was dissolved in ACN (627 mL) and cooled down at –10° C. TEA (2.1 mL, 15.06 mmol) and a solution of diphosgene (227 µL, 0.1.88 mmol) in ACN (70 mL) were added. After 1 h at rt, the mixture was stirred at 45° C. and TEA was added until total consumption of starting material. The crude was concentrated in vacuo and purified by flash chromatography on silica gel (DCM/MeOH 96/4) to afford 10-allyloxy-5-(2-methoxy-2-oxo-ethyl)-3-thia-5,8,10-triaza-tricyclo[6.2.1.0²·⁶]undec-2(6)-ene-4,9-dione (2f) (569 mg, 1.74 mmol, 51%).

MS m/z ([M+H]⁺) 326.

1H NMR (300 MHz, CDCl₃): δ(ppm) 3.31 (d, J=10.7 Hz, 1H), 3.66 (dd, J=2.9/11.0 Hz, 1H), 3.76 (s, 3H), 3.97-4.11 (m, 3H), 4.19 (d, J=2.4 Hz, 1H), 4.34-4.48 (m, 2H), 4.60 (d, J=17.8 Hz, 1H), 5.27-5.38 (m, 2H), 5.91-6.04 (m, 1H).

Step 7: Preparation of Sodium [5-(2-methoxy-2-oxo-ethyl)-4,9-dioxo-3-thia-5,8,10-triaza-tricyclo[6.2.1.0²·⁶]undec-2(6)-en-10-yl] sulfate (example 2)

To a solution of 10-allyloxy-5-(2-methoxy-2-oxo-ethyl)-3-thia-5,8,10-triaza-tricyclo[6.2.1.0²·⁶]undec-2(6)-ene-4,9-dione (2f) (42.2 mg, 0.13 mmol) and glacial AcOH (15 µL, 0.23 mmol) in anhydrous DCM (930 µL) was added in one portion Pd(Ph₃)₄ (75 mg, 0.07 mmol). After stirring for 30 min at rt, dry pyridine (772 µL) and sulfur trioxide pyridine complex (103 mg, 0.65 mmol) were added to the mixture and the resulting solution was protected from light and stirring overnight at rt until sulfatation was completed. The reaction mixture was concentrated in vacuo, diluted with DCM and filtered. The filtrate was concentrated and purified on silica gel (DCM/acetone 100/0 to 60/40) to provide 38 mg of a uncolored oil of triphenyl-(propenyl)-phosphonium salt [5-(2-methoxy-2-oxo-ethyl)-4,9-dioxo-3-thia-5,8,10-triaza-tricyclo[6.2.1.0²·⁶]undec-2(6)-en-10-yl]sulfate. This oil was solubilized in a minimal volume of water and ACN and applied on a Dowex sodium form column (Dowex® 50WX8 hydrogen form stored with an aqueous solution of 2N NaOH and washed until neutral pH with water). The fractions containing the desired compound were combined, frozen and lyophilized to afford sodium [5-(2-methoxy-2-oxo-ethyl)-4,9-dioxo-3-thia-5,8,10-triaza-tricyclo[6.2.1.0²·⁶]undec-2(6)-en-10-yl] sulfate (example 2) (11.4 mg, 0.029 mmol, 22%) as a white solid.

MS m/z ([M–H]⁻) 364.

¹H NMR (400 MHz, D₂O): δ(ppm) 3.63 (d, J=11.5 Hz, 1H), 3.82 (s, 3H), 3.87 (dd, J=3.0/11.5 Hz, 1H), 4.20-4.36 (m, 2H), 4.52-4.62 (m, 2H), 4.85 (d, J=2.7 Hz, 1H).

Example 3

Synthesis of Sodium [5-(2-(tert-butoxycarbonylamino)ethyl)-4,9-dioxo-3-thia-5,8,10-triaza-tricyclo[6.2.1.0²·⁶]undec-2(6)-en-10-yl] sulfate

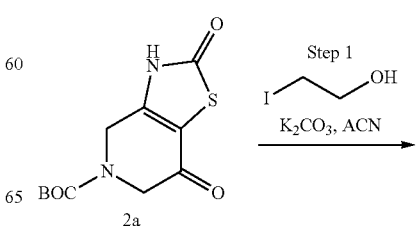

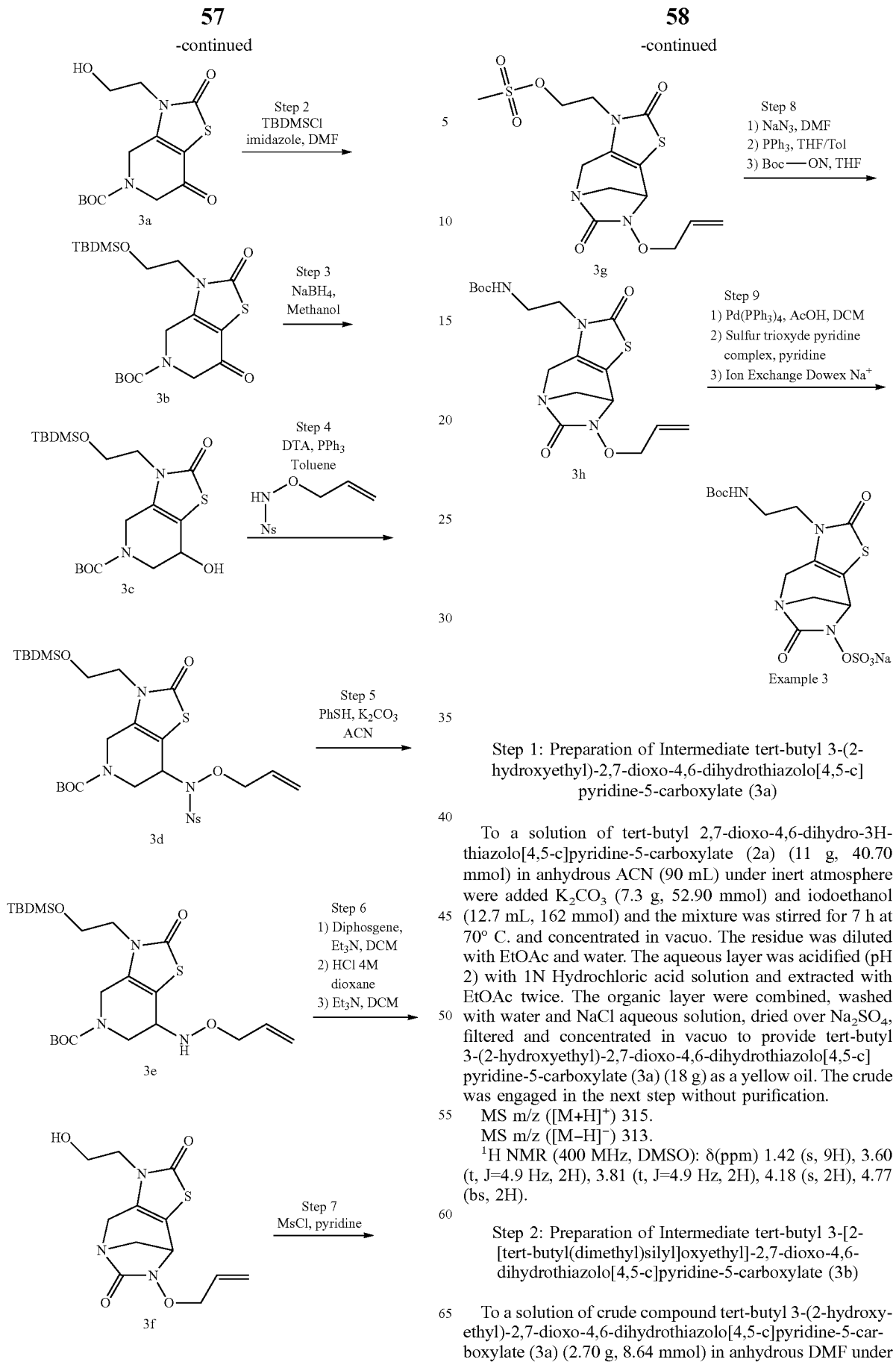

Step 1: Preparation of Intermediate tert-butyl 3-(2-hydroxyethyl)-2,7-dioxo-4,6-dihydrothiazolo[4,5-c]pyridine-5-carboxylate (3a)

To a solution of tert-butyl 2,7-dioxo-4,6-dihydro-3H-thiazolo[4,5-c]pyridine-5-carboxylate (2a) (11 g, 40.70 mmol) in anhydrous ACN (90 mL) under inert atmosphere were added $K_2CO_3$ (7.3 g, 52.90 mmol) and iodoethanol (12.7 mL, 162 mmol) and the mixture was stirred for 7 h at 70° C. and concentrated in vacuo. The residue was diluted with EtOAc and water. The aqueous layer was acidified (pH 2) with 1N Hydrochloric acid solution and extracted with EtOAc twice. The organic layer were combined, washed with water and NaCl aqueous solution, dried over $Na_2SO_4$, filtered and concentrated in vacuo to provide tert-butyl 3-(2-hydroxyethyl)-2,7-dioxo-4,6-dihydrothiazolo[4,5-c]pyridine-5-carboxylate (3a) (18 g) as a yellow oil. The crude was engaged in the next step without purification.

MS m/z ([M+H]$^+$) 315.
MS m/z ([M−H]$^-$) 313.
$^1$H NMR (400 MHz, DMSO): δ(ppm) 1.42 (s, 9H), 3.60 (t, J=4.9 Hz, 2H), 3.81 (t, J=4.9 Hz, 2H), 4.18 (s, 2H), 4.77 (bs, 2H).

Step 2: Preparation of Intermediate tert-butyl 3-[2-[tert-butyl(dimethyl)silyl]oxyethyl]-2,7-dioxo-4,6-dihydrothiazolo[4,5-c]pyridine-5-carboxylate (3b)

To a solution of crude compound tert-butyl 3-(2-hydroxyethyl)-2,7-dioxo-4,6-dihydrothiazolo[4,5-c]pyridine-5-carboxylate (3a) (2.70 g, 8.64 mmol) in anhydrous DMF under inert atmosphere were added tert-butyl-chloro-dimethyl-silane (1.43 g, 9.50 mmol) and imidazole (1.17 g, 17.18 mmol). The mixture was stirred for 1 h at rt then ice and EtOAc were added. The organic layer was separated, washed with a saturated solution of NaCl, dried over $Na_2SO_4$, filtered and concentrated in vacuo to provide tert-butyl 3-[2-[tert-butyl(dimethyl)silyl]oxyethyl]-2,7-dioxo-4,6-dihydrothiazolo[4,5-c]pyridine-5-carboxylate (3b) (2.46 g, 5.74 mmol, 66% over 2 steps) as a brown oil which was engaged in the next step without further purification.

MS m/z ([M+H]$^+$) 429.
MS m/z ([M–H]$^-$) 427.
$^1$H NMR (400 MHz, CDCl$_3$): δ(ppm) 0.00 (s, 6H), 0.83 (s, 9H), 1.49 (s, 9H), 3.87 (s, 4H), 4.23 (s, 2H), 4.68 (bs, 2H).

Step 3: Preparation of Intermediate tert-butyl 3-[2-[tert-butyl(dimethyl)silyl]oxyethyl]-7-hydroxy-2-oxo-6,7-dihydro-4H-thiazolo[4,5-c]pyridine-5-carboxylate (3c)

Using the procedure described in example 1 (step 6), tert-butyl 3-[2[tert-butyl(dimethyl)silyl]oxyethyl]-2,7-dioxo-4,6-dihydrothiazolo[4,5-c]pyridine-5-carboxylate (3b) (15.09 g, 35.20 mmol) is converted to tert-butyl 3-[2-[tert-butyl(dimethyl)silyl]oxyethyl]-7-hydroxy-2-oxo-6,7-dihydro-4H-thiazolo[4,5-c]pyridine-5-carboxylate (3c) (6.76 g, 15.6 mmol, 44%) as a yellow oil after a purification by flash chromatography on silica gel (DCM/MeOH 100/0 to 98/2).

MS m/z ([M+H]$^+$) 431.
$^1$H NMR (400 MHz, CDCl$_3$): δ(ppm) 0.00 (bs, 6H), 0.84 (s, 9H), 1.50 (s, 9H), 3.48 (dd, J=3.4/13.7 Hz, 1H), 3.66-3.84 (m, 4H), 4.00-4.10 (m, 2H), 4.50-4.73 (m, 2H)

Step 4: Preparation of Intermediate tert-butyl 7-[allyloxy-(2-nitrophenyl)sulfonyl-amino]-3-[2-[tert-butyl(dimethyl)silyl]oxyethyl]-2-oxo-6,7-dihydro-4H-thiazolo[4,5-c]pyridine-5-carboxylate (3d)

Using the procedure described in example 1 (step 7), tert-butyl 3-[2-[tert-butyl(dimethyl)silyl]oxyethyl]-7-hydroxy-2-oxo-6,7-dihydro-4H-thiazolo[4,5-c]pyridine-5-carboxylate (3c) (6.70 g, 15.56 mmol) is converted to tert-butyl 7-[allyloxy-(2-nitrophenyl)sulfonyl-amino]-3-[2-[tert-butyl (dimethyl)silyl]oxyethyl]-2-oxo-6,7-dihydro-4H-thiazolo[4,5-c]pyridine-5-carboxylate (3d) using N-allyloxy-2-nitrobenzenesulfonamide (4.82 g, 18.67 mmol), PPh$_3$ (4.08 g, 18.67 mmol) and DTA (4.30 g, 18.6 mmol). After 1 h of reaction, magnesium chloride (3.60 g, 37.30 mmol) was added and the reaction mixture was stirred for 2 h at 60° C. then overnight at rt. The solution was filtered and concentrated in vacuo. The residue was purified by flash chromatography on silica gel (toluene/acetone 100/0 to 90/10) to provide compound (3d) (5.54 g, 8.20 mmol, 53%) as a yellow oil.

Step 5: Preparation of Intermediate tert-butyl 7-(allyloxyamino)-3-[2-[tert-butyl(dimethyl)silyl]oxyethyl]-2-oxo-6,7-dihydro-4H-thiazolo[4,5-c]pyridine-5-carboxylate (3e)

Using the procedure described in example 1 (step 8), tert-butyl 7-[allyloxy-(2-nitrophenyl)sulfonyl-amino]-3-[2-[tert-butyl(dimethyl)silyl]oxyethyl]-2-oxo-6,7-dihydro-4H-thiazolo[4,5-c]pyridine-5-carboxylate (3d) (5.2 g, 7.76 mmol) is converted to tert-butyl 7-(allyloxyamino)-3-[2-[tert-butyl(dimethyl)silyl]oxyethyl]-2-oxo-6,7-dihydro-4H-thiazolo[4,5-c]pyridine-5-carboxylate (3e) (2.53 g, 5.21 mmol, 67%) after a purification on silica gel (cyclohexane/EtOAc 80/20 to 60/40).

Step 6: Preparation of Intermediate 10-Allyloxy-5-(2-hydroxy-ethyl)-3-thia-5,8,10-triaza-tricyclo [6.2.1.0$^{2.6}$]undec-2(6)-ene-4,9-dione (3f)

To a solution of tert-butyl 7-(allyloxyamino)-3-[2-[tert-butyl(dimethyl)silyl]oxyethyl]-2-oxo-6,7-dihydro-4H-thiazolo[4,5-c]pyridine-5-carboxylate (3e) (4.29 g, 8.83 mmol) in DCM (88.3 mL) were added TEA (2.46 mL, 17.7 mmol) and diphosgene (1.58 mL, 11.48 mmol). After 5 min, the solution was washed with NaCl aqueous solution. The organic layer was dried over Na$_2$SO$_4$, filtered and concentrated in vacuo. The yellow oil obtained was stirred with 4M HCl solution in dioxane (88.3 mL) during 1 h. The mixture was concentrated in vacuo and to the crude in DCM (88.4 mL) was dropwise added TEA (2.25 mL, 17.67 mmol). The reaction mixture was stirred at rt for 30 min then diluted with DCM and washed with water. The organic layer was dried over Na$_2$SO$_4$ and concentrated in vacuo. The crude was purified by flash chromatography on silica gel (DCM/MeOH 100/0 to 90/10) to afford 10-allyloxy-5-(2-hydroxy-ethyl)-3-thia-5,8,10-triaza-tricyclo[6.2.1.0$^{2.6}$]undec-2(6)-ene-4,9-dione (3f) (1.72 g, 5.78 mmol, 66%).

MS m/z ([M+H]$^+$) 298.
$^1$H NMR (300 MHz, CDCl$_3$): δ(ppm) 3.27 (d, J=10.8 Hz, 1H), 3.52-3.78 (m, 7H), 4.18 (s, 1H), 4.33-4.47 (m, 2H), 5.28-5.38 (m, 2H), 5.90-6.04 (m, 1H).

Step 7: Preparation of Intermediate 10-allyloxy-5-(2-methylsulfonyloxyethyl)-3-thia-5,8,10-triaza-tricyclo[6.2.1.0$^{2.6}$]undec-2(6)-ene-4,9-dione (3g)

To a solution of 10-allyloxy-5-(2-hydroxy-ethyl)-3-thia-5,8,10-triaza-tricyclo[6.2.1.0$^{2.6}$]undec-2(6)-ene-4,9-dione (3f) (316 mg, 1.06 mmol) in anhydrous pyridine (5.3 mL) at 0° C. was added MsCl (132 µL, 1.70 mmol). The mixture was stirred for 2 h at 0° C. then concentrated in vacuo. The residue was diluted with DCM and washed with a 2N HCl solution. The organic layer was dried over Na$_2$SO$_4$, filtered and concentrated in vacuo to provide 10-allyloxy-5-(2-methylsulfonyloxyethyl)-3-thia-5,8,10-triaza-tricyclo [6.2.1.0$^{2.6}$]undec-2(6)-ene-4,9-dione (3g) which was engaged in the next step without further purification.

MS m/z ([M+H]$^+$) 376.

Step 8: Preparation of Intermediate 10-allyloxy-5-(2-(tert-butoxycarbonylamino)ethyl)-3-thia-5,8,10-triaza-tricyclo[6.2.1.0$^{2.6}$]undec-2(6)-ene-4,9-dione (3h)

In a sealed flask, to a solution of 10-allyloxy-5-(2-methylsulfonyloxyethyl)-3-thia-5,8,10-triaza-tricyclo[6.2.1.0$^{2.6}$] undec-2(6)-ene-4,9-dione (3g) (1.06 mmol) in anhydrous DMF (5.30 mL) was added NaN$_3$ (345 mg, 5.31 mmol). The reaction mixture was stirred 18 h at 65° C. before concentration in vacuo. The residue was dissolved in EtOAc and washed with NaCl aqueous solution. The organic layer was dried over Na$_2$SO$_4$, filtered and concentrated in vacuo. The yellow oil was dissolved in anhydrous THF (3.2 mL) and toluene (3.2 mL) and a solution of PMe$_3$ 1M in THF (1.6 mL) was added. The reaction mixture was stirred 1 h at rt then cooled to 0° C. and a solution of BocON (392 mg, 1.6 mmol) in anhydrous THF (2.2 mL) was slowly added. After 1 h at rt, the reaction mixture was concentrated in vacuo and purified by flash chromatography on silica gel (cyclohexane/EtOAc 100/0 to 0/100) to afford 10-allyloxy-5-(2-(tert-butoxycarbonylamino)ethyl)-3-thia-5,8,10-triaza-tricyclo[6.2.1.0$^{2.6}$]undec-2(6)-ene-4,9-dione (3h) (190 mg, 0.50 mmol, 45% over 2 steps) as a off white oil.

MS m/z ([M+H]$^+$) 397.

$^1$H NMR (300 MHz, CDCl$_3$): δ(ppm) 1.41-1.42 (m, 9H), 3.27-3.36 (m, 2H), 3.47-3.55 (m, 1H), 3.65 (dd, J=2.8/10.9 Hz, 1H), 3.72-3.81 (m, 1H), 4.15 (dd, J=1.9/4.8 Hz, 2H), 4.34-4.48 (m, 2H), 4.37-4.90 (m, 1H), 5.28-5.38 (m, 2H), 5.91-6.05 (m, 1H), 7-13-7.24 (m, 1H).

Step 9: Preparation of Sodium [5-(2-(tert-butoxycarbonylamino)ethyl)-4,9-dioxo-3-thia-5,8,10-triaza-tricyclo[6.2.1.0$^{2.6}$]undec-2(6)-en-10-yl] sulfate (Example 3)

Using the procedure described in example 1 (step 7), 10-allyloxy-5-(2-(tert-butoxycarbonylamino)ethyl)-3-thia-5,8,10-triaza-tricyclo[6.2.1.0$^{2.6}$]undec-2(6)-ene-4,9-dione (3h) (190 mg, 0.48 mmol) is converted to sodium [5-(2-(tert-butoxycarbonylamino)ethyl)-4,9-dioxo-3-thia-5,8,10-triaza-tricyclo[6.2.1.0$^{2.6}$]undec-2(6)-en-10-yl] sulfate (example 3) (62.4 mg, 0.14 mmol, 28%) as a white solid.

MS m/z ([M−H]$^−$) 435.

$^1$H NMR (400 MHz, D$_2$O): δ(ppm) 1.36-1.38 (s, 9H), 3.24-3.40 (m, 2H), 3.44-3.53 (m, 1H), 3.62-3.67 (m, 2H), 3.82 (dd, J=2.99/11.6 Hz, 1H), 4.20-4.35 (m, 2H), 4.76 (m, in D$_2$O peak, 1H).

Example 4

Synthesis of Sodium and 2,2,2-trifluoroacetate [5-(2-azaniumethyl)-4,9-dioxo-3-thia-5,8,10-triaza-tricyclo[6.2.1.0$^{2.6}$]undec-2(6)-en-10-yl] sulfate

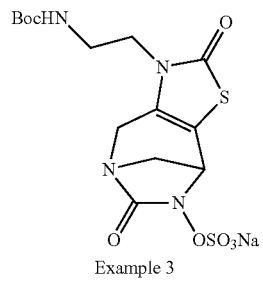

Example 3

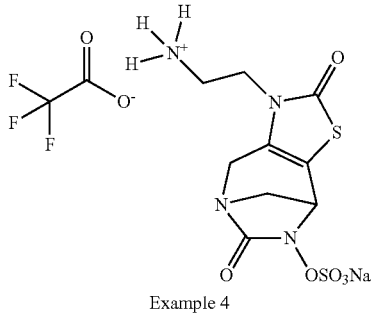

Example 4

Step 1: Preparation of Sodium and 2,2,2-trifluoroacetate [5-(2-azaniumethyl)-4,9-dioxo-3-thia-5,8,10-triaza-tricyclo[6.2.1.0$^{2.6}$]undec-2(6)-en-10-yl] sulfate (Example 4)

At 0° C., a solution of TFA (155 μL) in DCM (105 μL) was prepared and added to a solution of sodium [5-(2-(tert-butoxycarbonylamino)ethyl)-4,9-dioxo-3-thia-5,8,10-triaza-tricyclo[6.2.1.0$^{2.6}$]undec-2(6)-en-10-yl] sulfate (Example 3) (5.7 mg, 0.013 mmol) in DCM (155 μL) at 0° C. The reaction mixture was stirred 30 min at this temperature then concentrated under nitrogen flux. The solid was dissolved in water (1 mL), filtered, frozen and lyophilized to afford sodium and 2,2,2-trifluoroacetate [5-(2-azaniumethyl)-4,9-dioxo-3-thia-5,8,10-triaza-tricyclo[6.2.1.0$^{2.6}$]undec-2(6)-en-10-yl] sulfate (Example 4) (3.2 mg, 0.007 mmol, 54%) as a white solid.

MS m/z ([M−H]$^−$) 335.

$^1$H NMR (300 MHz, D$_2$O): δ(ppm) 3.26 (t, J=6.0 Hz, 2H), 3.54 (d, J=11.5 Hz, 1H), 3.81 (dd, J=3.0/11.5 Hz, 1H), 3.92-3.98 (m, 2H), 4.25 (d, J=16.8 Hz, 1H), 4.38 (d, J=16.9 Hz, 1H), 4.70-4.86 (m, in D$_2$O peak, 1H).

Example 5

Synthesis of Sodium [5-(2-hydroxyethyl)-4,9-dioxo-3-thia-5,8,10-triaza-tricyclo[6.2.1.0$^{2.6}$]undec-2(6)-en-10-yl) sulfate

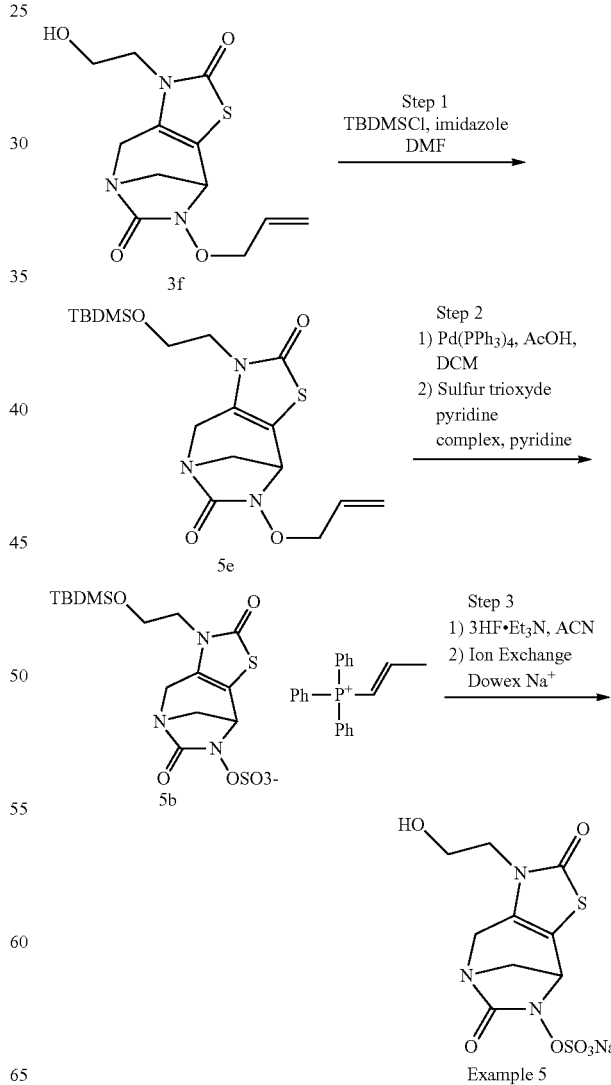

Step 1: Preparation of Intermediate 10-Allyloxy-5-[2-[tert-butyl(dimethyl)silyl]oxyethyl]-3-thia-5,8,10-triaza-tricyclo[6.2.1.0$^{2.6}$]undec-2(6)-ene-4,9-dione (5a)

To a solution of 10-allyloxy-5-(2-hydroxy-ethyl)-3-thia-5,8,10-triaza-tricyclo[6.2.1.0$^{2.6}$]undec-2(6)-ene-4,9-dione (3f) (150 mg, 0.50 mmol) in anhydrous DMF were added TBDMSCl (84 mg, 0.56 mmol) and imidazole (69 mg, 1.01 mmol). After 1 h at rt, the reaction mixture was diluted with EtOAc and washed with water. The organic layer was separated, dried over Na$_2$SO$_4$ and concentrated in vacuo. The crude was purified by flash chromatography on silica gel (cyclohexane/EtOAc 8/2 to 2/8) to afford 10-allyloxy-5-[2-[tert-butyl(dimethyl)silyl]oxyethyl]-3-thia-5,8,10-triaza-tricyclo[6.2.1.0$^{2.6}$]undec-2(6)-ene-4,9-dione (5a) (174 mg, 0.42 mmol, 83%).

MS m/z ([M+H]$^+$) 412.

$^1$H NMR (400 MHz, CDCl$_3$): δ(ppm) 0.02 (d, J=7.3 Hz, 6H), 0.86 (s, 9H), 3.16-3.23 (m, 1H), 3.37-3.46 (m, 1H), 3.63-3.86 (m, 4H), 4.16-4.21 (m, 3H), 4.35-4.50 (m, 2H), 5.28-5.39 (m, 2H), 5.93-6.06 (m, 1H).

Step 2: Preparation of Intermediate triphenyl-(propenyl)-phosphonium [5-[2-[tert-butyl(dimethyl)silyl]oxyethyl]-4,9-dioxo-3-thia-5,8,10-triaza-tricyclo[6.2.1.0$^{2.6}$]undec-2(6)-en-10-yl] sulfate (5b)

Using the procedure described in example 2 (step 7), 10-allyloxy-5-[2-[tert-butyl(dimethyl)silyl]oxyethyl]-3-thia-5,8,10-triaza-tricyclo[6.2.1.0$^{2.6}$]undec-2(6)-ene-4,9-dione (5a) (170 mg, 0.41 mmol) is converted to triphenyl-(propenyl)-phosphonium [5-[2-[tert-butyl(dimethyl)silyl]oxyethyl]-4,9-dioxo-3-thia-5,8,10-triaza-tricyclo[6.2.1.0$^{2.6}$]undec-2(6)-en-10-yl] sulfate (5b) (135 mg, 0.18 mmol 43%).

MS m/z ([M−H]$^−$) 450.

Step 3: Preparation of Sodium [5-(2-hydroxyethyl)-4,9-dioxo-3-thia-5,8,10-triaza-tricyclo[6.2.1.0$^{2.6}$]undec-2(6)-en-10-yl) sulfate (example 5)

Triethylamine trihydrofluoride (29 μL, 0.18 mmol) was added to a solution of triphenyl-(propenyl)-phosphonium [5-[2-[tert-butyl(dimethyl)silyl]oxyethyl]-4,9-dioxo-3-thia-5,8,10-triaza-tricyclo[6.2.1.0$^{2.6}$]undec-2(6)-en-10-yl] sulfate (5b) (135 mg, 0.18 mmol) in anhydrous ACN (1.46 mL) under inert atmosphere. The reaction mixture was vigorously stirred at 45° C. for 5 h until complete conversion of starting material. The reaction mixture was concentrated under nitrogen flow and directly applied on a Dowex sodium form column. The fractions containing the desired compound were combined and concentrated. The solid was diluted in a minimum of MeOH (300 μL), filtered on Millipore to remove sodium fluoride salts and concentrated. The solid was diluted with water, freezed and lyophilized to afford compound sodium [5-(2-hydroxyethyl)-4,9-dioxo-3-thia-5,8,10-triaza-tricyclo[6.2.1.0$^{2.6}$]undec-2(6)-en-10-yl) sulfate (example 5) (16.6 mg, 0.05 mmol, 28%) as a white solid.

MS m/z ([M−H]$^−$) 336.

$^1$H NMR (300 MHz, D$_2$O): δ(ppm) 3.58 (dd, J=0.4/11.5 Hz, 1H), 3.74 (s, 4H), 3.85 (dd, J=3.0/11.5 Hz, 1H), 4.34 (d, J=18 Hz, 1H), 4.41 (d, J=18 Hz, 1H), 4.70-4.86 (m, in D$_2$O peak, 1H).

Example 6

Synthesis of Sodium and 2,2,2-trifluoroacetate [5-(2-quanidiniumethyl)-4,9-dioxo-3-thia-5,8,10-triaza-tricyclo[6.2.1.0$^{2.6}$]undec-2(6)-en-10-yl] sulfate

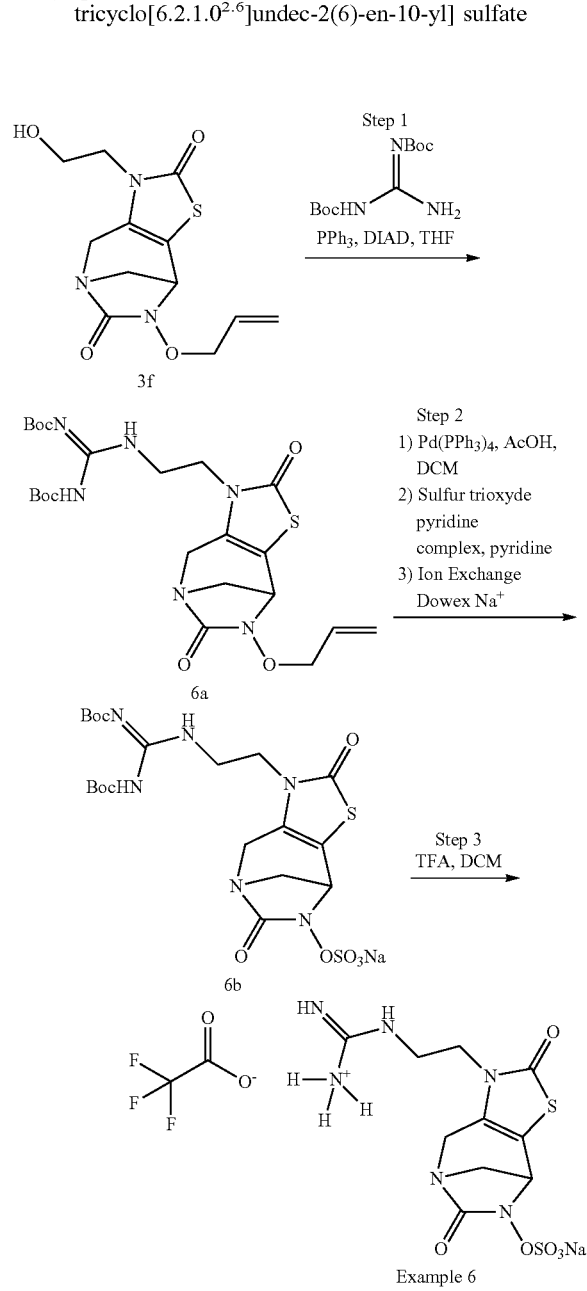

Example 6

Step 1: Preparation of Intermediate 10-allyloxy-5-(2-[[N,N$^1$-bis(tert-butoxycarbonyl)carbamimidoyl]amino]ethyl)-3-thia-5,8,10-triaza-tricyclo[6.2.1.0$^{2.6}$]undec-2(6)-ene-4,9-dione (6a)

To a solution of 10-allyloxy-5-(2-hydroxy-ethyl)-3-thia-5,8,10-triaza-tricyclo[6.2.1.0$^{2.6}$]undec-2(6)-ene-4,9-dione (3f) (130 mg, 0.44 mmol) in anhydrous THF (4.4 mL) under inert atmosphere was added 1,3-Bis(tert-butoxycarbonyl) guanidine (160 mg, 0.61 mmol), Ph$_3$P (137 mg, 0.52 mmol), DIAD (106 mg, 0.52 mmol) and the mixture was stirred for 1 h30 at rt. The solution was filtered and concentrated under vacuum. The residue was purified by flash chromatography on silica gel (cyclohexane/EtOAc 80/20 to 20/80) then on preparative TLC (DCM/MeOH 96/4) to give 10-allyloxy-5-(2-[[N,N'-bis(tert-butoxycarbonyl)carbamimidoyl]amino]ethyl)-3-thia-5,8,10-triaza-tricyclo[6.2.1.0$^{2.6}$]undec-2(6)-ene-4,9-dione (6a) (139.6 mg, 0.26 mmol, 59%) as a white solid.

MS m/z ([M+H]$^+$) 539.

MS m/z ([M−H]$^−$) 537.

1H NMR (300MHz, CDCl$_3$): δ(ppm) 1.49 (s, 9H), 1.55 (s, 9H), 3.31 (d, J=10.6 Hz, 1H), 3.42-3.51 (m, 1H), 3.63 (dd, J=2.9/10.8 Hz, 1H), 3.87-4.06 (m, 2H), 4.13 (d, J=2.4 Hz, 1H), 4.15-4.27 (m, 2H), 4.34-4.48 (m, 3H), 5.27-5.38 (m, 2H), 5.94-6.03 (m,1H).

Step 2: Preparation of Intermediate Sodium [5-(2-[[N,N$^1$-bis(tert-butoxycarbonyl)carbamimidoyl]amino]ethyl)-4,9-dioxo-3-thia-5,8,10-triaza-tricyclo[6.2.1.0$^{2.6}$]undec-2(6)-en-10-yl] sulfate (6b)

Using the procedure described in example 3 (step 9), 10-allyloxy-5-(2-[[N,N$^1$-bis(tert-butoxycarbonyl)carbamimidoyl]amino]ethyl)-3-thia-5,8,10-triaza-tricyclo[6.2.1.0$^{2.6}$]undec-2(6)-ene-4,9-dione (6a) (139.6 mg, 0.26 mmol) is converted to sodium [5-(2-[[N,N$^1$-bis(tert-butoxycarbonyl)carbamimidoyl]amino]ethyl)-4,9-dioxo-3-thia-5,8,10-triaza-tricyclo[6.2.1.0$^{2.6}$]undec-2(6)-en-10-yl] sulfate (6b) (30 mg, 0.05 mmol, 19% over 3 steps) as a white solid.

MS m/z ([M+H]$^+$) 579.

MS m/z ([M−H]$^−$) 577.

1H NMR (300 MHz, D$_2$O): δ(ppm) 1.45 (s, 9H), 1.49 (s, 9H), 3.48 (d, J=11.4 Hz, 1H), 3.80 (d, J=2.9 Hz, 1H), 3.84 (d, J=3.0 Hz, 1H), 3.86-3.98 (m, 2H), 4.01-4.15 (m, 2H), 4.26-4.32 (m, 1H), 4.79 (m under D$_2$O peak, 1H).

Step 3: Preparation of Sodium and 2,2,2-trifluoroacetate [5-(2-quanidiniumethyl)-4,9-dioxo-3-thia-5,8,10-triaza-tricyclo[6.2.1.0$^{2.6}$]undec-2(6)-en-10-yl] sulfate (Example 6)

At 0° C., a solution of TFA (636 µL) in DCM (636 µL) was prepared and added, drop by drop, to a solution of sodium [5-(2-[[N,N'-bis(tert-butoxycarbonyl)carbamimidoyl]amino]ethyl)-4,9-dioxo-3-thia-5,8,10-triaza-tricyclo[6.2.1.0$^{2.6}$]undec-2(6)-en-10-yl] sulfate (6b) (17 mg, 0.028 mmol) in DCM (636 µL) at 0° C. The mixture was stirred for 9 h at this temperature then concentrated under nitrogen flux. The residue was purified by chromatography C18 reverse phase to provide sodium and 2,2,2-trifluoroacetate [5-(2-guanidiniumethyl)-4,9-dioxo-3-thia-5,8,10-triaza-tricyclo[6.2.1.0$^{2.6}$]undec-2(6)-en-10-yl] sulfate (Example 6) (2.3 mg, 4.4 µmol, 16%) as a white solid.

MS m/z ([M+H]$^+$) 379.

MS m/z ([M−H]$^−$) 377.

1H NMR (300 MHz, DMSO): δ(ppm) 3.33 (m under D$_2$O peak, 3H), 3.56 (dd, J=2.7/11.2 Hz, 1H), 3.66 (m, 2H), 4.11 (d, J=16.8 Hz, 1H), 4.22 (d, J=16.8 Hz, 1H), 4.56 (d, J=2.4 Hz, 1H), 7.00-7.34 (m, 3H), 7.55-7.59 (m, 1H).

Compounds below could be obtained according to schemes 1-6.

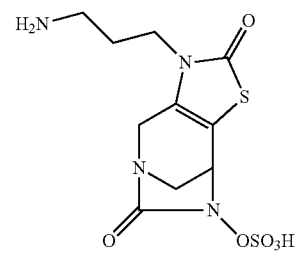

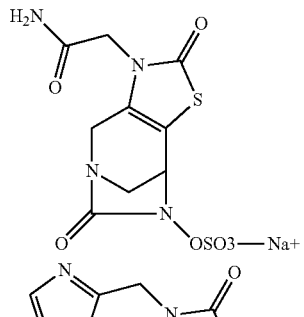

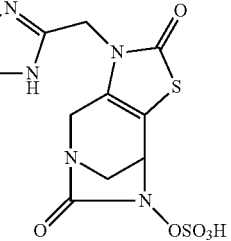

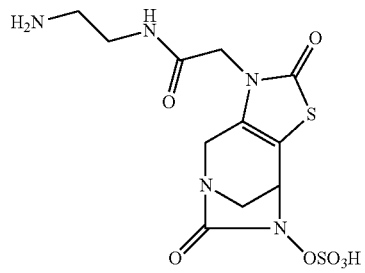

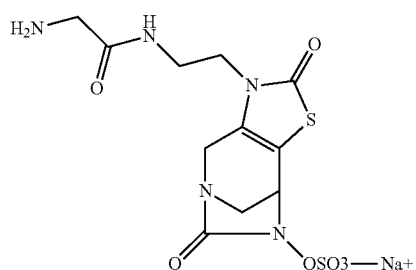

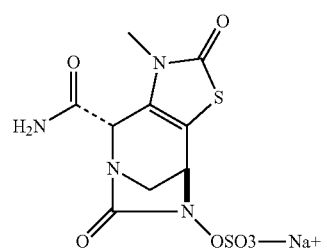

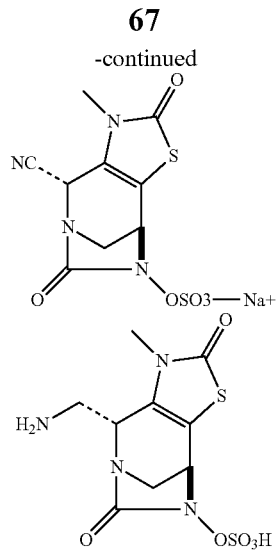

Example 7

Biological Activity

Method 1: β-lactamase Inhibitory Activity, Determination of $IC_{50}$ (Table 1)

Enzyme activity was monitored by spectrophotometric measurement of nitrocefin (NCF-TOKU-E, N005) hydrolysis at 485 nm, at room temperature and in assay buffer A: 100 mM Phosphate pH7, 2% glycerol and 0.1 mg/mL Bovine serum albumin (Sigma, B4287). Enzymes were cloned in E. coli expression vector, expressed and purified in house using classical procedures. To a transparent polystyrene plate (Corning, 3628) were added in each well 5 μL DMSO or inhibitor dilutions in DMSO and 80 μL enzyme in buffer A. Plates were immediately read at 485 nm in a microplate spectrophotometer (BioTek, PowerWave HT) to enable background subtraction. After 30 min of pre-incubation at room temperature, 15 μL of NCF (200 μM final) were finally added in each well. Final enzyme concentrations were 0.1 nM (TEM-1), 0.075 nM (SHV-1), 0.4 nM (CTX-M-15), 1 nM (KPC-2), 0.2 nM (P99 AmpC), 0.2 nM (CMY-37), 0.4 nM (AmpC P. aeruginosa), 0.2 nM (OXA-1), 1.2 nM (OXA-11), 0.4 nM (OXA-15) and 0.3 nM (OXA-48). After 20 min incubation at room temperature, plates were once again read at 485 nm. Enzyme activity was obtained by subtracting the final signal by the background, and was converted to enzyme inhibition using non inhibited wells. $IC_{50}$ curves were fitted to a classical Langmuir equilibrium model with Hill slope using XLFIT (IDBS).

Method 2: MIC of Compounds and Synergy with ceftazidime Against Bacterial Isolates (Table 2 and 3)

Compounds of the present invention were assessed against genotyped bacterial strains alone or in combination with the β-lactam ceftazidime (CAZ). In the assays, MICs of said compounds, or of ceftazidime at fixed concentrations of said compounds were determined by the broth microdilution method according to the Clinical Laboratory Standards Institute (CLSI-M7-A7). Briefly, compounds alone according to the invention were prepared in DMSO and spotted (2 μL each) on sterile polystyrene plates (Corning, 3788). Compounds and ceftazidime dilutions were prepared in DMSO and spotted (1 μL each) on sterile polystyrene plates (Corning, 3788). Log phase bacterial suspensions were adjusted to a final density of $5 \times 10^5$ cfu/mL in cation-adjusted Mueller-Hinton broth (Becton-Dickinson) and added to each well (98 μL). Microplates were incubated for 16-20 h at 35 °C. in ambient air. The MIC of of the compounds was defined as the lowest concentration of said compounds that prevented bacterial growth as read by visual inspection. The MIC of ceftazidime at each compound concentration was defined as the lowest concentration of ceftazidime that prevented bacterial growth as read by visual inspection.

TABLE 2

Bacterial species used in MIC determination

| Strains | | Resistance mechanism |
| --- | --- | --- |
| E. cloacae | 260508 | TEM-1, CTX-M-15 |
| E. coli | UFR61O | TEM-1, KPC-2 |
| K. pneumoniae | BAA-1898 | TEM-1, SHV-11, SHV-12, KPC-2 |
| K. pneumoniae | 160143 | TEM-1, SHV-1, CTX-M-15, KPC-2, OXA-1 |
| K. pneumoniae | UFR68 | TEM-1, SHV-11, CTX-M-15, KPC-3 |
| E. cloacae | P99 | AmpC |
| E. cloacae | UFR85 | TEM-1, CTX-M-15, derepressed AmpC |
| E. cloacae | UFR70 | TEM-1, CTX-M-15, CMY-2, OXA-1, Porin loss |
| K. pneumoniae | UFR77 | CMY-2 |
| E. coli | UFR74 | SHV-1, DHA-1 |
| E. coli | UFR18 | CTX-M-15, OXA-204 |
| E. coli | 131119 | TEM-1, OXA-48 |
| K. oxytoca | UFR21 | TEM-1, CTX-M-15, OXA-48 |
| K. pneumoniae | UFR24 | TEM-1, SHV-2, SHV-11, OXA-1, OXA-48, OXA-47 |
| K. pneumoniae | 6299 | TEM-1, SHV-11, OXA-163 |
| E. coli | RGN238 | OXA-1 |
| K. pneumoniae | 200047 | TEM-1, SHV-32, CTX-M-15, OXA-1 |

TABLE 1

$IC_{50}$ (μM) for β-lactamase Inhibitory Activity

| | $IC_{50}$ β-lactamase (μM) | | | | | | | | | | |
| --- | --- | --- | --- | --- | --- | --- | --- | --- | --- | --- | --- |
| | (A) | | | | (C) | | | (D) | | | |
| | | | | | AmpC | | AmpC | | | | |
| | TEM-1 | SHV-1 | CTX-M-15 | KPC-2 | (P99) | CMY-37 | (PAE) | OXA-1 | OXA-11 | OXA-15 | OXA-48 |
| Example 1 | 0.0033 | 0.012 | 0.00069 | 0.0033 | 0.048 | 0.042 | 0.19 | 0.063 | 0.040 | 0.25 | 0.00089 |
| Example 2 | 0.00064 | 0.0013 | 0.0011 | 0.0013 | 0.016 | 0.030 | 0.22 | 0.038 | 0.0041 | 0.057 | 0.00067 |
| Example 3 | 0.0058 | 0.020 | 0.00049 | 0.0034 | 0.0059 | 0.010 | 0.20 | 0.13 | 0.016 | 0.097 | 0.0017 |
| Example 4 | 0.0046 | 0.021 | 0.0013 | 0.0074 | 0.14 | 0.22 | 1.2 | 0.46 | 0.082 | 0.30 | 0.0041 |
| Example 5 | 0.0018 | 0.0060 | 0.00068 | 0.0017 | 0.024 | 0.062 | 0.37 | 0.31 | 0.031 | 0.19 | 0.00079 |
| Example 6 | 0.0070 | 0.012 | 0.0054 | 0.0057 | 0.38 | 0.59 | 1.5 | 1.7 | 0.13 | 0.12 | 0.0016 |

TABLE 2-continued

Bacterial species used in MIC determination

| Strains | | Resistance mechanism |
|---|---|---|
| E. coli | 190317 | TEM-1, SHV-12, CTX-M-15, OXA-1 |
| E. coli | UFR32 | TEM-1, VEB-1, OXA-10 |
| E. cloacae | UFR38 | CTX-M-15, NDM-1 |
| C. murliniae | 210102 | VIM-4 |
| E. coli | UFR52 | TEM-1, SHV-12, IMP-8 |
| P. aeruginosa | CIP107051 | TEM-24 |
| P. aeruginosa | CIP105250 | OXA-15 |
| P. aeruginosa | UFR35 | OXA-23 |
| P. aeruginosa | UFR90 | derepressed AmpC, OprD– |
| P. aeruginosa | UFR92 | derepressed AmpC, OprD– |
| P. aeruginosa | UFR93 | derepressed AmpC, OprD–, MexAB+, MexXY+ |
| P. aeruginosa | UFR47 | VIM-1 |
| P. aeruginosa | UFR48 | VIM-2 |
| P. aeruginosa | UFR59 | IMP-29 |

TABLE 3

MIC of compounds

MIC compounds of the invention alone (µg/mL)

| Strains | Example 1 | Example 2 | Example 3 | Example 4 | Example 5 | Example 6 |
|---|---|---|---|---|---|---|
| 260508 | 4 | 4 | | 8 | 4 | |
| UFR61O | 4 | 8 | | 4 | 2 | |
| BAA-1898 | 16 | 32 | >32 | 16 | 8 | 16 |
| 160143 | 8 | 16 | | 16 | 8 | |
| UFR68 | 32 | 32 | | 16 | 8 | |
| P99 | 8 | 16 | >32 | 0.5 | 8 | 1 |
| UFR85 | 8 | 8 | | 2 | 2 | |
| UFR70 | 4 | 8 | | 4 | 1 | |
| UFR77 | 8 | 4 | | 16 | 4 | |
| UFR74 | 4 | 8 | | 16 | 4 | |
| UFR18 | 4 | 4 | | 0.5 | 2 | |
| 131119 | 1 | 2 | >32 | 2 | 1 | |
| UFR21 | 8 | 8 | | 4 | 4 | |
| UFR24 | 8 | 16 | | 16 | 4 | |
| 6299 | 16 | 8 | >32 | 32 | 8 | >32 |
| RGN238 | 2 | 1 | >32 | 8 | 1 | 4 |
| 200047 | 4 | 4 | | 8 | 2 | |
| 190317 | 2 | 4 | >32 | 1 | 1 | 1 |
| UFR32 | 4 | 4 | | 1 | 2 | |
| UFR38 | 8 | 8 | | 0.5 | 2 | |
| 210102 | 32 | 16 | | 4 | 8 | |
| UFR52 | 8 | 8 | | 2 | 0.5 | |
| CIP107051 | >128 | >32 | >32 | 16 | >32 | 8 |
| CIP105250 | >32 | >32 | >32 | 8 | >32 | 8 |
| UFR35 | | | | 8 | | |
| UFR90 | | | | 8 | | |
| UFR92 | | | | 8 | | |
| UFR93 | | | | 16 | | |
| UFR47 | | | | 16 | | |
| UFR48 | | | | 8 | | |
| UFR59 | | | | 8 | | |

TABLE 4

MIC of Ceftazidime/compound combinations combination of CAZ and compounds of the invention at 4 µg/mL: MIC (µg/mL)

| Strains | CAZ | Example 1 | Example 2 | Example 3 | Example 4 | Example 5 | Example 6 |
|---|---|---|---|---|---|---|---|
| 260508 | 128 | <0.25 | <0.25 | | <0.25 | <0.25 | |
| UFR61O | 128 | <0.25 | <0.25 | | <0.25 | <0.25 | |
| BAA-1898 | 256 | 64 | >128 | >128 | ≤0.125 | 4 | ≤0.125 |
| 160143 | 128 | 0.5 | 8 | | ≤0.25 | <0.25 | |
| UFR68 | >128 | 64 | 32 | | <0.25 | ≤0.25 | |
| P99 | 128 | 0.5 | 4 | 128 | <0.25 | 0.25 | <0.25 |
| UFR85 | 128 | <0.25 | 16 | | <0.25 | <0.25 | |
| UFR70 | >128 | <0.25 | 1 | | <0.25 | <0.25 | |
| UFR77 | 64 | ≤0.25 | 0.25 | | ≤0.25 | <0.25 | |
| UFR74 | 64 | <0.25 | 1 | | ≤0.25 | <0.25 | |
| UFR18 | >128 | <0.25 | 0.5 | | <0.25 | <0.25 | |
| 131119 | 0.5 | <0.25 | <0.25 | | <0.25 | <0.25 | |
| UFR21 | 128 | 2 | 16 | | <0.25 | <0.25 | |
| UFR24 | >128 | 4 | 4 | | ≤0.25 | <0.25 | |
| 6299 | 256 | 4 | 4 | 128 | ≤0.125 | ≤0.125 | ≤0.125 |
| RGN238 | 0.5 | <0.25 | <0.25 | | <0.25 | <0.25 | |
| 200047 | 128 | <0.25 | <0.25 | | <0.25 | <0.25 | |
| 190317 | 128 | ≤0.125 | <0.25 | 32 | <0.25 | <0.25 | <0.25 |
| UFR32 | >128 | <0.25 | <0.25 | | <0.25 | <0.25 | |
| UFR38 | >128 | >128 | >128 | | <0.25 | <0.25 | |
| 210102 | >128 | >128 | >128 | | <0.25 | 64 | |
| UFR52 | >128 | 0.5 | >128 | | <0.25 | <0.25 | |
| CIP107051 | 256 | 4 | 16 | 64 | 4 | 4 | 8 |
| UFR35 | 2 | 4 | | | 2 | | |
| UFR90 | 64 | 64 | | | 1 | | |
| UFR92 | 32 | 32 | | | ≤0.25 | | |

The invention claimed is:
1. A compound of formula (I)

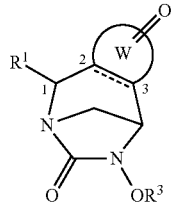

wherein:
W, unsubstituted or substituted by one or more T, is a non-aromatic, unsaturated 5- or 6-member heterocycle comprising at least one N—$R^2$ group and a $(X)_n$ group;
X, identical or different, is independently selected from the group consisting of represents C(O), O, N, N($R^2$), S, S(O), and S(O)$_2$;
$R^1$ is selected from the group consisting of a carbon-linked 4- or 5- or 6-member heterocycle comprising at least one nitrogen atom that is aromatic or saturated or totally unsaturated or partially unsaturated and optionally substituted by one or more $T^1$, H, —CN, —C(O)NHQ$^1$, —C(O)NHOQ$^1$, —C(O)NH—NHQ$^1$, —C(O)O—NHQ$^1$, —C(O)OQ$^1$, —(CH$_2$)$_m$OC(O)OQ$^1$, —(CH$_2$)$_m$OQ$^1$, —(CH$_2$)$_m$OC(O)Q$^1$, —(CH$_2$)$_m$OC(O)NQ$^1$Q$^2$, —(CH$_2$)$_m$—NHC(O)Q$^1$, —(CH$_2$)$_m$NHS(O)$_2$Q$^1$, —(CH$_2$)$_m$NHS(O)$_2$NQ$^1$Q$^2$, —(CH$_2$)$_m$NHC(O)OQ$^1$, —(CH$_2$)$_m$NHC(O)NQ$^1$Q$^2$, —(CH$_2$)$_m$NHQ$^3$, —(CH$_2$)$_m$NH—C(NHQ$^3$)=NQ$^4$, —(CH$_2$)$_m$NH—CH=NQ$^3$, and —C(NHQ$^3$)=NQ$^4$;
$R^2$ is one of the following:
R2, identical or different, is independently selected from the group consisting of (CH$_2$)$_q$OQ$^5$, —C(O)(CH$_2$)$_v$OQ$^5$, —(C(O))$_w$(CH$_2$)$_v$—CN, —(CH$_2$)$_q$OC(O)Q$^5$, —C(O)—(CH$_2$)$_v$OC(O)Q$^5$, —(C(O))$_w$(CH$_2$)$_v$—C(O)OQ$^5$, —(CH$_2$)$_q$—OC(O)OQ$^5$, —C(O)(CH$_2$)$_v$—OC(O)OQ$^5$, —(CH$_2$)$_q$—OC(O)NQ$^5$Q$^6$, —C(O)(CH$_2$)$_v$—OC(O)NQ$^5$Q$^6$, —(C(O))$_w$(CH$_2$)$_v$—C(O)NQ$^5$Q$^6$, —(C(O))$_w$(CH$_2$)$_v$—C(O)ONQ$^5$, —(C(O))$_w$(CH$_2$)$_v$—C(O)NHOQ$^5$, —(C(O))$_w$(CH$_2$)$_v$—C(O)NH—NHQ$^5$, —(C(O))$_w$(CH$_2$)$_v$—C(O)O—NHQ$^5$, —(CH$_2$)$_q$—NHC(O)Q$^5$, —C(O)(CH$_2$)$_v$—NHC(O)Q$^5$, —(CH$_2$)$_q$NHS(O)$_2$Q$^5$, —C(O)(CH$_2$)$_v$NHS(O)$_2$Q$^5$, —(CH$_2$)$_q$NHS(O)$_2$NQ$^5$Q$^6$, —C(O)(CH$_2$)$_v$NHS(O)$_2$NQ$^5$Q$^6$, —(CH$_2$)$_q$—NHC(O)OQ$^5$, —C(O)(CH$_2$)$_v$—NHC(O)OQ$^5$, —(CH$_2$)$_q$—NHC(O)NQ$^5$Q$^6$, —C(O)(CH$_2$)$_v$—NHC(O)NQ$^5$Q$^6$, —(CH$_2$)$_q$NQ$^5$Q$^6$, —C(O)(CH$_2$)$_v$NQ$^5$Q$^6$, —(CH$_2$)$_q$—NH—C(NHQ$^3$)=NQ$^4$, —C(O)(CH$_2$)$_v$—NH—C(NHQ$^3$)=NQ$^4$, —(CH$_2$)$_q$—NH—CH=NQ$^3$, —C(O)(CH$_2$)$_v$—NH—CH=NQ$^3$, —(C(O))$_w$(CH$_2$)$_v$—C(NHQ$^3$)=NQ$^4$, —C(O)NQ$^5$Q$^6$, and —C(NHQ$^3$)=NQ$^4$; or
$R^2$, identical or different, is independently selected from the group consisting of (C(O))$_w$—C$_1$-C$_3$-alkyl that is optionally substituted by one or more $T^2$, (C(O))$_w$—C$_1$-C$_3$-fluoroalkyl that is optionally substituted by one or more $T^2$, (C(O))$_w$(CH$_2$)$_p$—C$_3$-C$_6$-cycloalkyl that is optionally substituted by one or more $T^2$, —(C(O))$_w$—(CH$_2$)$_p$—C$_3$-C$_6$-cyclofluoroalkyl that is optionally substituted by one or more $T^2$, and —(C(O))$_w$—(CH$_2$)$_p$-(4- or 5- or 6-member aromatic or saturated or totally unsaturated or partially unsaturated heterocycle) that is optionally substituted by one or more $T^2$;
$R^3$ is selected from the group consisting of SO$_3$H, CFHCO$_2$H, and CF$_2$CO$_2$H;
$Q^1$ and $Q^2$ are one of the following:
$Q^1$ and $Q^2$, identical or different, are independently selected from the group consisting of H, —(CH$_2$)$_q$NHQ$^3$, —(CH$_2$)$_q$—NH—C(NHQ$^3$)=NQ$^4$, (CH$_2$)$_q$—NH—CH=NQ$^3$, (CH$_2$)$_v$—C(NHQ$^3$)=NQ$^4$, —(CH$_2$)$_q$OQ$^3$, and —(CH$_2$)$_v$CONHQ$^3$; or
$Q^1$ and $Q^2$, identical or different, are independently elected from the group consisting of a C$_1$-C$_3$ alkyl optionally substituted by one or more $T^2$ and —(CH$_2$)$_p$-(4- or 5- or 6-member heterocycle) optionally substituted by one or more $T^2$; or
$Q^1$ and $Q^2$ and the nitrogen atom to which they are bonded, form a saturated or partially unsaturated 4- or 5- or 6-member heterocycle comprising 1 or 2 or 3 or 4 heteroatoms;
$Q^3$ and $Q^4$, identical or different, are independently selected from the group consisting of H and a C$_1$-C$_3$ alkyl;
$Q^5$ and $Q^6$ are one of the following:
$Q^5$ and $Q^6$, identical or different, are independently selected from the group consisting of H, —(CH$_2$)$_q$NHQ$^3$, —(CH$_2$)$_q$—NH—C(NHQ$^3$)=NQ$^4$, (CH$_2$)$_q$—NH—CH=NQ$^3$, (CH$_2$)$_v$—C(NHQ$^3$)=NQ$^4$, —(CH$_2$)$_q$OQ$^3$, and —(CH$_2$)$_v$CONHQ$^3$; or
$Q^5$ and $Q^6$, identical or different, are independently selected from the group consisting of a C$_1$-C$_4$ alkyl optionally substituted by one or more $T^2$ and —(CH$_2$)$_p$-(4- or 5- or 6-member heterocycle) optionally substituted by one or more $T^2$; or
$Q^5$ and $Q^6$ and the nitrogen atom to which they are bonded form a saturated or partially unsaturated 4- or 5- or 6-member heterocycle comprising 1 or 2 or 3 or 4 heteroatoms;
$T^1$ is one of the following:
$T^1$, identical or different, is independently selected from the group consisting of F, —(CH$_2$)$_p$OQ$^1$, —(CH$_2$)$_p$—CN, —(CH$_2$)$_p$OC(O)Q$^1$, —(CH$_2$)$_p$—C(O)OQ$^1$, —(CH$_2$)$_p$—OC(O)OQ$^1$, (CH$_2$)$_p$—OC(O)NHQ$^1$, —(CH$_2$)$_p$—C(O)NHQ$^1$, —(CH$_2$)$_p$—C(O)NHOQ$^1$, —(CH$_2$)$_p$—C(O)NH—NHQ$^1$, —(CH$_2$)$_p$—C(O)O—NHQ$^1$, —(CH$_2$)$_p$—NHC(O)Q$^1$, —(CH$_2$)$_p$NHS(O)$_2$Q$^1$, —(CH$_2$)$_p$NHS(O)$_2$NQ$^1$Q$^2$, —(CH$_2$)$_p$—NHC(O)OQ$^1$, —(CH$_2$)$_p$—NHC(O)NQ$^1$Q$^2$, —(CH$_2$)$_p$NHQ$^1$, —(CH$_2$)$_p$—NH—C(NHQ$^3$)=NQ$^4$, —(CH$_2$)$_p$NH—CH=NQ$^3$, and (CH$_2$)$_p$—C(NHQ$^3$)=NQ$^4$; or
$T^1$, identical or different, is independently selected from the group consisting of C$_1$-C$_3$ alkyl optionally substituted by one or more $T^2$, C$_1$-C$_3$ fluoroalkyl optionally substituted by one or more $T^2$, O—C$_1$-C$_3$-fluoroalkyl optionally substituted by one or more $T^2$, and —(CH$_2$)$_p$-(4- or 5- or 6-member heterocycle comprising at least one nitrogen atom that is aromatic or saturated or totally unsaturated or partially unsaturated) optionally substituted by one or more $T^2$;
$T^2$, identical or different, is independently selected from the group consisting of OH, NH$_2$, and CONH$_2$;
T, identical or different, is independently selected from the group consisting of F, C$_1$-C$_3$ alkyl, C$_1$-C$_3$ fluoroalkyl, O—C$_1$-C$_3$ fluoroalkyl, -(L)$_w$-(CH$_2$)$_p$—C$_3$-C$_6$ cycloalkyl; -(L)$_w$-(CH$_2$)$_p$—C$_3$-C$_6$ cyclofluoroalkyl, -(L)$_w$-(CH$_2$)$_p$-heterocycle, -(L)$_w$-(CH$_2$)$_p$—CN, -(L)$_w$-(CH$_2$)$_p$OC(O)Q$^5$, -(L)$_w$-(CH$_2$)$_p$—C(O)OQ$^5$, -(L)$_w$-(CH$_2$)$_p$OC(O)OQ$^5$, -(L)$_w$-(CH$_2$)$_p$—OC(O)NQ$^5$Q$^6$, -(L)$_w$-(CH$_2$)$_p$—C(O)NQ$^5$Q$^6$, -(L)$_w$-(CH$_2$)$_p$—C(O)NQ$^5$OQ$^6$, -(L)$_w$-(CH$_2$)$_p$—C(O)NQ$^5$—NQ$^5$Q$^6$, -(L)$_w$-(CH$_2$)$_p$—NQ$^5$C(O)Q$^6$, -(L)$_w$-(CH$_2$)$_p$NQ$^5$Q(O)$_2$Q$^6$, -(L)$_w$-(CH$_2$)$_p$—NQ$^5$C(O)OQ$^6$, -(L)$_w$-(CH$_2$)$_p$—NQ$^5$C(O)NQ$^5$Q$^6$, -(L)$_w$-(CH$_2$)$_p$NQ$^5$Q$^6$, -(L)$_w$-(CH$_2$)$_p$—NH—C(NHQ$^3$)=NQ$^4$, -(L)$_w$-(CH$_2$)$_p$—NH—CH=NQ$^3$, and -(L)$_w$(CH$_2$)$_p$—C(NHQ$^3$)=NQ$^4$;

L, identical or different, is independently selected from the group consisting of O, S, N(R$^2$), S(O), and S(O)$_2$;

m is 1 or 2;

n is 0, 1, or 2;

p, identical or different, is independently selected from the group consisting of 0, 1, 2, and 3;

q, identical or different, is independently selected from the group consisting of 2 and 3;

v, identical or different, is independently selected from the group consisting of 1, 2, and 3;

w, identical or different, is independently selected from the group consisting of 0 and 1;

wherein any carbon atom present within any of the foregoing alkyls, cycloalkyls, fluoroalkyls, cyclofluoroalkyls, and heterocycles can be oxidized to form a C=O group;

wherein any sulphur atom present within a heterocycle can be oxidized to form a S=O group or a S(O)2 group; and wherein any nitrogen atom present within a heterocycle or a tertiary amino group can be further quaternized by a methyl group; or a pharmaceutically acceptable salt, a zwitterion, a racemate, a diastereoisomer, an enantiomer, a geometric isomer, or a tautomer of formula (I).

2. The compound according to claim 1 selected from the group consisting of compounds of formulae (A), (B), (I*), (A*), and (B*)

(A)
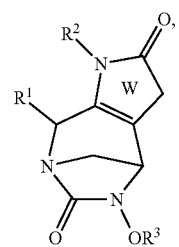

(B)
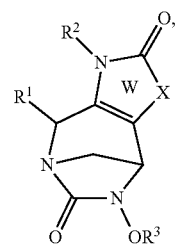

(I*)
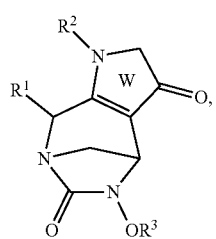

(A*) and
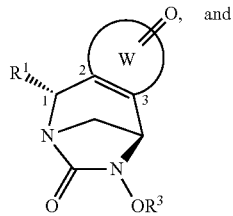

(B*)
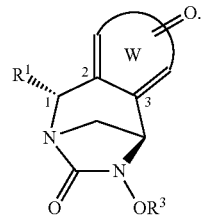

3. The compound according to claim 1 selected from group consisting of compounds of formulae (A1) to (A68) and (B1) to (B8)

(A1)
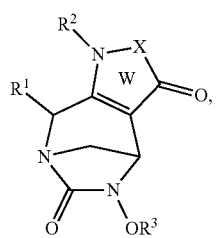

(A2)

(A3)

(A4)

| | |
|---|---|
| 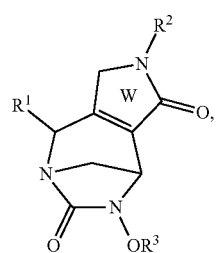 (A5) | 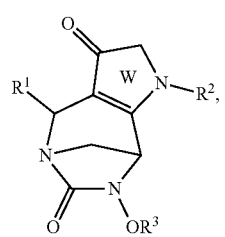 (A11) |
| 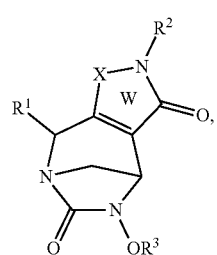 (A6) | 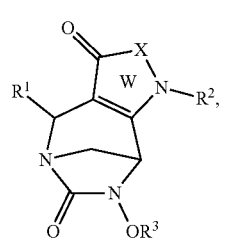 (A12) |
| 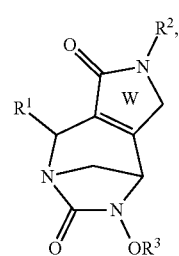 (A7) | 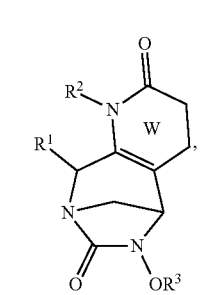 (A13) |
| 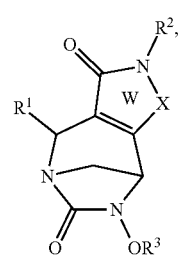 (A8) | 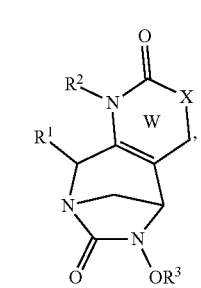 (A14) |
| 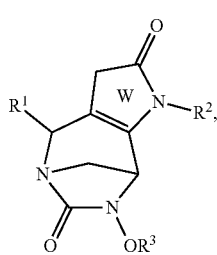 (A9) | 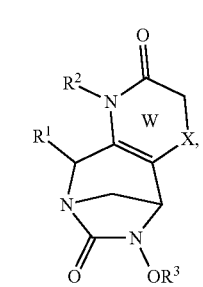 (A15) |
| 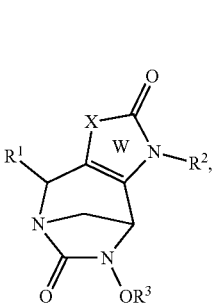 (A10) | 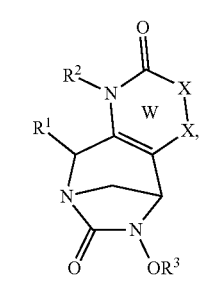 (A16) |

-continued
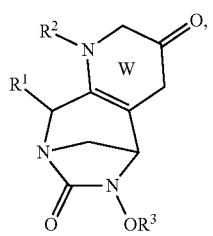 (A17)
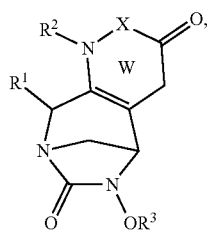 (A18)
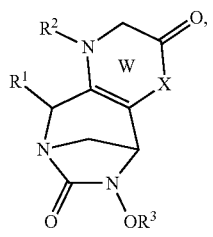 (A19)
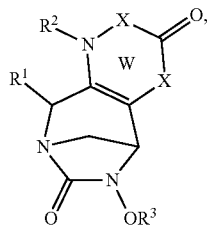 (A20)
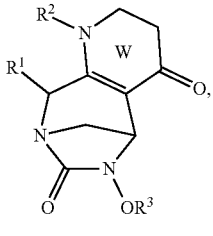 (A21)
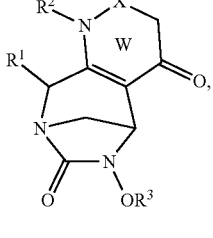 (A22)
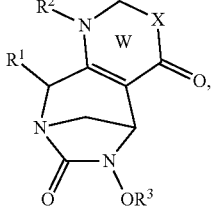 (A23)
-continued
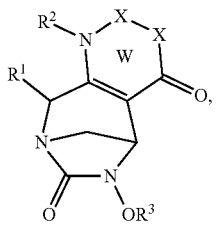 (A24)
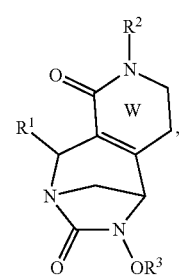 (A25)
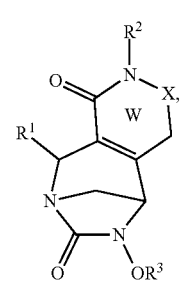 (A26)
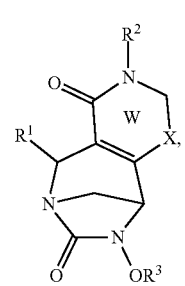 (A27)
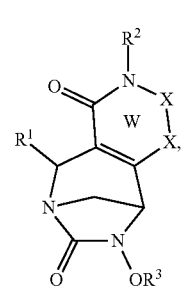 (A28)
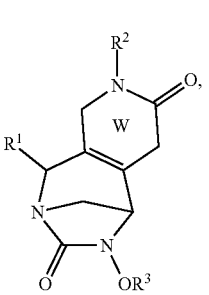 (A29)

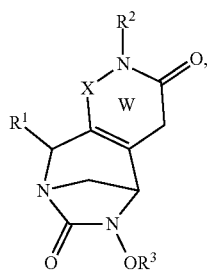 (A30)
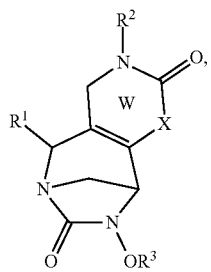 (A31)
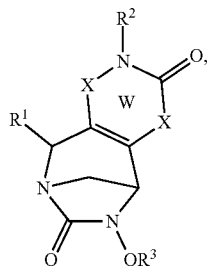 (A32)
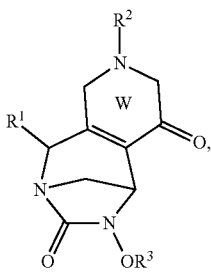 (A33)
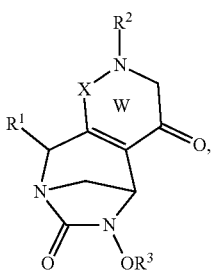 (A34)
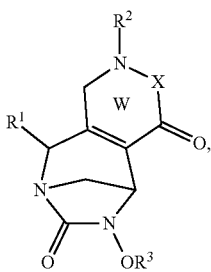 (A35)
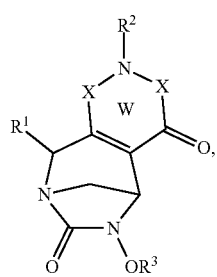 (A36)
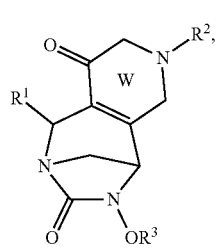 (A37)
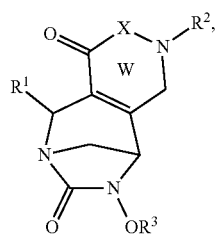 (A38)
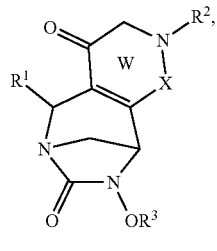 (A39)
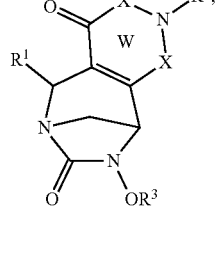 (A40)
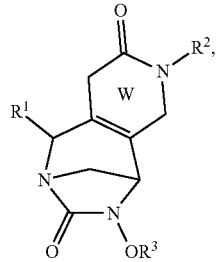 (A41)

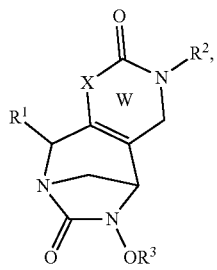 (A42)
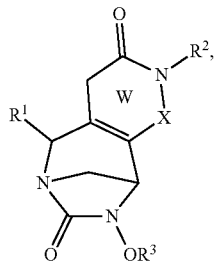 (A43)
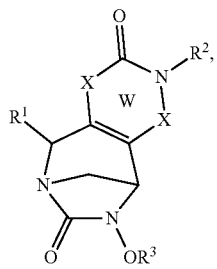 (A44)
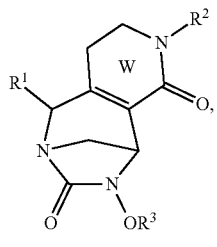 (A45)
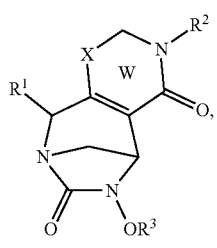 (A46)
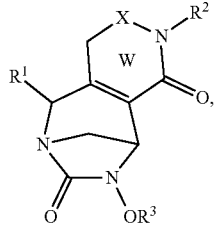 (A47)
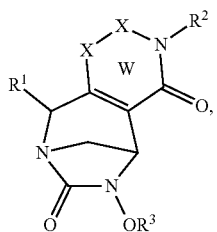 (A48)
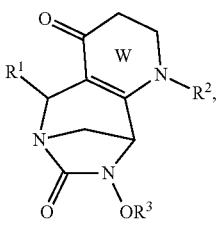 (A49)
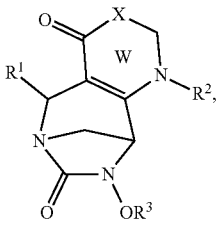 (A50)
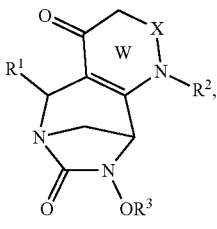 (A51)
(A52)
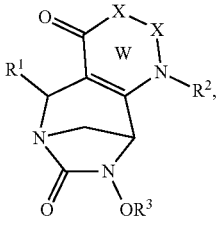 (A53)

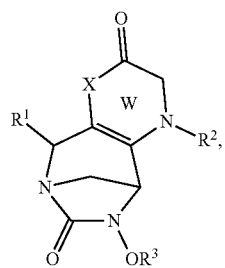 (A54)
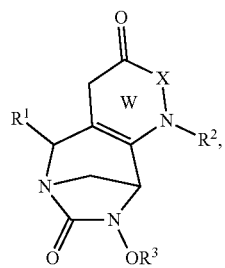 (A55)
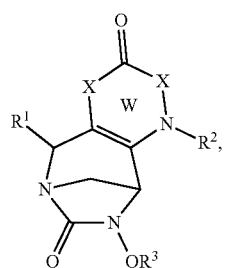 (A56)
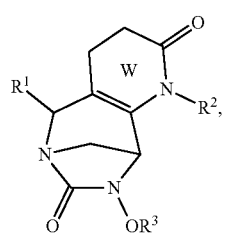 (A57)
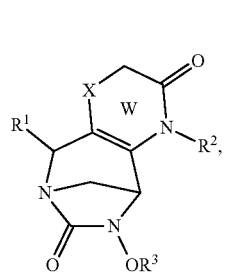 (A58)
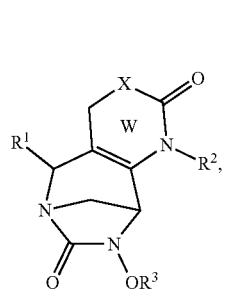 (A59)
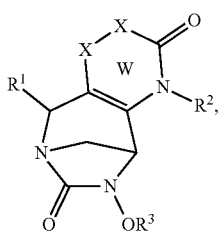 (A60)
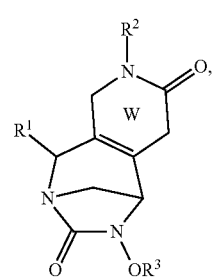 (A61)
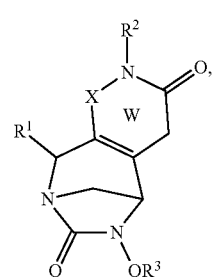 (A62)
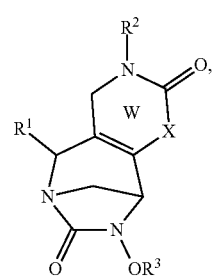 (A63)
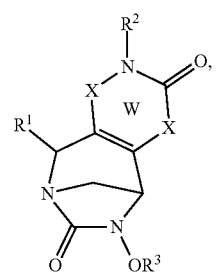 (A64)
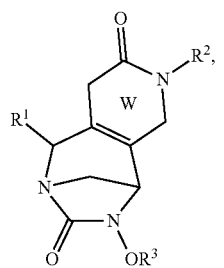 (A65)

(A66) 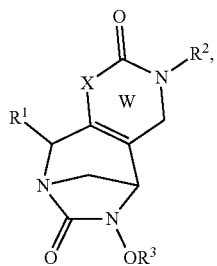

(A67) 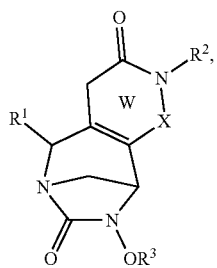

(A68) 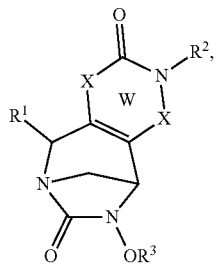

(B1) 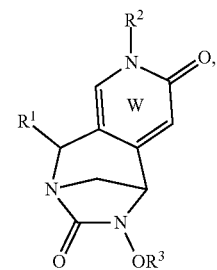

(B2) 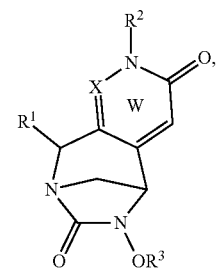

(B3) 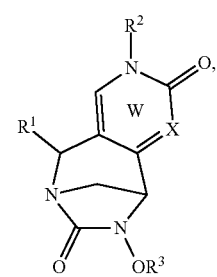

(B4) 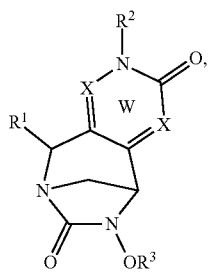

(B5) 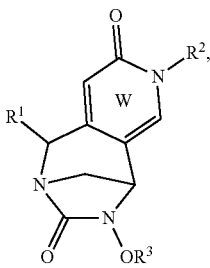

(B6) 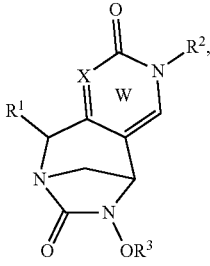

(B7) 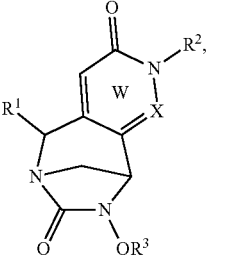

and (B8) 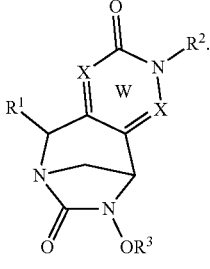

4. The compound according to claim 1, wherein $R^1$ is one of the following:
   $R^1$ is selected from the group consisting of a carbon-linked 4-, 5- or 6-membered heterocycle comprising at least one nitrogen atom that is aromatic or saturated or totally unsaturated or partially unsaturated and optionally substituted by one or more $T^1$, H, —CN; —C(O)NHQ$^1$; —C(O)NHOQ$^1$; —C(O)NH—NHQ$^1$; —(CH$_2$)OQ$^1$; and C(O)OQ$^1$; or
   $R^1$ is selected from the group consisting of —(CH$_2$)NHQ$^3$ and —(CH$_2$)NH—C(NHQ$^3$)=NQ$^4$.

5. The compound according to claim 1, wherein $R^1$ is one of the following:
   $R^1$ is selected from the group consisting of —CN; C(O)NHQ$^1$, —C(O)NHOQ$^1$, and —C(O)NH—NHQ$^1$; or
   $R^1$ is selected from the group consisting of —(CH$_2$)$_m$—OQ$^1$, —(CH$_2$)$_m$—NHC(O)Q$^1$, —(CH$_2$)$_m$—NHC(O)OQ$^1$, and —(CH$_2$)$_m$—NHC(O)NQ$^1$Q$^2$; or
   $R^1$ is a carbon-linked 4- or 5- or 6-member heterocycle comprising at least one nitrogen atom that is saturated or partially unsaturated or totally unsaturated or aromatic and optionally substituted by one or more T$^1$ and further comprises one or two or three additional heteroatoms wherein each additional heteroatom is selected from the group consisting of N, O, S, S(O), and S(O)$_2$; or
   $R^1$ is H.

6. The compound according to claim 1, wherein:
   $R^2$ is selected from the group consisting of —(CH$_2$)$_q$NQ$^5$Q$^6$, —C(O)(CH$_2$)$_v$NQ$^5$Q$^6$, —(CH$_2$)$_q$—NH—C(NHQ$^3$)=NQ$^4$, C(O)NQ$^5$Q$^6$, —(C(O))$_w$(CH$_2$)$_v$—C(NHQ$^3$)=NQ$^4$, —C(NHQ$^3$)=NQ$^4$, —(C(O))$_w$(CH$_2$)$_v$—C(O)NQ$^5$Q$^6$, —(C(O))$_w$—(CH$_2$)$_p$-(4- or 5- or 6-member heterocycle that is aromatic or saturated or totally unsaturated or partially unsaturated), —(CH$_2$)$_q$NHS(O)$_2$NQ$^5$Q$^6$; —C(O)(CH$_2$)$_v$NHS(O)$_2$NQ$^5$Q$^6$; —(CH$_2$)$_q$NHC(O)NQ$^5$Q$^6$; —C(O)(CH$_2$)$_v$NHC(O)NQ$^5$Q$^6$; —(C(O))$_w$(CH$_2$)$_v$—C(O)OQ$^5$; (C(O))$_w$—C$_1$-C$_3$ alkyl; —(CH$_2$)$_q$—NHC(O)OQ$^5$; —C(O)(CH$_2$)$_v$—NHC(O)OQ$^5$; (CH$_2$)$_q$OQ$^5$, and —C(O)(CH$_2$)$_v$OQ$^5$; and
   Q$^5$ and Q$^6$, identical or different, are independently selected from the group consisting of H, (CH$_2$)$_q$, NHQ$^3$, and C$_1$-C$_4$-alkyl.

7. The compound according to claim 1, wherein:
   $R^2$ is selected from the group consisting of —(CH$_2$)$_p$-(4- or 5- or 6-member heterocycle that is aromatic or saturated or totally unsaturated or partially unsaturated), C$_1$-C$_3$ alkyl, —(CH$_2$)$_v$—C(O)OQ$^5$; —(CH$_2$)$_q$—NHC(O)OQ$^5$; —(CH$_2$)$_q$NQ$^5$Q$^6$; —(CH$_2$)$_q$OQ$^5$, and —(CH$_2$)$_v$C(O)NH(CH$_2$)$_q$NHQ$^3$;
   Q$^5$ and Q$^6$, identical or different, are independently selected from the group consisting of H and C$_1$-C$_4$alkyl; and
   Q$^3$ is H.

8. The compound according to claim 1, wherein:
   $R^1$ is one of the following:
   $R^1$ is selected from the group consisting of H, a carbon-linked 4- or 5- or 6-member heterocycle comprising at least one nitrogen atom that is aromatic or saturated or totally unsaturated or partially unsaturated and optionally substituted by one or more T$^1$, —CN, —C(O)NHQ$^1$, —C(O)NHOQ$^1$, —C(O)NH—NHQ$^1$; —(CH$_2$)OQ$^1$, and —C(O)OQ$^1$; or
   $R^1$ is selected from the group consisting of —(CH$_2$)NHQ$^3$ and —(CH$_2$)NH—C(NHQ$^3$)=NQ$^4$; or
   $R^1$ is selected from the group consisting of H, a carbon-linked 4- or 5- or 6-member heterocycle comprising at least one nitrogen atom that is aromatic or saturated or totally unsaturated or partially unsaturated and optionally substituted by one or more T$^1$, —CN; —C(O)NHQ$^1$, —C(O)NHOQ$^1$, —C(O)NH—NHQ$^1$, —C(O)OQ$^1$, —(CH$_2$)OQ$^1$, —(CH$_2$)NHQ$^3$, —(CH$_2$)$_2$NHQ$^3$, —(CH$_2$)NH—C(NHQ$^3$)=NQ$^4$, —(CH$_2$)$_2$NH—C(NHQ$^3$)=NQ$^4$, —(CH$_2$)NH—CH=NQ$^3$, —(CH$_2$)$_2$NH—CH=NQ$^3$, and —C(NHQ$^3$)=NQ$^4$,
   Q$^1$ is H or methyl;
   Q$^3$ and Q$^4$ are H;
   $R^3$ is SO$_3$H;
   W, unsubstituted or substituted by one or more T, is a non-aromatic, unsaturated 5-member heterocycle comprising at least one N—R$^2$ group and a (X)$_n$ group;
   $R^2$ is selected from the group consisting of (C(O))$_w$—C$_1$-C$_3$alkyl, (C(O))$_w$—(CH$_2$)$_v$—C(O)OQ$^5$, —(CH$_2$)$_q$—NH—C(NHQ$^3$)=NQ$^4$, —(C(O))$_w$(CH$_2$)$_v$—C(O)NQ$^5$Q$^6$, (C(O))$_w$—(CH$_2$)$_q$NQ$^5$Q$^6$, —C(O)(CH$_2$)$_v$NHC(O)NQ$^5$Q$^6$, (C(O))$_w$—(CH$_2$)$_q$OQ$^5$, (C(O))$_w$—(CH$_2$)$_q$—NHC(O)OQ$^5$, and —(C(O))$_w$—(CH$_2$)$_p$-(4- or 5- or 6-member heterocycle that is aromatic or saturated or totally unsaturated or partially unsaturated);
   Q$^5$ and Q$^6$, identical or different, are H or C$_1$-C$_4$alkyl;
   w is 0; and
   X is S.

9. The compound according to claim 1, wherein:
   $R^1$ is H;
   $R^3$ is SO$_3$H;
   W, unsubstituted or substituted by one or more T, is a non-aromatic, unsaturated 5-member heterocycle comprising at least one N—R$^2$ group and a (X)$_n$ group;
   $R^2$ is selected from the group consisting of —(CH$_2$)$_p$-(4- or 5- or 6-member heterocycle that is aromatic or saturated or totally unsaturated or partially unsaturated), C$_1$-C$_3$ alkyl, —(CH$_2$)$_v$—C(O)OQ$^5$, —(CH$_2$)$_q$—NHC(O)OQ$^5$, —(CH$_2$)$_q$NQ$^5$Q$^6$, —(CH$_2$)$_q$OQ$^5$, and —(CH$_2$)$_q$C(O)NQ$^5$Q$^6$;
   Q$^5$ and Q$^6$, identical or different, are H or C$_1$-C$_4$alkyl; and
   X is S.

10. The compound according to claim 1 selected from the group consisting of

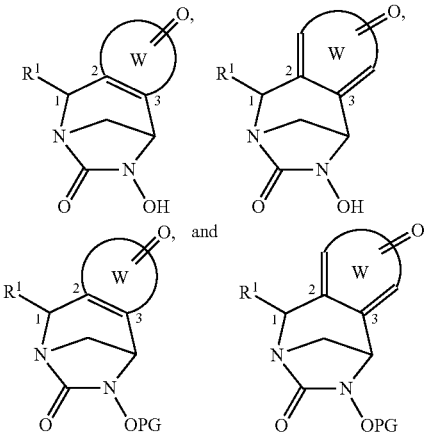

wherein PG, is a protective group.

11. The compound according to claim 1 selected from the group consisting of

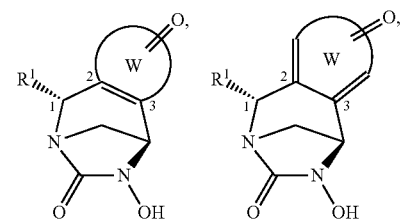

-continued

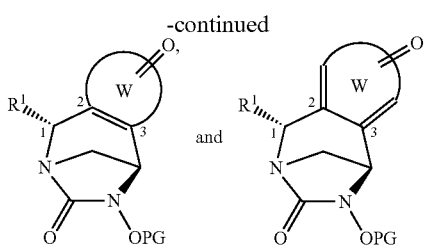

wherein PG is a protective group selected from the group consisting of allyl, benzyl, tertbutyldimethylsilyl (TBDMS), and tert-butoxycarbonyl (Boc).

12. A pharmaceutical composition comprising at least one compound according to claim 1.

13. The pharmaceutical composition according to claim 12 further comprising a an antibacterial compound selected from the group consisting of selected from aminoglycosides, β-lactams, glycylcyclines, tetracyclines, quinolones, fluoroquinolones, glycopeptides, lipopeptides, macrolides, ketolides, lincosamides, streptogramins, oxazolidinones, polymyxins and combinations thereof.

14. The pharmaceutical composition according to claim 12, wherein the antibacterial compound is β-lactams selected from the group consisting penicillin, cephalosporins, penems, carbapenems, monobactam, and combinations thereof.

15. The pharmaceutical composition according to claim 12 further comprising ceftazidime.

16. The pharmaceutical composition according to claim 12 further comprising a pharmaceutically acceptable excipient.

17. A kit comprising a pharmaceutical composition according to claim 11 and at least one second composition according to claim 11.

18. The kit according to claim 17 further comprising ceftazidime.

19. A method for the treatment of bacterial infections comprising the administration of a therapeutically effective amount of the compound of claim 1.

20. The method according to claim 19, wherein the bacterial infection is caused by bacteria producing one or more beta-lactamases.

21. A method according to claim 19, wherein the bacterial infection is caused by gram-negative bacteria.

* * * * *

UNITED STATES PATENT AND TRADEMARK OFFICE
CERTIFICATE OF CORRECTION

Page 1 of 1

PATENT NO. : 10,501,481 B2
APPLICATION NO. : 15/563889
DATED : December 10, 2019
INVENTOR(S) : Brias et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Fifth Day of May, 2020

Andrei Iancu
*Director of the United States Patent and Trademark Office*